(12) United States Patent
Takemura et al.

(10) Patent No.: US 7,186,843 B2
(45) Date of Patent: *Mar. 6, 2007

(54) AMINOMETHYLPYRROLIDINE DERIVATIVES HAVING AROMATIC SUBSTITUENTS

(75) Inventors: Makoto Takemura, Tokyo (JP); Hisashi Takahashi, Tokyo (JP); Katsuhiro Kawakami, Tokyo (JP); Toshiyuki Takeda, Tokyo (JP); Rie Miyauchi, Tokyo (JP)

(73) Assignee: Daiichi Pharmaceutical Co. Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/834,079

(22) Filed: Apr. 29, 2004

(65) Prior Publication Data
US 2004/0209940 A1 Oct. 21, 2004

Related U.S. Application Data

(62) Division of application No. 09/936,050, filed as application No. PCT/JP00/01439 on Mar. 9, 2000, now Pat. No. 6,762,181.

(30) Foreign Application Priority Data
Mar. 10, 1999 (JP) .............................. P.11-062806

(51) Int. Cl.
*C07D 207/09* (2006.01)
*C07D 401/12* (2006.01)
*C07D 403/12* (2006.01)

(52) U.S. Cl. .................... 548/146; 548/206; 548/215; 548/240; 548/314.7; 548/364.1; 548/524; 548/566; 544/179; 544/180; 544/181; 544/238; 544/333; 544/336; 546/279.1; 546/276.4

(58) Field of Classification Search ................ 544/179, 544/180, 181, 238, 333, 336; 546/279.1, 546/276.4; 548/146, 206, 215, 240, 314.7, 548/364.1, 524, 566
See application file for complete search history.

(56) References Cited

U.S. PATENT DOCUMENTS 6,762,181 B1 * 7/2004 Takemura et al. ....... 514/230.2

FOREIGN PATENT DOCUMENTS

| EP | 0 207 420 | 1/1987 |
|---|---|---|
| EP | 0 341 493 | 11/1989 |
| JP | 63-166876 | 7/1988 |
| JP | 9-136886 | 5/1997 |
| JP | 10-287669 | 10/1998 |
| JP | 10-324686 | 12/1998 |
| WO | WO 89/06649 | 7/1989 |
| WO | WO 92/09597 | 6/1992 |
| WO | WO 97/42954 | 11/1997 |

OTHER PUBLICATIONS

International Search Report (PCT./JP00/01439, 2000).
Tomio, Oue, Patent Abstracts of Japan -Publication No. 09221424, "Antitumor Agent," (Aug. 26, 1997).
Schinzer, W.C., et al., "Characterization and Interconversion of Polymorphs of Premafloxacin, a New Quinolone Antibiotic", Journal of Pharmaceutical Sciences, American Pharmaceutical Association, vol. 86, No. 12, Dec. 1997, pp. 1426-1431.
European Search Report dated Feb. 8, 2002.
Office Action—Patent Office of the People's Republic of China, Mar. 14, 2003.

* cited by examiner

*Primary Examiner*—Kahsay Habte
(74) *Attorney, Agent, or Firm*—Sughrue Mion, PLLC

(57) ABSTRACT

This invention provides a quinolone derivative having potent antibacterial activity against various bacteria including drug-resistant strains which is a compound of the following formula wherein $R^1$ is an optionally substituted aromatic group, a salt of the same or a hydrate of both.

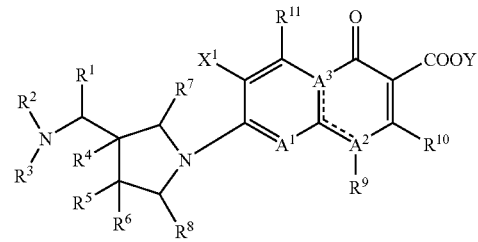

In the formula, $R^2$, $R^3$: hydrogen atom, an alkyl group; $R^4$, $R^5$, $R^6$: hydrogen atom, hydroxyl group, a halogen atom, carbamoyl group, an alkyl group, an alkoxyl group, an alkylthio group; $R^7$, $R^8$: hydrogen atom, an alkyl group; $R^9$: an alkyl group, an alkenyl group, a halogenoalkyl group, a cyclic alkyl group, an aryl group, a heteroaryl group, an alkoxyl group having from 1 to 6 carbon atoms, an alkylamino group; $R^{10}$: hydrogen atom, an alkylthio group; $R^{11}$: hydrogen atom, amino group, hydroxyl group, thiol group, a halogenomethyl group, an alkyl group, an alkenyl group, an alkynyl group, an alkoxyl group; $X^1$: halogen atom, a hydrogen atom; $A^1$: nitrogen atom, C—$X^2$; $X^2$: hydrogen atom, amino group, a halogen atom, cyano group, a halogenomethyl group, a halogenomethoxyl group, an alkyl group, an alkenyl group, an alkynyl group, an alkoxyl group; $A^2$, $A^3$:>C═C (—$A^1$═)—N(—$R^9$)—, >N—C (—$A^1$>)═C (—$R^9$)—; $R^{10}$ and $R^9$ or $R^9$ and $X^2$ may be integrated to form a ring structure; and Y: hydrogen atom, ester forming group.

13 Claims, No Drawings

AMINOMETHYLPYRROLIDINE DERIVATIVES HAVING AROMATIC SUBSTITUENTS

This is a divisional of application Ser. No. 09/936,050 filed Sep. 7, 2001, which issued on Jul. 13, 2005, as U.S. Pat. No. 6,762,181; which is a National Stage Under 35 U.S.C. § 371 and in accordance with the Patent Cooperation Treaty of PCT/JP00/01439 filed Mar. 9, 2000.

TECHNICAL FIELD

This invention relates to a synthetic quinolone antibacterial agent which is useful as a medicament, an animal drug, a drug for fishery use and an antibacterial preservative.

That is, the invention relates to a synthetic quinolone antibacterial agent in which the structure of a substituent at the 7-position of the quinolone mother skeleton or a corresponding position (e.g., the 7-position of the 1,4-dihydro-4-oxoquinoline skeleton; the 10-position of 2,3-dihydro-7-oxo-7H-pyrido[1,2,3-de] [1.4]benzoxazine skeleton or the like) exerts important influence upon the antibacterial activity, namely a quinolone derivative having a 3-[1-amino-1-aromatic group-substituted]methylpyrrolidin-1-yl group as a substituent which can provide excellent antibacterial activity, and to an antibacterial agent and an antibacterial pharmaceutical preparation, which contain the compound.

It further relates to a synthetic quinolone antibacterial drug, namely a 3-[1-amino-1-aromatic group-substituted] methylpyrrolidine, which has a structure that can provide excellent antibacterial activity and is useful as a production intermediate, and to a protected compound thereof.

BACKGROUND ART

Since the discovery of norfloxacin, antibacterial activity and pharmacokinetics of synthetic quinolone antibacterial agents have been sharply improved, and many compounds are now used in the clinical field as chemotherapeutic agents which are effective in almost systemic infectious diseases.

In recent years, generation of bacteria having low sensitivity to synthetic quinolone antibacterial agents has been increasing in the field of clinics. For example, like the case of *Staphylococcus aureus* (MRSA) and pneumcoccus (PRSP) which are non-sensitive to β-lactam antibiotics and enterococcaus (VRE) which is non-sensitive to aminoglycoside antibacterial agents, a case has been increasing in which a Gram-positive bacterium originally resistant to drugs other than synthetic quinolone antibacterial agents also became low-sensitive to synthetic quinolone antibacterial agents. In consequence, development of a drug having further high efficacy has been called for in the field of clinics.

Also, a side effect in which convulsions are induced when a non-steroidal anti-inflammatory drug is simultaneously used, as well as other side effects such as phototoxicity and the like, have been revealed, so that development of a synthetic quinolone antibacterial agent having further high safety has also been called for in the field.

It is known that structures of substituents at the 7-position and 1-position are greatly concerned in the antibacterial activity, pharmacokinetics and safety of synthetic quinolone antibacterial agents. It is already known that a quinolone derivative having 3-(aminomethyl) pyrrolidinyl group as the 7-position substituent shows strong antibacterial activity for Gram-negative and Gram-positive bacteria. For example, there is a 7-[3-(aminomethyl)pyrrolidin-1-yl]quinolonecarboxylic acid derivative [*Journal of Medicinal Chemistry*, vol. 29, p. 445 (1986)]. Also, a 7-[3-(1-aminomethyl)pyrrolidin-1-yl]quinolonecarboxylic acid derivative [*Journal of Medicinal Chemistry*, vol. 36, p. 871 (1993)], a 7-[3-(1-amino-1-methylethyl)pyrrolidin-1-yl]quinolonecarboxylic acid derivative [*Journal of Medicinal Chemistry*, vol. 37, p. 733 (1994)] a 7-[3-(1-aminoalkyl)pyrrolidin-1-yl]quinolonecarboxylic acid derivative [*Chemical & Pharmaceutical Bulletin*, vol. 42, p. 1442(1994)] and the like are known as quinolonecarboxylic acid derivatives having a substituent on the aminomethyl group of 3-(aminomethyl)pyrrolidin-1-yl group.

However, substituents on the aminomethyl group of currently known 3-(aminomethyl)pyrrolidin-1-yl group are only alkyl groups, and a quinolone compound having an aromatic group as a substituent, which is related to the present invention, is not known.

Also, as a reference in which quinolonecarboxylic acid derivatives having a cyclic substituent on the aminomethyl group of 3-(aminomethyl)pyrrolidin-1-yl group are exemplified, there is, for example, JP-W-3-502452 (the term "JP-W" as used herein means an "unexamined published Japanese international patent application"), and it describes compounds represented by two general formulae shown below. However, the cyclic substituent on the aminomethyl group of 3-(aminomethyl)pyrrolidin-1-yl group described in this document is limited to a cyclic alkyl, and there is no disclosure on the 3-[1-amino-1-aromatic group-substituted] methylpyrrolidin-1-yl group related to the invention.

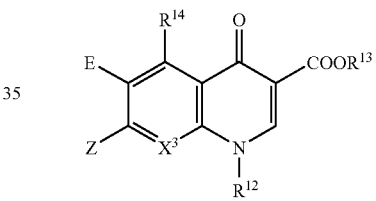

[In the above formula, $R^{12}$ is an alkyl group having from 1 to 4 carbon atoms, a vinyl group, a haloalkyl group, a hydroxyalkyl group having from 2 to 4 carbon atoms, a cycloalkyl group having from 3 to 6 carbon atoms, phenyl group or a phenyl group substituted with a halogen, an alkyl group, $NH_2$ or OH, $R^{14}$ is a straight, branched or cyclic lower alkyl group having from 1 to 3 carbon atoms, and $X^3$ is CH, CF, CCl, CBr, N, $CCF_3$, $CNH_2$, $CNO_2$, CR or COR' (in these formulae, R is a lower alkyl group and R' is hydrogen atom or a lower alkyl group).]

In the above formula, Z is

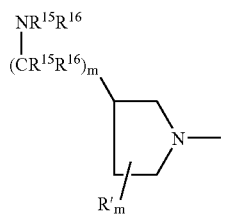

(wherein m is an integer of from 0 to 4, and $R^{15}$ and $R^{16}$ are each independently a hydrogen atom, a lower alkyl group or a cycloalkyl group). In this connection, the definitions of substituents and the like in the above two general formulae are unrelated to those of the of the invention, even if the same symbols are used.

In addition, JP-W-9-503783 discloses 2-pyridone carboxylic acid derivatives of 4H-4-oxoquinolizone skeleton and the like shown by the following formula. However, the quinolone compound of the invention having an aromatic substituent on the aminomethyl group moiety of 3-(aminomethyl)pyrrolidin-1-yl group related to the invention is not also exemplified in this document.

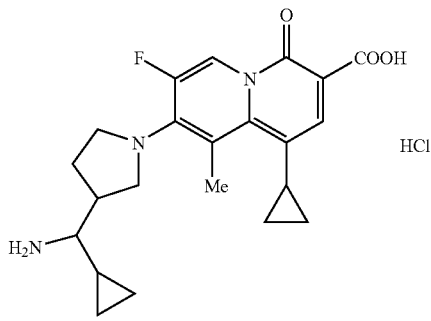

DISCLOSURE OF THE INVENTION

In view of the above, the inventors of the present application have conducted intensive studies with the aim of obtaining excellent quinolone compounds. As a result, it has been found absolutely unexpectedly that an aromatic group-substituted aminomethylpyrrolidine derivative represented by the formula (I) described below, its salts and hydrates thereof can show potent antibacterial activity upon a broad range of Gram-negative and Gram-positive bacteria including drug-resistant bacteria, thereby resulting in the accomplishment of the invention.

The inventors have found that a compound represented by the formula (I) in which an aromatic group-substituted aminomethylpyrrolidine derivative is introduced onto the 10-position of 2,3 dihydro-3-(S) methyl-7-oxo-7H-pyrido[1,2,3-de][1.4]benzoxazine skeleton or the 7-position of 6-fluoro-1-[2-(S)-fluoro-1-(R)-cyclopropyl]-1,4-dihydro-4-oxoquinoline skeleton, its salts and hydrates thereof, having excellent safety, can show broad and excellent antibacterial activity upon any one of Gram-negative and Gram-positive bacteria. At the same time, it was found that it can exert potent antibacterial activity upon drug-resistant Gram-positive bacteria including NRSA, PRSP and VRE, which was not expected before the invention.

Accordingly, the invention relates to a compound presented by the following formula (I), its salts and hydrates thereof

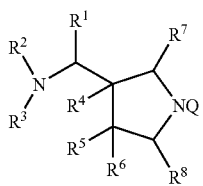

(I)

{wherein $R^1$ represents an aryl group having from 6 to 10 carbon atoms or a heteroaryl group, wherein the heteroaryl group may be a five-membered ring or a six me membered ring and may contain from 1 to 4 hetero atoms optionally selected from nitrogen atom, oxygen atom and sulfur atom, wherein these aryl group and heteroaryl group may have one or more substituents selected from the group consisting of an alkyl group having from 1 to 6 carbon atoms, a halogen atom, hydroxyl group, thiol group, amino group, nitro group, cyano group, cyano group, carboxyl group, carbamoyl group, phenyl group, an alkoxy group having from 1 to 6 carbon atoms, an alkylthio group having from 1 to 6 carbon atoms, an alkoxycarbonyl group having from 2 to 6 carbon atoms, an acyl group having from 2 to 5 carbon atoms and a heteroaryl group (this heteroaryl group may be a five-membered ring or a six-membered ring and may contain from 1 to 4 hetero atoms optionally selected from nitrogen atom, oxygen atom and atom), wherein the alkyl group, alkoxyl group alkylthio group, alkoxycarbonyl group, acyl group, phenyl group and heteroaryl group among them may have one or more substituents selected from the group consisting of a halogen atoms, hydroxyl group, an alkoxyl group having from 1 to 6 carbon atoms and an alkylthio group having from 1 to 6 carbon atoms, and the amino group may have one or two substituents selected from the group consisting of formyl group, an alkyl group having from 1 to 6 carbon atoms, an acyl group having from 2 to 5 carbon atoms and an alkoxycarbonyl group having from 2 to 5 carbon atoms, $R^2$ and $R^3$ each independently represents hydrogen atom or an alkyl group having from 1 to 6 carbon atoms, wherein the alkyl group may have one or more substituents selected from the group consisting of hydroxyl group, a halogen atom, an alkylthio group having from 1 to 6 carbon atoms and an alkoxyl group having from 1 to 6 carbon atoms, $R^4$, $R^5$ and $R^6$ each independently represents hydrogen atom, hydroxyl group, a halogen atom, carbamoyl group, an alkyl group having from 1 to 6 carbon atoms, an alkoxyl having from 1 to 6 carbon atoms or an alkylthio group having from 1 to 6 carbon atoms, wherein the alkyl group among them may have one or more substituents selected from the groups consisting of hydroxyl group, a halogen atom and an alkoxyl group having from 1 to 6 carbon atoms, $R^7$ and $R^8$ each independently represents hydrogen atom or an alkyl group having from 1 to 6 carbon atoms, Q presents a partial structure represented by the following formula

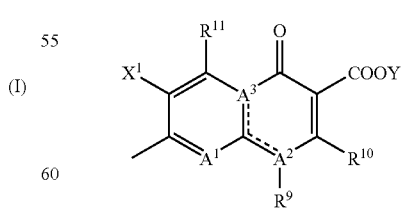

[wherein $R^9$ represents an alkyl group having from 1 to 6 carbon atoms, an alkenyl group having from 2 to 6 carbon atoms, a halogenoalkyl group having from 1 to 6 carbon atoms, a cyclic alkyl group having from 3 to 6 carbon atoms which may have a substituent, an aryl group which may have a substituent, a heteroaryl group which may have a substituent, an alkoxyl group having from 1 to 6 carbon atoms or an alkylamino group having from 1 to 6 carbon atoms, $R^{10}$ represents a hydrogen atom or an alkylthio group having 1 to 6 carbon atoms, wherein $R^{10}$ and the aforementioned $R^9$ may be integrated to form a ring structure by incorporating a part of the mother skeleton, and the thus formed ring may contain a sulfur atom as a ring-constituent atom, and the ring may also have an alkyl group having from 1 to 6 carbon atoms as a substituent, $R^{11}$ represents a hydrogen atom, an amino group a hydroxyl group, a thiol group, a halogenomethyl, an alkyl group having from 1 to 6 carbon atoms, an alkenyl group having from 2 to 6 carbon atoms, an alkynyl group having from 2 to 6 carbon atoms or an alkoxyl group having 1 to 6 carbon atoms, wherein the amino group may have one or two substituents selected from the group consisting of formyl group, an alkyl group having from 1 to 6 carbon atoms and an acyl group having from 2 to 6 carbon atoms, when $R^{11}$ is amino group, hydroxyl group or thiol group, they may be protected with a protective group, $X^1$ represents a halogen atom or hydrogen atom, $A^1$ represents nitrogen atom or a partial structure represented by a formula (II)

(II)

[wherein $X^2$ represents a hydrogen atom, an amino group, a halogen atom, a cyano group, a halogenomethyl group, a halogenomethoxyl group, an alkyl group having from 1 to 6 carbon atoms, an alkenyl group having from 2 to 6 carbon atoms, an alkynyl group having from 2 to 6 carbon atoms or an alkoxyl group having from 1 to 6 carbon atoms, wherein the amino group among them may have one or two substituents selected from the group consisting of formyl group, an alkyl group having from 1 to 6 carbon atoms and an acyl group having from 2 to 5 carbon atoms, and $X^2$ and the aforementioned $R^9$ may be integrated to form a ring structure by incorporating a part of the mother skeleton, and the thus formed ring may contain an oxygen atom, a nitrogen atom or a sulfur atom as a ring-constituent atom, and the ring may also have an alkyl group having from 1 to 6 carbon atoms as a substituent], $A^2$ and $A^3$ each independently represents a nitrogen atom or a carbon atom, and $A^2$ and $A^3$ and the carbon atom, to which they are bonded, form a partial structure

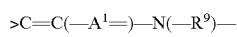

or a partial structure

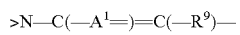

(wherein ">" means the presence of 2 bonds to the nitrogen atom or carbon atom, the same shall apply hereinafter), and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having from 1 to 6 carbon atoms, an alkoxymethyl group having from 2 to 7 carbon atoms or a phenylalkyl group (composed of an alkylene group having from 1 to 6 carbon atoms and a phenyl group)]}.

The invention also relates to a compound of the formula (I), its salts or hydrates thereof, wherein Q in the formula (I) has a structure represented by formula:

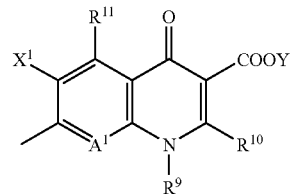

or formula:

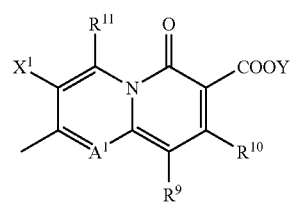

(wherein $A^1$, $R^9$, $R^{10}$, $R^{11}$, $X^1$ and Y are as defined in the foregoing); a compound of the formula (I), its salts or hydrates thereof, wherein Q in the formula (I) has a structure represented by formula:

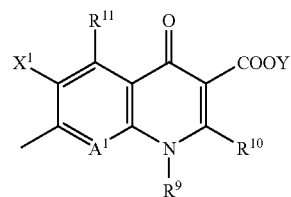

(wherein $A^1$, $R^9$, $R^{11}$, $X^1$ and Y are as defined in the foregoing); a compound of the formula (I), its salts or hydrates thereof, wherein Q in the formula (I) is 6-carboxy-9-fluoro-2,3-dihydro-3-(S)-methyl-7-oxo-7H-pyrido[1,2,3-de ] [1.4]benzoxazin-10-yl group; [this is represented by the following formula]:

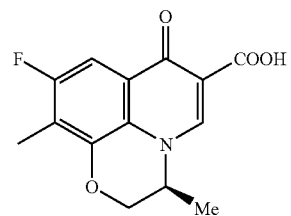

a compound of the formula (I), its salts or hydrates thereof, wherein Q in the formula (I) is 8-amino-6-carboxy-9- fluoro-2,3-dihydro-3-(S)-methyl-7-oxo-7H-pyrido[1,2,3-de][1.4]benzoxazin-10-yl group; [this is presented by the following formula]:

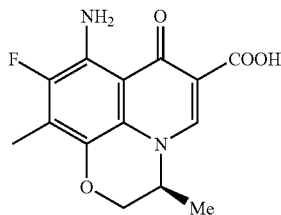

a compound of the formula (I), its salts or hydrates thereof, wherein Q in the formula (I) is 3-carboxy-6-fluoro-1-[2-(S)-fluoro-1-(R)-cyclopropyl]-1,4-dihydro-4-oxo-1,8-naphthyridin-7-yl group; [this is represented by the following formula]:

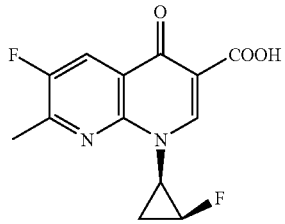

a compound of the formula (I), its salts or hydrates thereof, wherein Q in the formula (I) is 3-carboxy-8-chloro-6-fluoro-1-[2-(S)-fluoro-1-(R)-cyclopropyl]-1,4-dihydro-4-oxoquinolin-7-yl group; [this is represented by the following formula]:

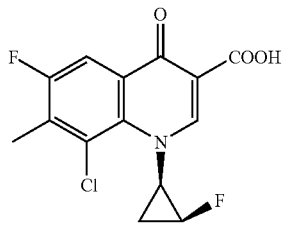

a compound of the formula (I), its salts or hydrates thereof, wherein Q in the formula (I) is 3-carboxy-6-fluoro-1-[2-(S)-fluoro-1-(R)-cyclopropyl]-8-methoxy-1,4-dihydro-4-oxoquinolin-7-yl group; [this is presented by the following formula]:

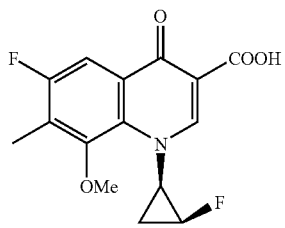

a compound of the formula (I), its salts or hydrates thereof, wherein Q in the formula (I) is 3-carboxy-1-[2-(S)-fluoro-1-(R)-cyclopropyl]-8-methoxy-1,4 dihydro-4-oxoquinolin-7-yl group; [this is represented by the following formula]:

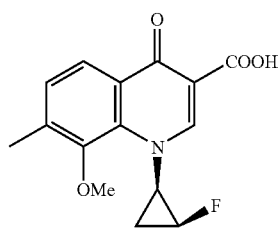

a compound of the formula (I), its salts or hydrates thereof, wherein Q in the formula (I) is 3-carboxy-6-fluoro-1-[2-(S)-fluoro-1-(R)-cyclopropyl]-8-difluoromethoxy-1,4-dihydro-4-oxoquinolin-7-yl group; [this is represented by the following formula]:

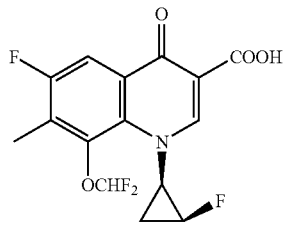

a compound of the formula (I), its salts or hydrates thereof, wherein Q in the formula (I) is 3-carboxy-1-[2-(S)-fluoro-1-(R)-cyclopropyl]-8-difluoromethoxy-1, 4 dihydro-4-oxoquinolin-7-yl group; [this is represented by the following formula]:

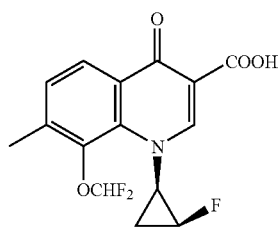

a compound of the formula (I), its salts or hydrates thereof, wherein Q in the formula (I) is 3-carboxy-6-fluoro-1-[2-(S)-fluoro-1-(R)-cyclopropyl]-8-methyl-1, 4-dihydro-4-oxoquinolin-7-yl group; [this is represented by the following formula]:

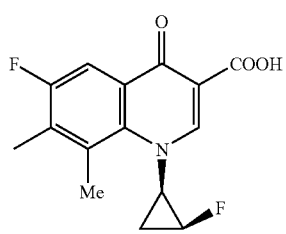

a compound of the formula (I), its salts or hydrates thereof, wherein Q in the formula (I) is 5-amino-3-carboxy-6-fluoro-1-[2-(S)-fluoro-1-(R)-cyclopropyl]-8-methoxy-1,4-dihydro-4-oxoquinolin-7-yl group; [this is represented by the following formula]:

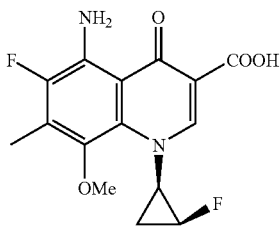

a compound of the formula (I), its salts or hydrates thereof, wherein Q in the formula (I) is 5-amino-3-carboxy-6-fluoro-1-[2-(S)-fluoro-1-(R)-cyclopropyl]-8-methyl-1,4-dihydro-4-oxoquinolin-7-yl group [this is represented by the following formula]:

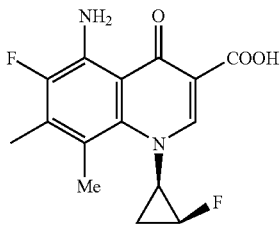

a compound of the formula (I), its salts or hydrates thereof, wherein Q in the formula (I) is 5-amino-3-carboxy-6,8-difluoro-1-[2-(S)-fluoro-1-(R)-cyclopropyl]-1,4-dihydro-4-oxoquinolin-7-yl group; [this is represented by the following formula]:

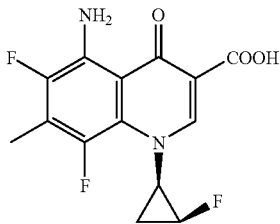

a compound of the formula (I), its salts or hydrates thereof, wherein $R^1$ in the formula (I) is an aryl group having from 6 to 10 carbon atom which may have a substituent;
a compound of the formula (I), its salts or hydrates thereof, wherein $R^1$ in the formula (I) is an aryl group having from 6 to 10 carbon atoms which may have a substituent, and its aryl group moiety is phenyl group or naphthyl group;
a compound of the formula (I), its salts or hydrates thereof, wherein $R^1$ in the formula (I) is a heteroaryl group which may have a substituent; a compound of the formula (I), its salt thereof or a hydrate thereof, wherein $R^1$ in the formula (I) is a heteroaryl group which may have a substituent, and its heteroaryl group moiety is furyl group, thienyl group, pyrrolyl group, oxazolyl group, isoxazolyl group, thiazolyl group, isothiazolyl, imidazolyl group, pyrazolyl group, furazanyl group, pyridyl group, pyrazinyl group, pyrimidyl group, pyridazinyl group, triazinyl group or tetrazinyl group,
a compound of the formula (I), its salts or hydrates thereof, wherein the compound of formula (I) is a stereochemically pure compound;
a compound of the formula (I), its salts or hydrates thereof, wherein $R^9$ is a cyclopropyl group having a halogen atom as a substituent;
a compound of the formula (I), its salts or hydrates thereof, wherein the cyclopropyl group having a halogen atom as a substituent is a 1,2-cis-halogenocyclopropyl group;
a compound of the formula (I), its salts or hydrates thereof, wherein the cyclopropyl group having a halogen atom as a substituent is a stereochemically pure substituent;
a compound of the formula (I), its salts or hydrates thereof, wherein the cyclopropyl group having a halogen atom as a substituent is a (1R, 2S)-2-halogenocyclopropyl group;
a compound of the formula (I), its salts or hydrates thereof, wherein halogen atom of the cyclopropyl group having a halogen atom as a substituent is fluorine atom;
a compound of the formula (I), its salts or hydrates thereof, wherein each of $R^4$, $R^5$, $R^6$, $R^7$ and $R^8$ in the formula (I) is hydrogen atom;
a compound of the formula (I), its salts or hydrates thereof, wherein $R^1$ in the formula (I) is an aryl group having from 6 to 10 carbon atoms which may have a substituent or a heteroaryl group of five-membered ring or six-membered ring which contains from 1 to 4 hetero atoms optionally selected from nitrogen atom, oxygen atom and sulfur atom and may have a substituent;
a compound of the formula (I), its salts or hydrates thereof, wherein $R^1$ is phenyl group or naphthyl group;
a compound of the formula (I), its salts or hydrates thereof, wherein $R^1$ is furyl group thienyl group pyrrolyl group, oxazolyl group isoxazolyl group, thiazolyl group isothiazolyl group, imidazolyl group, pyrazolyl group, furazanyl group, pyridyl group, pyrazinyl group, pyrimidyl group, pyridazinyl group, triazinyl group or tetrazinyl group;
a medicament which comprises a compound of formula (I), its salts or hydrates thereof as an active ingredient;
an antibacterial agent which comprises a compound of formula (I), its salts or hydrates thereof as an active ingredient;
a therapeutic agent for an infectious disease, which comprises a compound of formula (I), its salts or hydrates thereof as an active ingredient;
a method for treating a disease, which comprises administering a compound of formula (I), its salts or hydrates thereof;
a method for treating an infectious disease, which comprises administering a compound of formula (I), its salts or hydrates thereof;
a method for producing a medicament, which comprises formulating a compound of formula (I), its salts or hydrates thereof as an active ingredient;
a method for producing an antibacterial agent, which comprises formulating a compound of formula (I), its salts or hydrates thereof as an active ingredient;
a method for producing an infectious disease treating agent, which comprises formulating a compound of formula (I), its salts or hydrates thereof as an active, ingredient;
use of a compound of formula (I), its salts or hydrates thereof in producing a medicament;
use of a compound of formula (I), its salts or hydrates thereof in producing an antibacterial agent;

use of a compound of formula (I), its salts or hydrates thereof in producing an infectious disease treating agent; and so on.

The invention also relates to each of the following items. That is, a compound represented by the following formula, its salts and hydrates thereof

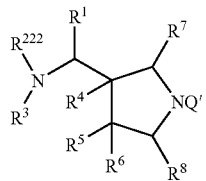

[wherein $R^1$ represents an aryl group having form 6 to 10 carbon atoms or a heteroaryl group, wherein the heteroaryl group may be a five-membered ring or a six-membered ring and may contain from 1 to 4 hetero atoms optionally selected from nitrogen atom, oxygen atom and sulfur atom, wherein these aryl group and heteroaryl group may have one or more substituents selected from the group consisting of a halogen atom, hydroxyl group, thiol group, amino group, nitro group, cyano group, carboxyl group, carbamoyl group, phenyl group, an alkyl group having from 1 to 6 carbon atoms, an alkoxyl group having from 1 to 6 carbon atoms, an alkylthio group having from 1 to 6 carbon atoms, an alkoxycarbonyl group having from 2 to 6 carbon atoms, an acyl group having from 2 to 5 carbon atoms and a heteroaryl group (this heteroaryl group may be a five-membered ring or a six-membered ring and contain from 1 to 4 hetero atoms optionally selected from nitrogen atom, oxygen atom and sulfur atom), wherein the alkyl group, alkoxyl group, alkylthio group, alkoxycarbonyl group, acyl group, phenyl group and heteroaryl group among then may have one or more substituents selected from the group consisting of a halogen atom, hydroxyl group, an alkoxyl group having from 1 to 6 carbon atoms and an alkylthio group having from 1 to 6 carbon atoms, and the amino group may have one or two substituents selected from the group consisting of formyl group, an alkyl group having from 1 to 6 carbon atoms, an acyl group having from 2 to 5 carbon atoms and an alkoxycarbonyl group having from 2 to 5 carbon atoms, $R^{222}$ represents hydrogen atom, an alkyl group having from 1 to 6 carbon atoms or a protective group of an amino group, $R^3$ represents hydrogen atom or an alkyl group having from 1 to 6 carbon atoms, wherein the alkyl group of $R^{222}$ and $R^3$ may have one or more substituents selected from the group consisting of hydroxyl group, a halogen atom, an alkylthio group having from 1 to 6 carbon atoms and an alkoxyl group having from 1 to 6 carbon atoms, $R^4$, $R^5$ and $R^6$ each independently represents hydrogen atom, hydroxyl group, a halogen atom, carbamoyl group, an alkyl group having from 1 to 6 carbon atom, an alkoxyl group having from 1 to 6 carbon atoms or an alkylthio group having from 1 to 6 carbon atoms, wherein the alkyl group among them may have one or more substituents selected from the group consisting of hydroxyl group, a halogen atom and an alkoxyl group having from 1 to 6 carbon atoms, $R^7$ and $R^8$ each independently represents hydrogen atom or an alkyl group having from 1 to 6 carbon atoms, and Q' represents a protective group of an amino group];

the compound of the above formula, its salts or hydrates thereof, wherein the protective group of an amino group is a protective group selected from group consisting of an alkoxycarbonyl group which may have a substituent, an aralkyloxycarbonyl group which may have a substituent, an acyl group which may have a substituent, an alkyl group which may have a substituent, an aralkyl group which may have a substituent and substituted silyl groups;

the compound of the above formula, its salts or hydrates thereof, wherein the protective group of an amino group is a protective group selected from the group consisting of tert-butoxycarbonyl group, 2,2,2-trichloroethoxycarbonyl group and the like alkoxycarbonyl groups; benzyloxycarbonyl group, para-methoxybenzyloxycarbonyl group, para-nitrobenzyloxycarbonyl group and the like aralkyloxycarbonyl groups; acetyl group, methoxyacetyl group, trifluoroacetyl group, chloroacetyl group, pivaloyl group, formyl group, benzoyl group and the like acyl groups; tert-butyl group, benzyl group, para-nitrobenzyl group, para-methoxybenzyl group, triphenylmethyl group and the like alkyl groups or aralkyl groups; methoxymethyl group, tert-butoxymethyl group, tetrahydropyranyl group, 2,2,2-trichloroethoxymethyl group and the like ethers; and trimethylsilyl group, isopropyldimethylsilyl group, tert-butyldimethylsilyl group, tribenzylsilyl group, tert-butyldiphenylsilyl group and the like substituted silyl groups;

the compound of the above formula, its salts or hydrates thereof, wherein $R^{222}$ and Q' are not the same;

the compound of the above formula, its salts or hydrates thereof, wherein $R^1$ is an aryl group having from 6 to 10 carbon atoms which may have a substituent;

the compound of the above formula, its salts or hydrates thereof, wherein $R^1$ is an aryl group having from 6 to 10 carbon atoms which may have a substituent, and its aryl group moiety is phenyl group or naphthyl group;

the compound of the above formula, its salts or hydrates thereof, wherein $R^1$ is a heteroaryl group which may have a substituent;

the compound of the above formula, its salts or hydrates thereof, wherein $R^1$ is a heteroaryl group which may have a substituent, and its heteroaryl group moiety is furyl group, thienyl group, pyrrolyl group, oxazolyl group, isoxazolyl group, thiazolyl group, isothiazolyl group, imidazolyl group, pyrazolyl group, furazanyl group, pyridyl group, pyrazinyl group, pyrimidyl group, pyridazinyl group, triazinyl group or tetrazinyl group;

the compound of the above formula, its salts or hydrates thereof, wherein the each of $R^4$, $R^5$, $R^6$, $R^7$ and $R^8$ is hydrogen atom; and so on.

The invention also relates to each of the following items. That is, a compound represented by the following formula, its salts and hydrates thereof

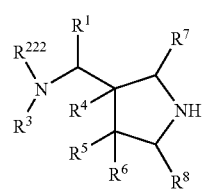

[wherein $R^1$ represents an aryl group having from 6 to 10 carbon atoms or a heteroaryl group, wherein the heteroaryl group may be a five-membered ring or a six membered ring and may contain from 1 to 4 hetero atoms optionally selected from nitrogen atom, oxygen atom and sulfur atom, wherein these aryl group and heteroaryl group may have one or more substituents selected from the group consisting of a halogen atom, hydroxyl group, thiol group, amino group, nitro group, cyano group, carboxyl group, carbamoyl group, phenyl group, an alkyl group having from 1 to 6 carbon atoms, an alkoxyl group having from 1 to 6 carbon atoms, an alkylthio group having from 1 to 6 carbon atoms, an alkoxycarbonyl group having from 2 to 6 carbon atoms, an acyl group having from 2 to 5 carbon atoms and a heteroaryl group (this heteroaryl group may be a five-membered ring or a six-membered ring and contain from 1 to 4 hetero atoms optionally selected from nitrogen atom, oxygen atom and atom)

wherein the alkyl group, alkoxyl group, alkylthio group, alkoxycarbonyl group, acyl group, phenyl group and heteroaryl group among them may have one or more substituents selected from the group consisting of a halogen atom, hydroxyl group, an alkoxyl group having from 1 to 6 carbon atoms and an alkylthio group having from 1 to 6 carbon atoms, the amino group may have one or two substituents selected from the group consisting of formyl group, an alkyl group having from 1 to 6 carbon atoms, an acyl group having from 2 to 5 carbon atoms and an alkoxycarbonyl group having from 2 to 5 carbon atoms, $R^{222}$ represents hydrogen atom, an alkyl group having from 1 to 6 carbon atoms or a protective group of an amino group, $R^3$ represents hydrogen atom or an alkyl group having from 1 to 6 carbon atoms, wherein the alkyl group of $R^{222}$ and $R^3$ may have one or more substituents selected from the group consisting of hydroxyl group, a halogen atom, an alkylthio group having from 1 to 6 carbon atoms and an alkoxyl group having from 1 to 6 carbon atoms, $R^4$, $R^5$ and $R^6$ each independently represents hydrogen atom, hydroxyl group, a halogen atom, arbamoyl group, an alkyl group having from 1 to 6 carbon atoms, an alkoxyl group having from 1 to 6 carbon atoms or an alkylthio group having from 1 to 6 carbon atoms, wherein the alkyl group among them may have one or more substituents selected from the group consisting of hydroxyl group, a halogen atom and an alkoxyl group having from 1 to 6 carbon atoms, and $R^7$ and $R^8$ each independently represents hydrogen atom or an alkyl group having from 1 to 6 carbon atoms];

the compound of the above formula, its salts or hydrates thereof, wherein the protective group of an amino group is a protective group selected from group consisting of an alkoxycarbonyl group which may have a substituent, an aralkyloxycarbonyl group which may have a substituent, an acyl group which may have a substituent, an alkyl group which may have a substituent, an aralkyl group which may have a substituent and substituted silyl groups;

the compound of the above formula, its salts or hydrates thereof, wherein the protective group of an amino group is a protective group selected from the group consisting of tert-butoxycarbonyl group, 2,2,2-trichloroethoxycarbonyl group and the like alkoxycarbonyl groups; benzyloxycarbonyl group, para-methoxybenzyloxycarbonyl group, para-nitrobenzyloxycarbonyl group and the like aralkyloxycanyl groups; acetyl group, methoxyacetyl group, trifluoroacetyl group, chloroacetyl group, pivaloyl group, formyl group, benzoyl group and the like acyl groups; tert-butyl group, benzyl group, para-nitrobenzyl group, para-methoxybenzyl group, triphenylmethyl group and the like alkyl groups or aralkyl groups; methoxymethyl group, tert-butoxymethyl group, tetrahydropyranyl group, 2,2,2-trichloroethoxymethyl group and the like ethers; and triethylsilyl group, isopropyldimethylsilyl group, tert-butyldimethylsilyl group, tribenzylsilyl group, tert-butyldiphenylsilyl group and the like silyl groups;

the compound of the above formula, its salts or hydrates thereof, wherein $R^1$ is an aryl group having from 6 to 10 carbon atoms which may have a substituent;

the compound of the above formula, its salts or hydrates thereof, wherein $R^1$ is an aryl group having from 6 to 10 carbon atoms which may have a substituent, and its aryl group moiety is phenyl group or naphthyl group;

the compound of the above formula, its salts or hydrates thereof, wherein $R^1$ is a heteroaryl group which may have a substituent;

the compound of the above formula, its salts or hydrates thereof, wherein $R^1$ is a heteroaryl group which may have a substituent, and its heteroaryl group moiety is furyl group thienyl group, pyrrolyl group, oxazolyl group, isoxazolyl group thiazolyl group, isothiazolyl group imidazolyl group, pyrazolyl group, furazanyl group, pyridyl group pyrazinyl group, pyrimidyl group pyridazinyl group, triazinyl group or tetrazinyl group the compound of the above formula, its salts or hydrates thereof, wherein the each of $R^4$, $R^5$, $R^6$, $R^7$ and $R^8$ is hydrogen atom;

and so on.

The invention also relates to a method for producing a quinolone compound, which comprises removing Q' from a compound presented by the following formula, its salts and hydrates thereof

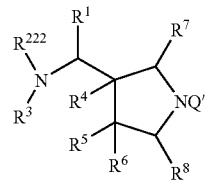

[wherein $R^1$ represents an aryl group having from 6 to 10 carbon atoms or a heteroaryl group, wherein the heteroaryl group may be a five-membered ring or a six-membered ring and may contain from 1 to 4 hetero atoms optionally selected from nitrogen atom, oxygen atom and sulfur atom, wherein these aryl group and heteroaryl group may have one or more substituents selected from the group consisting of a halogen atom, hydroxyl group, thiol group, amino group, nitro group, cyano group, carboxyl group, carbamoyl group, phenyl group, an alkyl group having from 1 to 6 carbon atoms, an alkoxyl group having from 1 to 6 carbon atoms, an alkylthio group having from 1 to 6 carbon atoms, an alkoxycarbonyl group having from 2 to 6 carbon atoms, an acyl group having from 2 to 5 carbon atoms and a heteroaryl group (this heteroaryl group may be a five ed ring or a six-membered ring and contain from 1 to 4 hetero atoms optionally selected from nitrogen atom, oxygen atom and sulfur atom), wherein the alkyl group, alkoxyl group, alkylthio group, alkoxycarbonyl group, acyl group, phenyl group and heteroaryl group among them may have one or more substituents selected from the group consisting of a halogen atom, hydroxyl group, an alkoxyl group having from 1 to 6 carbon atoms and an alkylthio group having from 1 to 6 carbon atoms, the amino group may have one or two substituents selected from the group consisting of formyl group, an alkyl group having from 1 to 6 carbon atoms, an acyl group having from 2 to 5 carbon atoms and an alkoxycarbonyl group having from 2 to 5 carbon atoms, $R^{222}$ represents hydrogen atom, an alkyl group having from 1 to 6 carbon atoms or a protective group of an amino group, $R^3$ represents hydrogen atom or an alkyl group having from 1 to 6 carbon atoms, wherein the alkyl group of $R^{222}$ and $R^3$ may have one or more substituents selected from the group consisting of hydroxyl group, a halogen atom, an alkylthio group having from 1 to 6 carbon atoms and an alkoxyl group having from 1 to 6 carbon atoms, $R^4$, $R^5$ and $R^6$ each independently represents hydrogen atom, hydroxyl group, a halogen atom, carbamoyl group, an alkyl group having from 1 to 6 carbon atoms, an alkoxyl group having from 1 to 6 carbon atoms or an alkylthio group having from 1 to 6 carbon atoms, wherein the alkyl group among them may have one or more substituents selected from the group consisting of hydroxyl group, a halogen atom and an alkoxyl group having from 1 to 6 carbon atoms, $R^7$ and $R^8$ each independently represents hydrogen atom or an alkyl group having from 1 to 6 carbon atoms, and Q' represents a protective group of an amino group], if necessary, isolating and purifying, and then allowing it to react with a compound of formula (III):

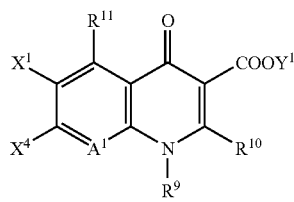

[wherein $X^1$ represents a halogen atom or hydrogen atom, $X^4$ represents a substituent having a function as a leaving group such as fluorine atom, chlorine atom, bromine atom, a substituted or unsubstituted phenylsulfonyl group or a substituted or unsubstituted alkylsulfonyl group having from 1 to 3 carbon atoms, $Y^1$ represents hydrogen atom, phenyl group, acetoxymethyl group, pivaloyloxymethyl group, ethoxycarbonyl group, choline group, dimethylaminoethyl group, 5-indanyl group, phthalidinyl group, 5-alkyl-2-oxo-1,3-dioxol-4-yl-methyl group, 3-acetoxy-2-oxobutyl group, an alkyl group having from 1 to 6 carbon atoms, an alkoxymethyl group having form 2 to 7 carbon atom or a phenylalkyl group (composed of an alkylene group having form 1 to 6 carbon atoms and phenyl group), or a boron-containing substituent represented by formula (IV):

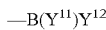 (IV)

(wherein each of $Y^{11}$ and $Y^{12}$ represents fluorine atom or an alkylcarbonyloxy group having from 2 to 4 carbon atoms), $R^9$ represents an alkyl group having form 1 to 6 carbon atoms, an alkenyl group having from 2 to 6 carbon atoms, a halogenoalkyl group having from 1 to 6 carbon atoms, a cyclic alkyl group having from 3 to 6 carbon atoms which may have a substituent, an aryl group which may have a substituent, a heteroaryl group which may have a substituent, an alkoxyl group having from 1 to 6 carbon atoms or an alkylamino group having from 1 to 6 carbon atoms, $R^{10}$ represents hydrogen atom or an alkylthio group having 1 to 6 carbon atoms, wherein $R^{10}$ and the aforementioned $R^9$ may be integrated to form a ring structure by incorporating a part of the mother skeleton, and the thus formed ring may contain a sulfur atom as a ring-constituent atom, and the ring may also have an alkyl group having from 1 to 6 carbon atoms as a substituent, $R^{11}$ represents hydrogen atom, amino group, hydroxyl group, thiol group, a halogenomethyl group, an alkyl group having from 1 to 6 carbon atoms, an alkenyl group having from 2 to 6 carbon atoms, an alkynyl group having form 2 to 6 carbon atoms or an alkoxyl group having 1 to 6 carbon atoms, wherein the amino group may have one or two substituents selected from the group consisting of formyl group, an alkyl group having from 1 to 6 carbon atoms and an acyl group having from 2 to 6 carbon atoms, when $R^{11}$ is amino group, hydroxyl group or thiol group, they may be protected with a protective group, $A^1$ represents nitrogen atom or a partial structure represented by formula (II):

[wherein $X^2$ represents hydrogen atom, amino group, a halogen atom, cyano group, a halogenomethyl group, a halogenomethoxyl group, an alkyl group having from 1 to 6 carbon atoms, an alkenyl group having from 2 to 6 carbon atoms, an alkynyl group having from 2 to 6 carbon atoms or an alkoxyl group having from 1 to 6 carbon atoms, wherein the amino group among them may have one or two substituents selected from the group consisting of formyl group, an alkyl group having from 1 to 6 carbon atoms and an acyl group having from 2 to 5 carbon atoms, and $X^2$ and the aforementioned $R^9$ may be integrated to form a ring structure by incorporating a part of the mother skeleton, and the thus formed ring may contain an oxygen atom, a nitrogen atom or a sulfur atom as a ring-constituent atom, and the ring may also have an alkyl group having from 1 to 6 con atoms as a substituent)], or with a compound represented by formula (V):

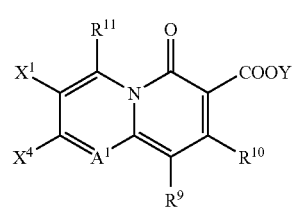

(wherein $X^1$, $X^4$, $R^9$, $R^{10}$, $R^{11}$, $A^1$ and Y are as defined in the foregoing), in the presence of a base and further carrying out deprotection if necessary.

The invention also relates to a method for producing a quinolone compound, which comprises allowing a compound represented by the following formula, its salts and hydrates thereof

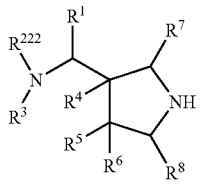

(wherein $R^1$ represents an aryl group having from 6 to 10 carbon atoms or a heteroaryl group, wherein the heteroaryl group may be a five-membered ring or a six-membered ring and may contain from 1 to 4 hetero atoms optionally selected from nitrogen atom, oxygen atom and sulfur atom, wherein these aryl group and heteroaryl group may have one or more substituents selected form the group consisting of a halogen atom, hydroxyl group, thiol group, amino group, nitro group, cyano group, carboxyl group, carbamoyl group, phenyl group, an alkyl group having from 1 to 6 carbon atoms, an alkoxyl group having from 1 to 6 carbon atoms, an alkylthio group having from 1 to 6 carbon atoms, an alkoxycarbonyl group having from 2 to 6 carbon atoms, an acyl group having from 2 to 5 carbon atoms and a heteroaryl group (the heteroaryl group may be a five-membered ring or a six-membered ring and contain from 1 to 4 hetero atoms optionally selected from nitrogen atom, oxygen atom and sulfur atom), wherein the alkyl group, alkoxyl group, alkylthio group, alkoxycarbonyl group, acyl group, phenyl group and heteroaryl group among them may have one or more substituents selected from the group consisting of a halogen atom, hydroxyl group, an alkoxyl group having from 1 to 6 carbon atoms and an alkylthio group having from 1 to 6 carbon atoms, the amino group may have one or two substituents selected from the group consisting of formyl group, an alkyl group having from 1 to 6 carbon atoms, an acyl group having from 2 to 5 carbon atoms and an alkoxycarbonyl group having from 2 to 5 carbon atoms, $R^{222}$ represents hydrogen atom, an alkyl group having from 1 to 6 carbon atoms or a protective group of an amino group, $R^3$ represents hydrogen atom or an alkyl group having from 1 to 6 carbon atoms, wherein the alkyl group of $R^{222}$ and $R^3$ may have one or more substituents selected from the group consisting of hydroxyl group, a halogen atom, an alkylthio group having from 1 to 6 carbon atoms and an alkoxyl group having from 1 to 6 carbon atoms, $R^4$, $R^5$ and $R^6$ each independently represents hydrogen atom, hydroxyl group, a halogen atom, carbamoyl group, an alkyl group having from 1 to 6 carbon atoms, an alkoxyl group having from 1 to 6 carbon atoms or an alkylthio group having from 1 to 6 carbon atoms, wherein the alkyl group among them may have one or more substituents selected from the group consisting of hydroxyl group, a halogen atom and an alkoxyl group having from 1 to 6 carbon atoms, and $R^7$ and $R^8$ each independently represents hydrogen atom or an alkyl group having from 1 to 6 carbon atoms) to react with a compound represented by formula (III):

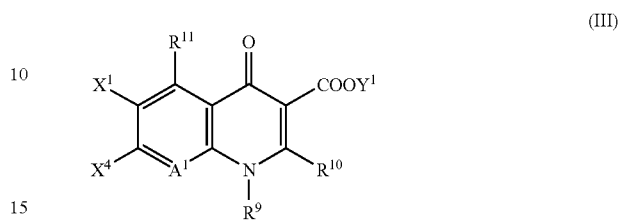

[wherein $X^1$ resents a halogen atom or hydrogen atom, $X^4$ represents a substituent having a function as a leaving group, such as fluorine atom, chlorine atom, bromine atom, a substituted or unsubstituted phenylsulfonyl group or a substituted or unsubstituted alkylsulfonyl group having from 1 to 3 carbon atoms, $Y^1$ represents hydrogen atom, phenyl group, acetoxymethyl group, pivaloyloxymethyl group, ethoxycarbonyl group, choline group, dimethylaminoethyl group, 5-indanyl group, phthalidinyl group, 5-alkyl-2-oxo-1,3-dioxol-4-yl-methyl group, 3-acetoxy-2-oxobutyl group, an alkyl group having from 1 to 6 carbon atoms, an alkoxymethyl group having from 2 to 7 carbon atoms or a phenylalkyl group composed of an alkylene group having from 1 to 6 carbon atoms and phenyl group, or a boron-containing substituent represented by formula (IV):

$$-B(Y^{11})Y^{12} \qquad (IV)$$

(wherein each of $Y^{11}$ and $Y^{12}$ represents fluorine atom or an alkylcarbonyloxy group having from 2 to 4 carbon atoms), $R^9$ represents an alkyl group having form 1 to 6 carbon atoms, an alkenyl group having from 2 to 6 carbon atoms, a halogenoalkyl group having from 1 to 6 carbon atoms, a cyclic alkyl group having from 3 to 6 carbon atoms which may have a substituent, an aryl group which may have a substituent, a heteroaryl group which may have a substituent, an alkoxyl group having from 1 to 6 carbon atoms or an alkylamino group having from 1 to 6 carbon atoms, $R^{10}$ represents hydrogen atom or an alkylthio group having 1 to 6 carbon atoms, wherein $R^{10}$ and the aforementioned $R^9$ may be integrated to form a ring structure by incorporating a part of the mother skeleton, and the thus formed ring may contain sulfur atom as a ring-constituent atom, and the ring may also have an alkyl group having from 1 to 6 carbon atoms as a substituent, $R^{11}$ represents hydrogen atom, amino group, hydroxyl group, thiol group, a halogenomethyl group, an alkyl group having from 1 to 6 carbon atoms, an alkenyl group having from 2 to 6 carbon atoms, an alkynyl group having from 2 to 6 carbon atoms or an alkoxyl group having 1 to 6 carbon atoms, wherein the amino group may have one or two substituents selected from the group consisting of formyl group, an alkyl group having from 1 to 6 carbon atoms and an acyl group having from 2 to 6 carbon atoms, when $R^{11}$ is amino group, hydroxyl group or thiol group, they may be protected with a protective group, $A^1$ represents nitrogen atom or a partial structure represented by formula (II):

(II)

(wherein $X^2$ represents hydrogen atom, amino group, a halogen atom, cyano group, a halogenomethyl group, a halogenomethoxyl group, an alkyl group having from 1 to 6 carbon atoms, an alkenyl group having from 2 to 6 carbon atoms, an alkynyl group having from 2 to 6 carbon atoms or an alkoxyl group having from 1 to 6 carbon atoms, wherein the amino group among them may have one or two substituents selected from the group consisting of formyl group, an alkyl group having from 1 to 6 carbon atoms and an acyl group having from 2 to 5 carbon atoms, and $X^2$ and the aforementioned $R^9$ may be integrated to form a ring structure by incorporating a part of the mother skeleton, and the thus formed ring may contain oxygen atom, nitrogen atom or sulfur atom as a ring-constituent atom, and the ring may also have an alkyl group having from 1 to 6 carbon atoms as a substituent)], or with a compound presented by formula (V):

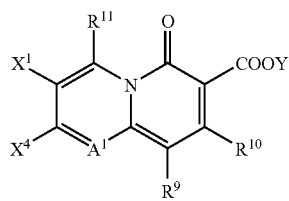

(V)

(wherein $X^1$, $X^4$, $R^9$, $R^{10}$, $R^{11}$, $A^1$ and Y are as defined in the foregoing), in the presence of a base and further carrying out deprotection as occasion demands.

(Mode for Carrying Out the Invention)

The substituents of the compound of the invention represented by formula (I) are described.

The substituents $R^1$ is an aromatic group (an aromatic substituent).

The compound of the invention is characterized in that an aromatic substituent is present at this position. This aromatic substituent may be either a hydrocarbon group (an aryl group) or a heterocyclic group (a heteroaryl group). In the case of a hydrocarbon group, it may be either monocyclic or bicyclic. In the case of a heterocyclic group, it may also be either monocyclic or bicyclic. In the case of a monocyclic heterocyclic group, it is a five-membered ring or six-membered ring, and in the case of a bicyclic heterocyclic group, it is a benzo-fused ring system or other than that and a 6-5 fused ring system or a 6-6 fused ring system can be exemplified. Also, in the case of the heterocyclic system, the hetero atom to be contained is from 1 to 4 optionally selected from nitrogen atom, oxygen atom and sulfur atom.

That is, the substituent $R^1$ is an aromatic substituent such as an aryl group having from 6 to 10 carbon atoms or a heteroaryl group.

In this case, the heteroaryl group is a five-membered ring or a six-membered ring and may contain from 1 to 4 hetero atoms optionally selected from nitrogen atom, oxygen atom and sulfur atom.

These aryl group and heteroaryl group may have one or more substituents selected from the group consisting of a halogen atom, hydroxyl group, thiol group, amino group, nitro group, cyano group, carboxyl group, carbamoyl group, phenyl group, an alkyl group having from 1 to 6 carbon atoms, an alkoxyl group having from 1 to 6 carbon atoms, an alkylthio group having from 1 to 6 carbon atoms, an alkoxycarbonyl group having from 2 to 6 carbon atoms, an acyl group having from 2 to 5 carbon atoms and a heteroaryl group (a five-membered ring or a six-membered ring, which contains from 1 to 4 hetero atoms optionally selected from nitrogen atom, oxygen atom and sulfur atom).

The alkyl group, alkoxyl group, alkylthio group, alkoxycarbonyl group, acyl group, phenyl group and heteroaryl group as substituents on the aryl group or heteroaryl group may have one or more substituents selected from the group consisting of a halogen atom, hydroxyl an alkoxyl group having from 1 to 6 carbon atoms and an alkylthio group having from 1 to 6 carbon atoms.

Also, the amino group may have one or two substituents selected from the group consisting of formyl group, an alkyl group having from 1 to 6 carbon atoms, an acyl group having from 2 to 5 carbon atoms and an alkoxycarbonyl group having from 2 to 5 carbon atoms.

As the aryl group having from 6 to 10 carbon atoms as the aromatic substituent, phenyl group, pentalenyl group, naphthyl group, azulenyl group and the like can be exemplified, of which phenyl group, 1-naphthyl group and 2-naphthyl group are preferred.

As the heteroaryl group of a five ring or a six-membered ring which contains from 1 to 4 hetero atoms optionally selected from nitrogen atom, oxygen atom and sulfur atom, as the aromatic substituent, furyl group, thienyl group, pyrrolyl group, oxazolyl group, isoxazolyl group, thiazolyl group, isothiazolyl group, imidazolyl group, pyrazolyl group, furazanyl group, pyridyl group, pyrazinyl group, pyrimidyl group, pyridazinyl group, triazinyl group, tetrazinyl group and the like can be exemplified. Preferred among them include 2-furyl group, 3-furyl group, 2-thienyl group, 3-thienyl group, 2-oxazolyl group, 2-thiazolyl group, 2-imidazolyl group, 2-pyridyl group, 3-pyridyl group, 4-pyridyl group, 2 pyrazinyl group, 2-pyrimidyl group, 4-pyrimidyl group, 5-pyrimidyl group and 3-pyridazinyl group. As more preferred examples, 2-furyl group, 3-furyl group, 2-thienyl group, 2-oxazolyl group, 2-thiazolyl group, 2-imidazolyl group, 2-pyridyl group and 4-pyridyl group can be cited.

The substituent on the rings of these aryl group and heteroaryl group may be selected from the group consisting of a halogen atom, hydroxyl group, thiol group, amino group, nitro group, cyano group, carboxyl group, carbamoyl group, phenyl group, an alkyl group having from 1 to 6 carbon atoms, an alkoxyl group having from 1 to 6 carbon atoms, an alkylthio group having from 1 to 6 carbon atoms, an alkoxycarbonyl group having from 2 to 6 carbon atoms, an acyl group having from 2 to 5 carbon atoms and a heteroaryl group (this heteroaryl group is a five-membered ring or a six-membered ring, which contains from 1 to 4 hetero atoms optionally selected from nitrogen atom, oxygen atom and sulfur atom). Among these groups, an alkyl group, an alkoxyl group, an alkylthio group, a halogen atom, hydroxyl group, amino group, carbamoyl group, an alkoxycarbonyl group and phenyl group are preferred, and an alkyl group, an alkoxyl group, an alkylthio group, a halogen atom, hydroxyl group and amino group are particularly preferred substituents.

The substituted aryl group and substituted heteroaryl group as a case in which an alkyl group, an alkoxyl group, an alkylthio group, a halogen atom, hydroxyl group and amino group are preferred as the substituents on the ring of the aryl group and heteroaryl group are described.

When the aryl group and heteroaryl group have an alkyl group as a substituent, the alkyl group may be either straight or branched group having from 1 to 6 carbon atoms, and its preferred examples include methyl group, ethyl group, normal propyl group and isopropyl group When the alkyl group has a halogen atom as a substituent, the alkyl group may be either straight or branched form having from 1 to 6 carbon atoms, and fluorine atom is desirable as the substituting halogen atom. With regard to the number of fluorine atoms, it may be any one of from mono-substitution to perfluoro substitution. Its examples include monofluoromethyl group, difluoromethyl group, trifluoromethyl group, 2,2,2-trifluoroethyl group and the like.

When the alkyl group further has hydroxyl group as a substituent, the alkyl group may be either straight or branched form having from 1 to 6 carbon atoms. Though the substituting position of hydroxyl group is not particularly limited, it may preferably be substituted on the terminal carbon atom of the alkyl group. As the alkyl group having hydroxyl group, those which have up to 3 carbon atoms are desirable, and hydroxymethyl group, 2-hydroxyethyl group, 2-hydroxypropyl group, 3-hydroxypropyl group and the like are preferable.

When the alkyl group further has an alkoxyl group as a substituent, the alkyl group may be either straight or branched form having from 1 to 6 carbon atoms, and the substituting alkoxyl group may also be either straight or branched form having from 1 to 6 carbon atoms. Though the substituting position of alkoxyl group is not particularly limited, it may preferably be substituted on the terminal carbon atom of the alkyl group. An alkoxymethyl group, an alkoxyethyl group and an alkoxypropyl group are desirable as the alkyl group having an alkoxyl group, and the alkoxyl group may preferably have up to 3 carbon atoms. More preferred examples include methoxymethyl group, ethoxymethyl group and methoxyethyl group.

When the alkyl group further has an alkylthio group as a substituent, the alkyl group may be either straight or branched form having from 1 to 6 carbon atoms, and the substituting alkylthio group may also be either straight or branched form having from 1 to 6 carbon atoms. Though the substituting position of alkylthio group is not particularly limited, it may preferably be substituted on the terminal carbon atom of the alkyl group. An alkylthiomethyl group, an alkylthioethyl group and an alkylthioproyl group are desirable as the alkyl group having an alkylthio group, and the alkylthio group may preferably have from 1 to 3 carbon atoms. More preferred examples include methylthiomethyl group, ethylthiomethyl group and methylthioethyl group.

In the aforementioned aryl group and heteroaryl group having an "alkyl group which may have a substituent" as a substituent, the number of the alkyl groups may be any one of from mono-substitution to peralkyl substitution. When two or more alkyl groups are present, they may be the same or different from one another. As the alkyl substitution, mono-, di- or tri-substitution is suitable.

When the aryl group and heteroaryl group have an alkoxyl group as a substituent, this alkoxyl group maybe either straight or branched group having from 1 to 6 carbon atoms, and its preferred examples include methoxy group and ethoxy group.

When the alkoxyl group further has a halogen atom as a substituent, the alkoxyl group may be either straight or branched form having from 1 to 6 carbon atoms, and fluorine atom is desirable as the substituting halogen atom. With regard to the number of fluorine atoms, it may be any one of from mono-substitution to perfluoro substitution. Its examples include monofluoromethoxyl group, difluoramethoxyl group, trifluoromethoxyl group, 2,2,2-trifluoroethyl group and the like.

When the alkoxyl group further has hydroxyl group as a substituent, the alkoxyl group may be either straight or branched form having from 1 to 6 carbon atoms. Though the substituting position of hydroxyl group is not particularly limited, it may preferably be substituted on the terminal carbon atom of the alkoxyl group. As the alkoxyl group having hydroxyl group, those which have up to 3 carbon atoms are desirable, and 1-hydroxyethoxyl group, 2-hydroxyethoxyl group, 2-hydroxypropoxyl group, 3-hydroxypropoxyl group and the like are preferable.

When the alkoxyl group further has an alkoxyl group as a substituent, the alkoxyl group maybe either straight or branched form having from 1 to 6 carbon atoms, and the substituting alkoxyl group may also be either straight or branched form having from 1 to 6 carbon atoms. Though the substituting position of alkoxyl group is not particularly limited, it may preferably be substituted on the terminal carbon atom of the alkoxyl group. An alkoxymethyl group, an alkoxyethoxyl group is desirable as the alkoxyl group having an alkoxyl group, and the alkoxyl group may preferably have up to 3 carbon atoms. More preferred examples include 2-methoxyethoxyl group and 2-ethoxyethoxyl group.

When the alkoxyl group further has an alkylthio group as a substituent, the alkoxyl group may be either straight or branched form having from 1 to 6 carbon atoms, and the substituting alkylthio group may also be either straight or branched form having from 1 to 6 carbon atoms. Though the substituting position of alkylthio group is not particularly limited, it may preferably be substituted on the terminal carbon atom of the alkoxyl group. An alkylthioethoxyl group is desirable as the alkoxyl group having an alkylthio group, and the alkylthio group may preferably have from 1 to 3 carbon atoms. More preferred examples include 2-methylthioethoxyl group and 2-ethylthioethoxyl group.

In the aforementioned aryl group and heteroaryl group having an "alkoxyl group which may have a substituent" as a substituent, the number of the alkoxyl groups may be any one of from mono-substitution to peralkoxyl substitution. When two or more alkoxyl groups are present, they may be the same or different from one another. As the alkoxyl substitution, mono-, di- or tri-substitution is suitable.

When the aryl group and heteroaryl group have an alkylthio group as a substituent, the alkylthio group maybe either straight or branched group having form 1 to 6 carbon atoms, and its preferred examples include methylthio group and ethylthio group.

When the alkylthio group has a halogen atom as a substituent, the alkylthio group may be either straight or branched form having from 1 to 6 carbon atoms, and fluorine atom is desirable as the halogen atom. With regard to the number of fluorine atoms, it may be any one of from mono-substitution to perfluoro substitution. Its examples include monofluoromethylthio group, difluoromethylthio group, trifluormethylthio group, 2,2,2-trifluoroethylthio group and the like.

When the alkylthio group further has hydroxyl group as a substituent, the alkylthio group may be either straight or branched form having from 1 to 6 carbon atoms. Though the substituting position of hydroxyl group is not particularly limited, it may preferably be substituted on the term carbon atom of the alkylthio group. As the alkylthio group having hydroxyl group, those which have up to 3 carbon atoms are desirable, and hydroxymethylthio group, 1-hydroxyethylthio group, 2-hydroxyethylthio group, 2-hydroxypropylthio group, 3-hydroxypropylthio group and the like are preferable.

When the alkylthio group further has an alkoxyl group as a substituent, the alkylthio group may be either straight or branched form having from 1 to 6 carbon atoms, and the substituting alkoxyl group may also be either straight or branched form having from 1 to 6 carbon atoms. Though the substituting position of alkoxyl group is not particularly limited, it may preferably be substituted on the terminal carbon atom of the alkylthio group. An alkoxyethylthio group, an alkoxyethyl group and an alkoxypropyl group is desirable as the alkylthio group having an alkoxyl group, and the alkoxyl group may preferably have up to 3 carbon atoms. More preferred examples include 2-methoxyethylthio group and 2-ethoxyethylthio group.

When the alkylthio group further has an alkylthio group as a substituent, the alkylthio group may be either straight or branched form having from 1 to 6 carbon atoms, and the substituting alkylthio group may also be either straight or branched form having from 1 to 6 carbon atoms. Though the substituting position of alkylthio group is not particularly limited, it may preferably be substituted on the terminal carbon atom of the alkylthio group. An alkylthioethylthio group is desirable as the alkylthio group having an alkylthio group, and the alkylthio group may preferably have from 1 to 3 carbon atoms. More preferred examples include 2-methylthioethylthio group and 2-ethylthioethylthio group.

In such an aryl group or heteroaryl group having an "alkylthio group which may have a substituent" as a substituent, the number of the alkylthio groups may be any one of from mono-substitution to peralkylthio substitution. When two or more alkylthio groups are present, they may be the same or different from one another. As the alkylthio substitution, mono-substitution is suitable.

When the aryl group and heteroaryl group have a halogen atom as a substituent, fluorine atom, chlorine atom and bromine atom are desirable as the halogen atom. Fluorine atom is particularly desirable, and the number of fluorine atoms in that case may be any one of from mono-substitution to perfluoro substitution.

Its examples include 2-fluorophenyl group, 3-fluorophenyl group, 4-fluorophenyl group, 2,4-difluorophenyl group, 2,5-difluorophenyl group, 2,6-difluorophenyl group, 3,4-difluorophenyl group, 3,5-difluorophenyl group, 2,4,6-trifluorophenyl group, 3,4,5-trifluorophenyl group, 2,3,5,6-tetrafluorophenyl group, pentafluorophenyl group, 4-fluoro-1-naphthyl group, 7-fluoro-1-naphthyl group, 3-fluoro-2-pyridyl group, 6-fluoro-2-pyridyl group, 2,4,5,6-tetrafluoro-3-pyridyl group, 2,3,5,6-tetrafluoro-4-pyridyl group and the like.

When the aryl group and heteroaryl group have hydroxyl group as a substituent, an aryl substituted with hydroxyl group is preferred, and a substituted phenyl group is particularly preferred. For example, 2-hydroxyphenyl group 3-hydroxyphenyl group, 4-hydroxyphenyl group, 2,4-dihydroxyphenyl group and the like can be cited.

When the aryl group and heteroaryl group have amino group as a substituent, an amino-substituted aryl group is preferred, and an amino-substituted phenyl group is particularly preferred. The amino group of this case may have 1 or 2 substituents selected from the group consisting of formyl group, an alkyl group having from 1 to 6 carbon atoms, an acyl group having fm 2 to 5 carbon atoms and an alkoxycarbonyl group having from 2 to 5 carbon atoms, and a monoalkylamino-substituted phenyl group, a dialkylamino-substituted phenyl group (the alkyl groups of this case may be the same or different from each other) and an acylamino-substituted phenyl group are preferable.

2-Aminophenyl group, 3-aminophenyl group, 4-aminophenyl group, 2-methylaminophenyl group, 4-methylaminophenyl group, 2-dimethylaminophenyl group, 4-dimethylaminophenyl group, 4-acetoxyaminophenyl group and the like can be exemplified.

When the aryl group and heteroaryl group have two or more substituents, their combination may be a combination optionally selected from the group consisting of a halogen atom, hydroxyl group, thiol group, amino group, nitro group, cyano group, carboxyl group, carbamoyl group, phenyl group, an alkyl group having from 1 to 6 car-bon atoms, an alkoxyl group having from 1 to 6 carbon atoms, an alkylthio group having from 1 to 6 carbon atoms, an alkoxycarbonyl group having from 2 to 6 carbon atom, an acyl group having form 2 to 5 con atoms and a heteroaryl group (a five-membered ring or a six-membered ring and contains form 1 to 4 hetero atoms optionally selected from nitrogen atom, oxygen atom and sulfur atom), but it is desirable that one of them is selected from an alkyl group, an alkoxy group, a halogen atom, hydroxyl group and amino group. As the halogen atom, fluorine atom is particularly desirable.

As examples of the case in which the aryl group and heteroaryl group have two or more substituents, 2-fluoro-4-hydroxyphenyl group, 3-amino-4,6-difluorophenyl group, 4,6-difluoro-3-methylaminophenyl group, 2,6-difluoro-4-methoxyphenyl group, 4-fluoro-2-methylphenyl group, 4-hydroxy-3,5 dimethylphenyl group, 3,5-dimethyl-4-methoxyphenyl group, 6-amino-3,5-difluoro-2-pyridyl group, 5-chloro-6-methyl-4-pyrimidinyl group and the like can be cited.

In this connection, the carbon atom, to which $R^1$ is bonded, becomes an asymmetric carbon to generate isomers, and all of such isomers are included in the invention.

Also, when the substituent of $R^1$ is a (substituted) phenyl group or a biaryl type (substituted) heteroaryl group of a five-membered ring or a six-membered ring containing from 1 to 4 hetero atoms optionally selected from nitrogen atom, oxygen atom and sulfur atom (the term "(substituted)" means that it may have a substituent), it generates isomers originated form axial chirality, and all of such isomers are included in the invention.

The substituents $R^2$ and $R^3$ each independently represents hydrogen atom or an alkyl group having form 1 to 6 carbon atoms, and the alkyl group may have one or more substituents selected from the group consisting of hydroxyl group, a halogen atom, an alkylthio group having from 1 to 6 carbon atoms and an alkoxyl group having from 1 to 6 carbon atoms.

As the alkyl group, it may be either straight or branched group having from 1 to 6 carbon atoms, and its preferred examples include methyl group, ethyl group, normal propyl group and isoproyl group.

When the alkyl group further has hydroxyl group as a substituent, the alkyl group may be either straight or branched form having from 1 to 6 carbon atoms. Though the substituting position of hydroxyl group is not particularly limited, it may preferably be substituted on the terminal carbon atom of the alkyl group. As the alkyl group having hydroxyl group, those which have up to 3 carbon atoms are desirable, and hydroxymethyl group, 2-hydroxyethyl group, 2-hydroxypropyl group, 3-hydroxypropyl group and the like are preferable.

When the alkyl group further has a halogen atom as a substituent, the alkyl group may be either straight or branched form having from 1 to 6 carbon atoms, and fluorine atom is desirable as the halogen atom. With regard to the number of fluorine atoms, it may be any one of from mono-substitution to perfluoro substitution. Its examples include monofluoromethyl group, difluoromethyl group, trifluoromethyl group, 2,2,2-trifluoroethyl group and the like.

When the alkyl group further has an alkylthio group as a substituent, the alkyl group may be either straight or branched form having from 1 to 6 carbon atoms, and the substituting alkylthio group may also be either straight or branched form having from 1 to 6 carbon atoms. Though the substituting position of alkylthio group is not particularly limited, it may preferably be substituted on the terminal carbon atom of the alkyl. An alkylthiomethyl, an alkylthioethyl group and an alkylthiopropyl group are desirable as the alkyl group having an alkylthio group, and the alkylthio group may preferably have from 1 to 3 carbon atoms. More preferred examples include methylthiomethyl group, ethylthiomethyl group and methylthioethyl group.

When the alkyl group further has an alkoxyl group as a substituent, the alkyl group may be either straight or branched form having from 1 to 6 carbon atoms, and the substituting alkoxyl group may also be either straight or branched form having from 1 to 6 carbon atoms. Though the substituting position of alkoxyl group is not particularly limited, it may preferably be substituted on the terminal carbon atom of the alkyl group. An alkoxymethyl group, an alkoxyethyl group and an alkoxypropyl group are desirable as the alkyl group having an alkoxyl group, and the alkoxyl group may preferably have up to 3 carbon atoms. More preferred examples include methoxymethyl group, ethoxymethyl group and methoxyethyl group.

$R^4$, $R^5$ and $R^6$ each independently represents hydrogen atom, hydroxyl group, a halogen atom, carbamoyl group, an alkyl group having from 1 to 6 carbon atoms, an alkoxyl group having from 1 to 6 carbon atoms or an alkylthio group having from 1 to 6 carbon atoms, and the alkyl group among them may have one or more substituents selected from the group consisting of hydroxyl group, a halogen atom and an alkoxyl group having from 1 to 6 carbon atoms. In addition, $R^5$ and $R^1$ integrated into a polymethylene chain having from 3 to 6 carbon atoms (forms a spiro-ring system together with pyrrolidine ring), hydroyimino group or an alkyloxy-imino group having from 1 to 6 carbon atoms.

As the halogen atom, fluorine atom or chlorine atom is desirable.

As the alkyl group, it may be either straight or branched group having from 1 to 6 carbon atoms, and its preferred examples include methyl group, ethyl group, normal propyl group and isopropyl group.

As the alkoxyl group, it may be either straight or branched group having form 1 to 6 carbon atoms, and its preferred examples include methoxy group and ethoxy group.

As the alkylthio group, it may be either straight or branched group having form 1 to 6 carbon atoms, and its preferred examples include methylthio group and ethylthio group.

When hydroxyl group is present as a substituent on an alkyl group having from 1 to 6 carbon atoms, the alkyl group may be either straight or branched form. Though the substituting position of hydroxyl group is not particularly limited, it may preferably be substituted on the terminal carbon atom of the alkyl group. Preferred examples of the hydroxyl group-substituted alkyl group having from 1 to 6 carbon atoms include hydroxymethyl group, 2-hydroxyethyl group and 3-hydroxypropyl group.

As the halogen atom of an alkyl group having a halogen atom, fluorine and chlorine atoms are preferable, and fluorine atom is particularly preferable. The alkyl group may be either a straight or branched fox.

In the alkoxyl group-containing alkyl group having from 1 to 6 carbon atoms, each of the alkyl group moieties maybe either a straight or branched form, and an alkoxymethyl group or an alkoxyethyl group is preferable. Methoxymethyl group, ethoxymethyl group and 2-methoxyethyl group can be cited as more preferred examples.

When the substituents $R^5$ and $R^6$ are integrated to form a polymethylene chain, a ring of from three- to six-membered ring is newly added to the pyrrolidine ring to form a spiro-ring structure. As the size of the newly formed ring, a cyclopropyl ring or cyclobutyl ring having 2 or 3 carbon atoms is preferable.

Also, when the substituents $R^1$ and $R^1$ are integrated into an alkyloxyimino group represented by the following formula,

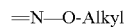

the alkyl group may be either a straight or branched form. Preferred as the alkyloxyimino group are methoxyimino group and ethoxyimino group.

The substituents $R^7$ and $R^8$ each independently represents hydrogen atom or an alkyl group having from 1 to 6 carbon atoms. As the alkyl group, it may be either a straight or branched group having from 1 to 6 carbon atoms and is preferably methyl group, ethyl group, normal propyl group or isopropyl group. A case in which each of them is hydrogen atom is desirable.

Q is a partial structure represented by the following formula.

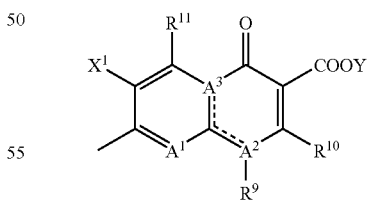

In this structural formula, $A^2$ and $A^3$ each independently represents nitrogen atom or carbon atom, and $A^2$ and $A^3$ and the carbon atoms, to which they are bonded, are linked to form a partial structure

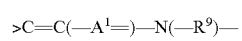

or a partial structure

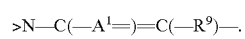

A fused heterocyclic system partial structure represented by the following formula

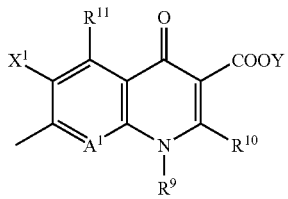

or the following formula

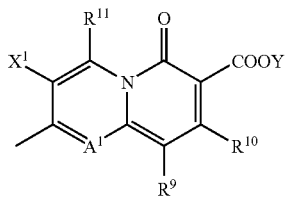

is preferred as the structure of Q.

The substituent $R^9$ is an alkyl group having from 1 to 6 carbon atoms, an alkenyl group having from 2 to 6 carbon atoms, a halogenoalkyl group having from 1 to 6 carbon atoms, a cyclic alkyl group having from 3 to 6 carbon atoms which may have a substituent, an aryl group which may have a substituent, a heteroaryl group which may have a substituent, an alkoxyl group having from 1 to 6 carbon atoms or an alkylamino group having from 1 to 6 carbon atoms.

In this case, ethyl group is particularly desirable as the alkyl group having from 1 to 6 carbon atoms. As the alkenyl group having from 2 to 6 carbon atoms, vinyl group or 1-isopropenyl group is desirable. 2-Fluoroethyl group is desirable as the halogenoalkyl group having from 1 to 6 carbon atoms. Cyclopropyl group is particularly desirable as the cyclic alkyl group, and a halogen atom, particularly fluorine atom, is desirable as the substituent of the cyclic alkyl group.

Examples of the aryl group which may have a substituent include phenyl or the like group which may have 1 to 3 substituents selected form the group consisting, for example, of fluorine atom, chlorine atom, bromine atom or the like halogen atom, hydroxyl group, amino group, nitro group, an alkyl group having from 1 to 6 carbon atoms and an alkoxyl group having from 1 to 6 carbon atoms, and its preferred examples include phenyl group, 2-fluorophenyl group, 4-fluorophenyl group, 2,4-difluorophenyl group, 2-fluoro-4-hydroxyphenyl group, 3-amino-4,6-difluorophenyl group and 4,6-difluoro-3-methylaminophenyl group. This aryl group may be the same as the aryl group of the substituent $R^1$ or different from it.

The heteroaryl group is a compound derived from a five-membered or six-membered aromatic heterocyclic compound which contains one or more hetero atoms selected from nitrogen atom, oxygen atom and sulfur atom. This heteroaryl group may be the same as the heteroaryl group of the substituent $R^1$ or different from it. As the heteroaryl group of the substituent $R^9$, pyridyl group, pyrimidyl group and the like can be exemplified. As the substituent on these rings, an alkyl group, a halogen atom or the like is desirable. Particularly preferred is 6-amino-3,5-difluoro-2-pyridyl group.

Methoxyl group is desirable as the alkoxyl group having from 1 to 6 carbon atoms. Methylamino group is desirable as the alkylamino group having from 1 to 6 carbon atoms.

As the substituent $R^9$, a cyclic alkyl group or a halogenocycloalkyl group is desirable. Among these groups, cyclopropyl group or a 2-halogenocyclopropyl group is desirable. As the halogen atom, fluorine atom is desirable.

The substituent $R^{10}$ represents hydrogen atom or an alkylthio group having from 1 to 6 carbon atoms, or $R^9$ and $R^{10}$ may be integrated to form a hydrocarbon system ring structure by incorporating a part of the mother skeleton (namely by including the carbon atom to which $R^{10}$ is bonded and $A^2$). The thus formed ring may contain sulfur atom as a constituent atom, and the ring may further have an alkyl group having from 1 to 6 carbon atoms as a substituent. The ring to be formed herein may have a size of from four-membered ring to six-membered ring, and the ring may be saturated or unsaturated. As the fused ring structure formed in this manner, the following can be exemplified.

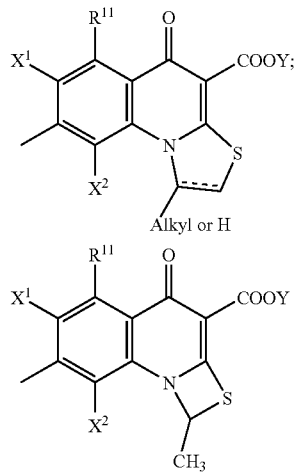

The substituent $X^1$ is a halogen atom or hydrogen atom, and fluorine atom is desirable in the case of the halogen atom. Among these atoms, fluorine atom or hydrogen atom is desirable as the substituent.

The substituent $R^{11}$ represents hydrogen atom, amino group, hydroxyl group, thiol group, a halogenomethyl group, an alkyl group having from 1 to 6 carbon atoms, an alkenyl group having from 2 to 6 carbon atoms, an alkynyl group having from 2 to 6 carbon atoms or an alkoxyl group having from 1 to 6 carbon atoms, and the amino group among them may have one or two substituents selected from the group consisting of formyl group, an alkyl group having from 1 to 6 carbon atoms and an acyl group having from 2 to 6 carbon atoms.

As the alkyl group, it may be either a straight or branched group having from 1 to 6 carbon atoms, and its preferred examples include methyl group, ethyl group, normal propyl group and isopropyl group. The alkenyl group may be either a straight or branched group having from 2 to 6 carbon atoms and is preferably vinyl group. As the alkynyl group, it may be either a straight or branched group having from 2 to 6 carbon atoms and is preferably ethynyl group. Fluorine atom is particularly desirable as the halogen of the halogenomethyl group, and its number may be from 1 to 3. The alkoxyl group may have from 1 to 6 carbon atoms and is preferably methoxyl group.

The substituent $R^{11}$ is preferably hydrogen atom, an alkyl group or amino group, of which methyl group or unsubstituted amino group is preferred.

When the substituent $R^{11}$ is amino group, hydroxyl group or thiol group, they may be protected with ordinarily used protective groups.

Examples of such protective groups include tert-butoxycarbonyl group, 2,2,2-trichloroethoxycarbonyl group and the like (substituted) alkoxycarbonyl groups; benzyloxycarbonyl group, para-methoxybenzyloxycarbonyl group, para-nitrobenzyloxycarbonyl group and the like (substituted) aralkyloxycarbonyl groups; acetyl group, methoxyacetyl group, trifluoroacetyl group, chloroacetyl group, pivaloyl group, formyl group, benzoyl group and the like (substituted) acyl groups; tert-butyl group, benzyl group, para-nitrobenzyl group, para-methoxybenzyl group, triphenylmethyl group and the like (substituted) alkyl groups or (substituted) aralkyl groups; methoxymethyl group, tert-butoxymethyl group, tetrahydropyranyl group, 2,2,2-trichloroethoxymethyl group and the like (substituted) ethers; and trimethylsilyl group, isopropyldimethylsilyl group, tert-butyldimethylsilyl group, tribenzylsilyl group, tert-butyldiphenylsilyl group and the like (alkyl and or aralkyl)-substituted silyl groups. Compounds having substituents protected with these substituents are particularly desirable as intermediates for the production.

When $A^1$ is a partial structure of the following formula (II),

(II)

$X^2$ represents hydrogen atom, amino group, a halogen atom, cyano group, a halogenomethyl group, a halogenomethoxyl group, an alkyl group having from 1 to 6 carbon atoms, an alkenyl group having from 2 to 6 carbon atoms, an alkynyl group having from 2 to 6 carbon atoms or an alkoxyl group having from 1 to 6 carbon atoms, wherein the amino group may have one or two substituents selected from the group consisting of formyl group, an alkyl group having from 1 to 6 carbon atoms and an acyl group having from 2 to 5 carbon atoms.

As the alkyl group, it may be either a straight or branched group having from 1 to 6 carbon atoms and its preferred examples include methyl group, ethyl group, normal propyl group and isopropyl group. The alkenyl group may be either a straight or branched group having from 2 to 6 carbon atoms and is preferably vinyl group. The alkynyl group may be either a straight or branched group having from 2 to 6 carbon atoms and is preferably ethynyl group. Fluorine atom is particularly desirable as the halogen of the halogenomethyl group, and its number may be from 1 to 3. As the alkoxyl group, it may have from 1 to 6 carbon atoms and is preferably methoxyl group. Fluorine atom is particularly desirable as the halogen of the halogenomethoxyl group, and its number may be from 1 to 3.

Among these substituents, an alkyl group or an alkoxyl group is desirable. More preferred are methyl group and ethyl group. These are desirable substituents particularly when Q is a partial structure shown by the following formula.

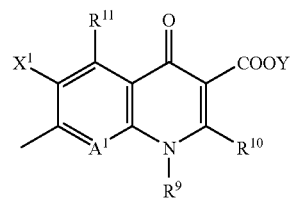

In addition, this $X^2$ and the aforementioned $R^9$ may be integrated to form a hydrocarbon system ring structure (size of the ring may be from four-membered ring to seven-membered ring, and it may be saturated or unsaturated) by incorporating a part of the mother skeleton (namely by including the carbon atom to which $X^2$ is bonded and $A^2$), and the thus formed ring may contain oxygen atom, nitrogen atom or sulfur atom as a constituent atom, and the ring may also have an alkyl group having from 1 to 6 carbon atoms as a substituent. As the fused ring structure formed in this manner, the following can be exemplified.

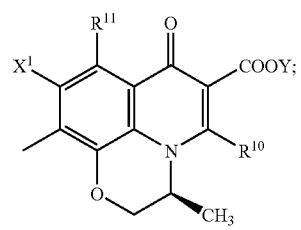

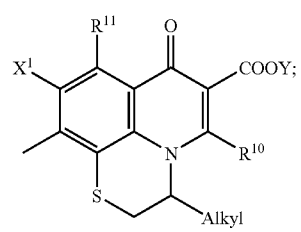

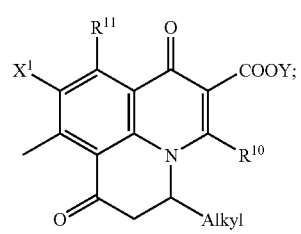

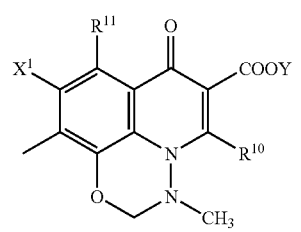

Among these fused ring systems, 2,3 dihydro-7-oxo-7H-pyrido[1,2,3-de][1.4]benzoxazine-6-carboxylic acid-10-yl group, particularly its 3-position (S)-methyl form, is desirable.

As Q, a partial structure of the following form a

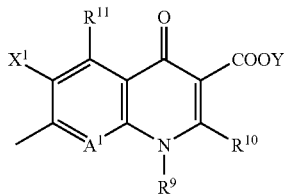

is desirable. Also in this case, it is desirable that $A^1$ is the partial structure of formula (II).

When Q is the partial structure described above and $A^1$ is the partial structure of formula (II), a preferred combination of $R^{11}$ and $X^2$ is a case in which $R^{11}$ is amino group, hydrogen atom, hydroxyl group or an alkyl group having from 1 to 6 carbon atoms and $X^2$ is an alkyl group having from 1 to 6 carbon atoms, an alkoxyl group having from 1 to 6 carbon atoms, a halogenomethoxyl group or hydrogen atom.

A more preferred combination is a case in which $R^{11}$ is amino group, hydrogen atom, hydroxyl group or methyl group and $X^2$ is methyl group, methoxyl group, difluoramethoxyl group or hydrogen atom.

A most preferred combination is a case in which $R^{11}$ is amino group, hydrogen atom, hydroxyl group or methyl group and $X^2$ is methyl group or methoxyl group.

For these $R^{11}$ and $X^2$, fluorine atom is desirable as $X^1$.

When the substituents $X^1$ and $X^2$ are halogen atoms, fluorine atom is particularly preferable as $X^1$, and fluorine atom or chlorine atom is preferable as $X^2$.

When Q is a partial structure represent the following formula

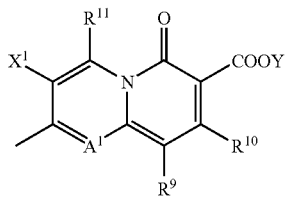

and $A^1$ is the partial structure of formula (II), a preferred combination of $R^{11}$ and $X^2$ is a case in which $R^{11}$ is amino group, hydrogen atom, hydroxyl group or an alkyl group having from 1 to 6 carbon atoms and $X^2$ is an alkyl group having from 1 to 6 carbon atoms, an alkoxyl group having from 1 to 6 carbon atoms, a halogenomethoxyl group or hydrogen atom.

A more preferred combination is a case in which $R^{11}$ is amino group hydrogen atom, hydroxyl group or methyl group and $X^2$ is methyl group, methoxyl group, difluoromethoxyl group or hydrogen atom.

A most preferred combination is a case in which $R^{11}$ is amino group, hydrogen atom, hydroxyl group or methyl group and $X^2$ is methyl group or methoxyl group.

When the substituents $X^1$ and $X^2$ are halogen atoms, fluorine atom is particularly preferable as $X^1$, and fluorine atom or chlorine atom is preferable as $X^2$.

Next, the halogenocyclopropyl group of $R^9$ is described.

As the substitutable halogen atom, fluorine atom and chlorine atom can be exemplified, of which fluorine atom is particularly preferred.

Regarding the steric environment at this moiety, it is particularly desirable that the halogen atom and pyridonecarboxylic acid moiety have cis-configuration on the cyclopropane ring.

So-called enantiomeric isomers are present due to the cis-2-halogenocyclopropyl moiety alone of $R^9$, and strong antibacterial activity and high safety have been found in both isomers.

The compound of the invention shows excellent characteristics by having a pyrrolidinyl substituent of a structure shown below.

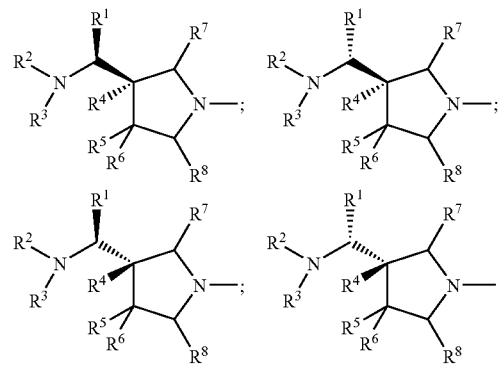

In this substituent, the above four isomers are present based on the asymmetric carbon atom on the pyrrolidin ring to which the substituent —CH(—$R^1$)N(—$R^2$)—$R^3$ and the substituent $R^4$ are bonded and an asymmetric carbon atom to which $R^1$ is bonded.

On the other hand, structure activity correlation among four optically active substances derived from steric configuration of the 7-position substituent in a 7-[3-(1-aminoethyl)pyrrolidin-1-yl]quinolonecarboxylic acid derivative is described in *Chemical & Pharmaceutical Bulletin*, vol. 42, p. 1442 (1994). It described that 3-(S)-[1-(R)-aminoethyl] pyrrolidin-1-yl group has the most highest antibacterial activity among the four optically active substances.

The present inventors have considered that

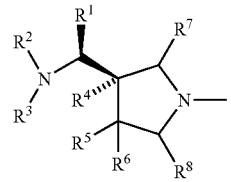

was most desirable among the four optically active substances having the structures shown in the above.

That is, the compound of the invention is characterized in that the aromatic group-substituted aminomethylpyrrolidine derivative represented by the formula (I), salts thereof and hydrates thereof show broad and potent antibacterial activity upon Gram-negative bacteria and Gram-positive bacteria, and show potent antibacterial activity particularly upon resistant strains of Gram-positive bacteria including MESA, PRSP and VRE.

Particularly, a compound represented by the formula (I) in which the aromatic group-substituted aminomethylpyrrolidine derivative having the aforementioned structure was introduced at the 10-position of the 2,3-dihydro-3-(S)-methyl-7-oxo-7H-pyrido[1,2,3-de] [1.4]benzoxazine skeleton or the 7-position of the 6-fluoro-1-[2-(S)-fluoro-1-(R)-cyclopropl]-1-1,4-dihydro-4-oxoquin oline skeleton having excellent safety, salts thereof and hydrates thereof showed broad and strong antibacterial activity upon both of Gram-negative bacteria and Gram-positive bacteria including drug resistant strains, which was not expected before the invention.

When a compound of formula (I) of the invention has a structure in which diastereomers are present, and when such a compound of the invention is administered to human and animals, it is desirable to administer a compound which comprises a single diastereomer. The term "comprises a single diastereomer" as used herein means not only a case in which it is completely free from the other diastereomer but also a case in which it is in a chemically pure degree. In other words, it is interpretable that the other diastereomer may be present in such a degree that it does not exert influences upon physical constants and physiological activities of the compound.

Also, the term "stereochemically pure" as used herein means that, when a compound or the like exists in a plurality of isomer forms due to the presence of asymmetric carbon atoms, the compound is comprised of only one of them. The tem "pure" in this case can also be considered in the same manner as described above.

The pyridonecarboxylic acid derivative of the invention may be used either in its free form or as an acid addition salt or a salt of its carboxyl group. Examples of the acid addition salt include hydrochloride, sulfate, nitrate, hydrobromide, hydroiodide, phophate and the like inorganic acid salts, or acetate, methanesulfonate, benzenesulfonate, toluenesulfonate, citrate, maleate, fumarate, lactate and the like organic acid salts.

The salt of carboxyl group may be either an inorganic or an organic salt, and its examples include lithium salt, sodium salt, potassium salt and the like alkaline earth metal salts, magnesium salt, calcium salt and the like alkaline earth metal salts, ammonium salt, or triethylamine salt, N-methylglucamine salt, tris-(hydroxylmethyl) aminomethane salt and the like.

Also, these free form, acid addition salts and salts of carboxyl group of the compound of the invention may be present as hydrates.

On the other hand, a quinolone derivative whose carboxylic acid moiety is an ester is useful as a synthesis in intermediate or a prodrug. For example, alkyl esters, benzyl esters, alkoxyalkyl esters, phenylalkyl esters and phenyl esters are useful as synthesis intermediates.

Also, the ester to be used as a prodrug is an ester which is easily hydrolyzed in the living body and forms free form of carboxylic acid, and its examples include acetoxymethyl ester, pivaloyloxymethyl ester, ethoxycarbonyl ester, choline ester, dimethylaminoethyl ester, 5-indanyl ester, phthalidinyl ester, and 5-alkyl-2-oxo-1,3-dioxol-4-ylmethyl ester, 3-acetoxy-2-oxobutyl eater or the like oxoalkyl ester.

The compound of the invention represented by the formula (I) can be produced by various methods, and, in a preferred example, it can be produced for example by allowing a compound represented by formula (III):

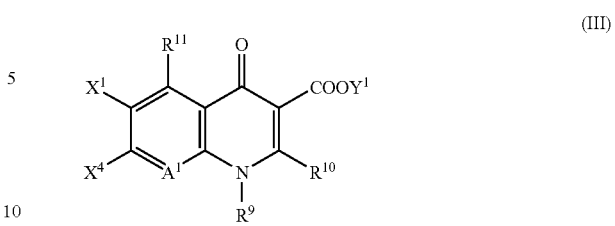

[wherein $X^4$ is a substituent which functions as a leaving group, such as fluorine atom, chlorine atom, bromine atom, substituted or unsubstituted phenylsulfonyl group or a substituted or unsubstituted alkylsulfonyl group having from 1 to 3 carbon atoms, $Y^1$ is the Y defined in the formula (I) or a boron-containing group represented by formula (IV):

$$-B(Y^{11})Y^{12} \qquad (IV)$$

(wherein each of $Y^{11}$ and $Y^{12}$ is fluorine atom or an alkylcarbonyloxy group having from 2 to 4 carbon atoms), and $R^9$, $R^{10}$, $R^{11}$, $A^1$ and $X^1$ are as defined in the form a (I)], or a compound represented by formula (V):

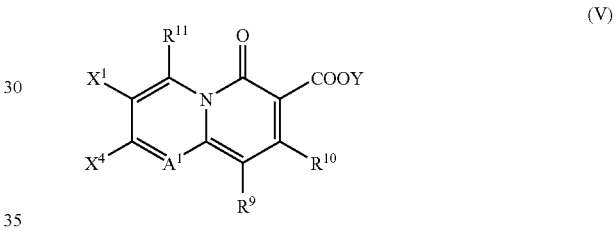

[wherein $X^4$ is a substituent which functions as a leaving group, such as fluorine atom, chlorine atom, bromine atom, substituted or unsubstituted phenylsulfonyl group or a substituted or unsubstituted alkylsulfonyl group having from 1 to 3 carbon atoms, and $R^9$, $R^{10}$, $R^{11}$, $A^1$, $X^1$ and Y are as defined in the formula (I)]to react with a compound represented by the following formula (VI)

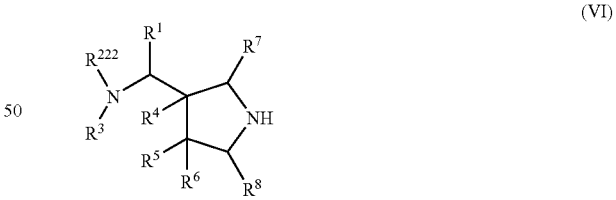

[wherein $R^{222}$ is the same as the $R^2$ defined in the formula (I), and $R^1$, $R^3$, $R^4$, $R^5$, $R^6$, $R^7$ and $R^8$ are as defined in the formula (I)] or an addition salt thereof.

The reaction can be carried out using or without using a solvent. The solvent to be used in the reaction may be any solvent which is inert under the reaction conditions, and its examples include dimethyl sulfoxide, pyridine, acetonitrile, ethanol, chloroform, dimethylformamide, dimethylacetamide, N-methylpyrrolidone, tetrahydrofuran, water and 3-methoxybutanol or a mixture thereof.

It is desirable to carry out the reaction in the presence of an acid receptor such as an inorganic base or an organic base, and its examples include an alkali metal or alkaline earth metal carbonate or bicarbonate or triethylamine, pyridine, 1, 8-diazabicycloundecene, N,N-diisopropylethylamine or the like organic basic compound.

The reaction can be carried out generally at a temperature of from room temperature to 200° C., preferably from 25 to 150° C. The reaction is carried out for a period of from 30 minutes to 48 hours and completes generally after about 30 minutes to 2 hours.

As the protective group of an amino group, it may be any protective group generally used in this field, and its examples include tert-butoxycarbonyl group, 2,2,2-trichloroethoxycarbonyl group and the like (substituted) alkoxycarbonyl groups; benzyloxycarbonyl group, para-methoxybenzyloxycarbonyl group, para-nitrobenzyloxycarbonyl group and the like (substituted) aralkyloxycarbonyl groups; acetyl group, methoxyacetyl group, trifluoroacetyl group, chloroacetyl group, pivaloyl group, formyl group, benzoyl group and the like (substituted) acyl groups; tert-butyl group, benzyl group, para-nitrobenzyl group, para-methoxybenzyl group, triphenylmethyl group and the like (substituted) alkyl groups or (substituted) aralkyl groups; methoxymethyl group, tert-butoxymethyl group, tetrahydropyranyl group, 2,2,2-trichloroethoxymethyl group and the like (substituted) ethers; and trimethylsilyl group, isopropyldimethylsilyl group, tert-butyldimethylsilyl group, tribenzylsilyl group, tert-butyldiphenylsilyl group and the like (alkyl and/or aralkyl)-substituted silyl groups.

When each of Y and $Y^1$ is an alkyl group having from 1 to 6 carbon atoms, an alkoxymethyl group having from 2 to 7 carbon atoms or a phenylalkyl group composed of an alkylene group having from 1 to 6 carbon atoms and phenyl group, it can be converted into a corresponding carboxylic acid by treating it under an acidic or basic condition which is generally employed for the hydrolysis of carboxylic acid esters.

When $Y^1$ is a structure of the formula (IV), its conversion into corresponding carboxylic acid can be effected by allowing the compound (III) or compound (V) to react with the compound (VI) and then treating it under an acidic or basic condition.

In addition, when de-protection is necessary, the compound of interest represented by the formula (I) can be obtained by removing the protective group under conditions suitable for the protective group.

The compound of formula (VI) can be produced by various methods, for example, it can be synthesized by a method shown in the reference examples as a preferred example, though not particularly limited thereto.

The compound of formula (VI) can be formed by removing Q' from a compound represented by the following formula

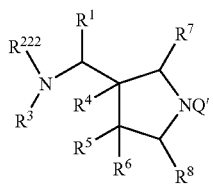

[wherein $R^{222}$ is the same as the $R^2$ defined in the formula (I) or represents a protective group of an amino group, $R^1$, $R^3$, $R^4$, $R^5$, $R^6$, $R^7$ and $R^8$ are as defined in the formula (I), Q' is a protective group of an amino group, wherein the protective group of an amino group may be selected from the group consisting of a (substituted) alkoxycarbonyl group, a (substituted) aralkyloxycarbonyl group, a (substituted) acyl group, a (substituted) alkyl group, a (substituted) aralkyl group and substituted silyl groups].

The compound described above can be present as a salt thereof, a hydrate thereof or a hydrate of the salt. As examples of the acid addition salt, an inorganic acid salt and an organic acid salt can be cited. Their illustrative examples include hydrochloride, sulfate, hydrobromide, hydroiodide, phosphate and the like inorganic acid salts, or methanesulfonate, benzenesulfonate, toluenesulfonate (sulfonic acid salts), acetate, citrate, maleate, fumarate, lactate (carboxylic acid salts) and the like organic acid salts.

When $R^{222}$ and Q' are protective groups of an amino group, they may be the same or different from each other, but it is convenient for producing the compound (I) that each is cut off under different reaction conditions.

As the $R^{222}$ and Q' which are protective groups of an amino group, the following can be exemplified. That is, they are a (substituted) alkoxycarbonyl group, a (substituted) aralkyloxycarbonyl group, a (substituted) acyl group, a (substituted) alkyl group, a (substituted) aralkyl group and substituted silyl groups.

The illustrative examples thereof include tert-butoxycarbonyl group, 2,2,2-trichloroethoxycarbonyl group and the like (substituted) alkoxycarbonyl groups; benzyloxycarbonyl group, para-methoxybenzyloxycarbonyl group, para-nitrobenzyloxycarbonyl group and the like (substituted) aralkyloxycarbonyl groups; acetyl group, methoxyacetyl group, trifluoroacetyl group, chloroacetyl group, pivaloyl group, formyl group, benzoyl group and the like (substituted) acyl groups; tert-butyl group, benzyl group, para-nitrobenzyl group, para-methoxybenzyl group, triphenylmethyl group and the like (substituted) alkyl groups or (substituted) aralkyl groups; methoxymethyl group, tert-butoxymethyl group, tetrahydropyranyl group, 2,2,2-trichloroethoxymethyl group and the like (substituted) ethers; and trimethylsilyl group, isopropyldimethylsilyl group, tert-butyldimethylsilyl group, tribenzylsilyl group, tert-butyldiphenylsilyl group and the like substituted silyl groups.

When the compound (I) is produced using the above compound having Q' as a protective group, it is necessary to carry out the reaction by removing the protective group Q'. In that case, its reaction with the compound (III) or (V) may be carried out generally by one pot, or the reaction may be carried out after once isolating the compound (VI) by Raving the protective group.

Cis-2-fluorocyclopropylamine comprised of a single isomer, which is desirable for the synthesis of the compound of formula (I) comprised of a single isomer, can be synthesized for example by the method described in JP-A-2-231475 (the term "JP-A" as used herein means an "unexamined published Japanese patent application"). Synthesis of the compound of formula (I) comprised of a single isomer using the optically active cis-2-fluorocyclopropylamine derivative obtained in this manner as the material can be carried out in accordance with the method described for example in JP-A-2-231475.

Since the compound of the invention has potent antibacterial actions, it can be used as medicaments for use in human bodies, animals and fishes or as preservatives of agricultural chemicals and food.

When the compound of the invention is used as a medicament for human bodies, its dose is within the range of from 50 mg to 1 g, preferably from 100 mg to 500 mg, per day per adult.

Also, its dose as animal use varies depending on the purpose of its administration (treatment or prevention), kind and size of each animal to be treated and kind and degree of each infected pathogenic bacterium, but is within the range of generally from 1 mg to 200 mg, preferably from 5 mg to 100 mg, per 1 kg body weight of each animal as a daily dose. The daily dose is administered once a day or by dividing it into 2 to 4 doses per day. As occasion demands, the daily dose may exceed the aforementioned range.

Since the compound of the invention is active against a broad range of microorganisms which cause various infectious diseases, it can treat, prevent or alleviate diseases induced by these pathogens.

As bacteria or bacterioid microorganisms on which the compound of the invention is effective, the genus *Staphylococcus, Streptococcus pyogenes*, hemolytic streptococci, enterococcus, pneumococcus, the genus *Peptostreptococcus, Neisseria gonorrhoeae, Escherichia coli*, the genera *Citrobacter*, the genus *Shigella, Klebsiella pneumoniae*, the genera *Enterobacter*, the genus *Serratia*, the genus *Proteus, Pseundomonas aeruginosa, Haemophilus influenzae*, the genus *Acinetobacter*, the genus *Campylobacter, Chlamydia trachomatis* and the like can be exemplified.

Also, as diseases which are induced by these pathogens, folliculitis, furuncle, carbuncle, erysipelas, phlegmon, lymphangitis, felon, subcutaneous abscess, hidradenitis, acne conglobata, infectious atheroma, perirectal abscess, mastitis, superficial secondary infections after injury, burn injury, operative wound and the like, pharyngitis, acute bronchitis, tonsilitis, chronic bronchitis, bronchiectasis, diffuse bronchiolitis, secondary infection of chronic respiratory disease, pneumonia, pyelonephritis, cystitis, prostatitis, epididymitis, gonococcal urethritis, nonspecific urethritis, cholecystitis, cholangitis, baciliary dysentery, enteritis, uterine adnexitis, intrauterine infection, bartholinitis, blepharitis, hordeolum, dacryocystitis, tarsadenitis, corneal ulcer, octitis media, sinusitis, periodentitis, pericoronitis, jaw infection, peritonitis, endocarditis, sepsis, meningitis, skin infection and the like can be exemplified.

It is also effective against various microorganisms which cause infectious diseases in animals, such as the genus *Escherichia*, the genus *Salmonella*, the genus *Pasteurella*, the genus *Haemophilus*, the genus *Bordetella*, the genus *Staphylococcus*, the genus *Mycoplasma* and the like.

Illustrative examples of such diseases include colibacillosis, pullorum disease, avian paratyphoid, avian cholera, infectious coryza, staphylococcosis, mycoplasma infection and the like in the case of birds, colibaciliosis, salmonellosis, pasteurellosis, haemophilus infection, atrophic rhinitis, exudative epidermis, mycoplasma infection and the like in the case of pigs, colibacillosis, salmonellosis, hemorrhagic sepsis, mycoplasma infection, bovine pleuropneumonia, bovine mastitis and the like in the case of cattle, colisepsis, salmonella infection, hemorrhagic sepsis, uterine empyema, cystitis and the like in the case of dogs, and exudative pleurisy, cystitis, chronic rhinitis, haemophilus infection, kitten diarrhea, mycoplasma infection and the like in the case of cats.

The antibacterial preparation which comprises the compound of the invention can be prepared by selecting an appropriate preparation depending on each administration method and employing generally used various preparation methods. Regarding the dosage form of the antibacterial preparation which uses the compound of the invention as its principal agent, tablets, powders, granules, capsules, solutions, syrups, elixirs, oily or aqueous suspensions and the like can be exemplified as oral preparations. Regarding injections, a stabilizing agent, an antiseptic agent and a solubilizing agent may be used in the preparation, or a solution which may contain these auxiliary agents may be contained in a container and made into a solid preparation by freeze-drying or the like means to be redissolved when used. In addition, a single dose may be contained in a single container or multiple doses may be contained in the same container.

Also, solutions, suspensions, emulsions, ointments, gels, creams, lotions, sprays and the like can be exemplified as preparations for external use.

Solid preparations may contain pharmaceutically acceptable additives together with the active compound and can be prepared for example by mixing the compound with additives optionally selected from fillers, extenders, binders, disintegrators, solubilization enhancing agents, moistening agents, lubricating agents and the like.

As liquid preparations, solutions, suspensions, emulsions and the like can be exemplified, which may contain a suspending agent, an emilsifying agent and the like as additives.

Examples of the method for administering the compound of the invention to animals include a method in which it is orally administered directly or by mixing it with feed, a method in which it is made into a solution and then orally administered directly or by mixing it with drinking water or feed and a method in which it is administered by injection. As the pharmaceutical preparations for use in the administration of the compound of the invention to animals, it can be made optionally into powders, fine subtilaes, soluble powders, syrups, solutions or injections making use of the techniques generally used in this field.

Formulation examples of the pharmaceutical preparations are shown below.

TABLE 1

| Formulation Example 1. (Capsules): | |
|---|---:|
| Compound of Inventive Example 2 | 100.0 mg |
| Corn starch | 23.0 mg |
| CMC calcium | 22.5 mg |
| Hydroxymethyl cellulose | 3.0 mg |
| Magnesium stearate | 1.5 mg |
| Total | 150.0 mg |
| Formulation Example 2. (Solutions): | |
| Compound of Inventive Example 2 | 1–10 g |
| Acetic acid or sodium hydroxide | 0.5–2 g |
| Ethyl para-hydroxybenzoate | 0.1 g |
| Purified water | 88.9–98.4 g |
| Total | 100 g |
| Formulation Example 3. (Powders for feed mixing use): | |
| Compound of Inventive Example 2 | 1–10 g |
| Corn starch | 98.5–89.5 g |
| Light silicic anhydride | 0.5 g |
| Total | 100 g |

BEST MODE FOR CARRYING OUT THE INVENTION

The following describes the invention based on inventive examples and reference examples, though the invention is not limited thereto.

REFERENCE EXAMPLE 1

N-Methyl-N-methoxy-[1-(R)-phenylethyl-5-oxopyrrolidine-3-(R)-carboxamide

Under ice-cooling, oxalyl chloride (6.54 ml, 0.075 mol) and dimethylformamide (3 drops) were added to dichloromethane solution (200 ml) of 1-[1-(R)-phenylethyl]-5-oxopyrrolidine-3-(R)-carboxylic acid (11.66 g, 0.05 mol) and stirred overnight at room temperature. After evaporation of the solvent under a reduced pressure, toluene (100 ml) was added and the solvent was again evaporated under a reduced pressure. The residue was mixed with dichloromethane (200 ml) and N,O-methylhydroxylamine hydrochloride (5.47 g, 0.055 mol), and a dichloromethane solution (50 ml) of triethylamine (17.4 ml, 0.125 mol) was added dropwise to the mixture which was stirred under ice-cooling, spending 15 minutes. This was stirred at ice-cooling for 30 minutes and then stirred at room temperature for 3 hours. The reaction solution was washed with 10% citric acid aqueous solution (100 ml), water (100 ml) and saturated sodium bicarbonate aqueous solution (100 ml) in that order and then dried over anhydrous sodium sulfate. The solvent was evaporated under a reduced pressure and the resulting residue was applied to a silica gel column chromatography. By eluting with a chloroform:methanol system of from (50:1) to (20:1), 11.32 g (82%) of the title compound was obtained as a brown oil.

$^1$H-NMR (400 MHz, CDCl$_3$) δ: 1.54 (3H, d, J=6.84 Hz), 2.65 (1H, dd, J=9.77, 7.09 Hz), 2.77 (1H, dd, J=8.79, 7.09 Hz), 3.12–3.18 (1H, m), 3.20 (3H, s), 3.37–3.48 (1H, m), 3.55–3.64 (1H, m), 3.65 (3H, s), 5.50 (1H, q, J=6.84 Hz), 7.28–7.37(5H, m).

REFERENCE EXAMPLE 2

4-(R)-Phenylcarbonyl-1-[1-(R)-phenylethyl]-2-pyrrolidone

In an atmosphere of nitrogen, phenylmagnesium bride (3 mol/l diethyl ether solution, 15 ml) was added dropwise to tetrahydrofuran solution (50 ml) of N-methyl-N-methoxy-[1-(R)-phenylethyl]-5-oxopyrrolidine-3-(R)-carboxamide (2.49 g, 9.0 mmol), and the mixture was stirred at room temperature for 30 minutes. The reaction solution was mixed with 1 mol/l hydrochloric acid (50 ml) under ice-cooling and then extracted with ethyl acetate (8 ml×2). The organic layer was washed with saturated brine (100 ml) and then dried over anhydrous sodium sulfate. The solvent was evaporated under a reduced pressure and the resulting residue was applied to a silica gel column chromatography. By eluting with n-hexane:ethyl acetate (1:1), 2.36 g (89%) of the title compound was obtained as a light yellow oil.

$^1$H-NMR (400 MHz, CDCl$_3$) δ: 1.55 (3H, d, J=6.83 Hz), 2.79 (1H, dd, J=17.09, 9.77 Hz), 2.81 (1H, dd, J=17.09, 7.81 Hz), 3.23 (1H, dd, J=9.76, 8.79 Hz), 3.71 (1H, dd, J=9.76, 6.35 Hz), 3.97–4.05 (1H, m), 5.54 (1H, q, J=6.83 Hz), 7.27–7.38 (5H, m), 7.42–7.50 (2H, m), 7.55–7.61 (1H, m), 7.88–7.90 (2H, m).

REFERENCE EXAMPLE 3

4-(R)-[1-Hydroxy-1-phenylmethyl]-1-[1-(R)-phenylethyl]-2-pyrrolidone [F1], [F2]

Under ice-cooling, sodium borohydride (280 mg) was added to anhydrous ethanol (40 ml) solution of 4-(R) 1-phenylcarbonyl-1-[1-(R)-phenylethyl]-2-pyrrolidone (2.17 g, 7.40 mmol), and the mixture was stirred at the same temperature for 1 hour. The reaction solution was mixed with 10% citric acid (50 ml) under ice-cooling and then ethanol was evaporated under a reduced pressure. The residue was extracted with chloroform (80 ml×2), and the organic layer was washed with saturated brine (100 ml) and then dried over anhydrous sodium sulfate. The solvent was evaporated under a reduced pressure and the resulting residue was applied to a silica gel column chromatography. By eluting with n-hexane:ethyl acetate (1:3) to ethyl acetate (100%), 892 mg (41%) of the low polarity title compound [F1] and then 1.163 group (53%) of the high polarity title compound [F2] were respectively obtained each as a light yellow oil.

[F1];
$^1$H-NMR (400 MHz, CDCl$_3$) δ: 1.46 (3H, d, J=6.84 Hz), 2.03–2.14 (2H, m), 2.44–2.54 (1H, m), 3.05–3.09 (1H, m), 3.36–3.40 (1H, m), 3.47 (1H, brs), 4.45 (1H, d, J=7.81 Hz), 5.38 (1H, q, J=6.84 Hz), 7.22–7.31 (10H, m).

[F2];
$^1$H-NMR (400 MHz, CDCl$_3$) δ: 1.37 (3H, d, J=7.32 Hz), 2.26–2.32 (1H, m), 2.40–2.55 (2H, m), 2.73–2.77 (1H, m), 3.00–3.04 (1H, m), 4.32 (1H, brs), 4.42 (1H, d, J=6.8 Hz), 5.33 (1H, q, J=7.32 Hz), 7.15–7.27 (10H, m).

REFERENCE EXAMPLE 4

4-(R)-[1-Azido-1-phenylmethyl]-1-[1-(R)-phenylethyl]-2-pyrrolidone [F1], [F2]

Under ice-cooling, triethylamine (0.46 ml) and methanesulfonyl chloride (217 μl, 2.80 mmol) were added to dichloromethane (10 ml) solution of 4-(R)-[1-hydroxy-1-phenylmethyl]-1-[1-(R)-phenylethyl]-2-pyrrolidone [F1] (738 mg, 2.50 mmol), and the mixture was stirred at the same temperature for 1 hour. The reaction solution was mixed with 10% citric acid (20 ml) under ice-cooling and extracted with chloroform (30 ml×2). The organic layer was washed with saturated brine (100 ml) and then dried over anhydrous sodium sulfate. The solvent was evaporated under a reduced pressure, and the resulting residue was dissolved in N,N-dimethylformamide (10 ml), mixed with sodium azide (488 mg, 7.50 mmol) and then heated at 60° C. for 1.5 hours. After spontaneous cooling, the reaction solution was mixed with water (50 ml) and extracted with ethyl acetate (70 ml×3), and the organic layer was washed with saturated brine (150 ml) and then dried over anhydrous sodium sulfate. The solvent was evaporated under a reduced pressure and the resulting residue was applied to a silica gel column chromatography. By eluting with n-hexane:ethyl acetate (3:2), 701 mg (87%) of the title compound was obtained as a colorless oil.

The same reaction was also carried out regarding 4-(R)-[1-hydroxy-1-phenylmethyl]-1-[1-(R)-phenylethyl]-2-pyrrolidone [F2] (77%).

[F1];
¹H-NMR (400 MHz, CDCl₃) δ: 1.46 (3H, d, J=7.32 Hz), 2.53–2.66 (3H, m), 2.82 (1H, dd, J=9.76, 7.81 Hz), 2.94 (1H, dd, J=9.76, 5.86 Hz), 4.37 (1H, d, J=7.81 Hz), 5.47 (1H, q, J=7.32 Hz), 7.21–7.42 (10H, m).

[F2];
¹H-NMR (400 MHz, CDCl₃) δ: 1.54 (3H, d, J=7.33 Hz), 2.14 (1H, dd, J=17.09, 7.81 Hz), 2.26 (1H, dd, J=17.09, 8.78 Hz), 2.55–2.65 (1H, m), 3.14 (1H, dd, J=10.26, 7.81 Hz), 3.32 (1H, dd, J=10.26, 6.34 Hz), 4.36 (1H, d, J=9.28 Hz), 5.49 (1H, q, J=7.33 Hz), 7.26–7.43 (10H, m).

REFERENCE EXAMPLE 5

4-(R)-[1-Tert-butoxycarbonylamino-1-phenylmethyl]-1-[1-(R)-phenylethyl]-2-pyrrolidone [F1], [F2]

An ethanol (30 ml) solution of 4-(R)-[1-azido-1-phenylmethyl]-1-(1-(R)-phenylethyl]-2-pyrrolidone [F1] (641 mg, 2.0 mmol) was mixed with 10% palladium-carbon catalyst (53.8% moisture, 600 mg), and catalytic hydrogenation was carried out at room temperature for 6 hours under ordinary pressure. The reaction solution was filtered, and the solvent was evaporated under a reduced pressure. The residue was dissolved in dichloromethane (20 ml), mixed with di-tert-butyl dicarbonate (655 mg) and triethylamine (560 μl) and then stirred at room temperature for 13 hours. Chloroform (50 ml) was added to the reaction solution, this was washed with 10% citric acid (8 ml) and water (8 ml), and the resulting organic layer was dried over anhydrous sodium sulfate. The solvent was evaporated under a reduced pressure and the resulting residue was applied to a silica gel column chromatography. By eluting with a n-hexane:ethyl acetate system of from (1:1) to (2:3), 629 mg (80%) of the title compound was obtain as a colorless oil.

The same reaction was also carried out regarding 4-(R)-[1-azido-1-phenylmethyl]-1-[1-(R)-phenylethyl]-2-pyrrolidone [F2] (76%).

[F1];
¹H-NMR (400 MHz, CDCl₃) δ: 1.41 (9H, s), 1.46 (3H, d, J=7.32 Hz), 2.47–2.76 (3H, m), 2.76–2.89 (1H, m), 2.95–3.08 (1H, m), 4.62–4.73 (1H, m), 4.99–5.11 (1H, m), 5.47 (1H, q, J=7.32 Hz), 7.20–7.34 (10H, m).

[F2];
¹H-NMR (400 MHz, CDCl₃) δ: 1.37 (9H, s), 1.51 (3H, d, J=7.32 Hz), 2.08–2.26 (2H, m), 2.52–2.65 (1H, m), 3.06–3.18 (1H, m), 3.24–3.32 (1H, m), 4.52–4.66 (1H, m), 5.01–5.11 (1H, m), 5.47 (1H, q, J=7.32 Hz), 7.19–7.35 (10H, m).

REFERENCE EXAMPLE 6

3-(R)-[1-Tert-butoxycarbonylamino-1-phenylmethyl]-1-[1-(R)-phenylethyl]pyrrolidine [F1]

In an atmosphere of nitrogen 1Mborane-tetrahydrofuran complex (4.6 ml) was added dropwise to tetrahydrofuran (10 ml) solution of 4-(R)-[1-tert-butoxycarbonylamino-1-phenylmethyl]-1-[1-(R)-phenylethyl]-2-pyrrolidone [F1] (600 mg, 1.52 mmol) under ice-cooling, and then the mixture was stirred at room temperature for 13 hours. After evaporation of the solvent under a reduced pressure, the resulting residue was mixed with 80% hydrous ethanol (15 ml) and triethylamine (3 ml) and heated under reflux for 5 hours. After spontaneous cooling, the solvent was evaporated under a reduced pressure, and chloroform (30 ml) was added to the resulting residue. This was washed with water (10 ml) and saturated brine (10 ml) and dried over anhydrous sodium sulfate. The solvent was evaporated under a reduced pressure and the resulting residue was applied to a silica gel column chromatography. By eluting with chloroform:methanol (20:1), 510 mg (88%) of the title compound was obtained as colorless crystals.

The same reaction was also carried out regarding 4-(R)-[1-tert-butoxycarbonylamino-1-phenylmethyl]-1-[1-(R)-phenylethyl]-2-pyrrolidone [F2] (86%).

[F1];
¹H-NMR (400 MHz, CDCl₃) δ: 1.34 (3H, d, J=6.35 Hz), 1.47 (9H, s), 1.60–1.78 (2H, m), 2.18–2.39 (3H, m), 2.42–2.54 (1H, m), 2.83–2.95 (1H, m), 3.11 (1H, q, J=6.35 Hz), 4.47–4.57 (1H, m), 6.06–6.18 (1H, m), 7.16–7.33 (10H, m).

[F2];
¹H-NMR (400 MHz, CDCl₃) δ: 1.41 (3H, d, J=6.35 Hz), 1.46 (9H, s), 1.67–1.78 (1H, m), 1.89–2.02 (1H, m), 2.04–2.17 (1H, m), 2.17–2.28 (1H, m), 2.37–2.50 (2H, m), 3.01–3.19 (2H, m), 4.48–4.58 (1H, m), 6.62–6.73 (1H, m), 7.07–7.34 (10H, m).

REFERENCE EXAMPLE 7

3-(R)-[1-Tert-butoxycarbonylamino-1-phenylmethyl]pyrrolidine [F1]

An ethanol (20 ml) solution of 3-(R)-[1-tert-butoxycarbonylamino-1-phenylmethyl]-1-[1-(R)-phenylethyl]pyrrolidine [F1] (495 mg, 1.30,mol) was mixed with 10% palladium-carbon catalyst (53.8% moisture, 500 mg), and catalytic hydrogenation was carried out under ordinary pressure for 4 hours while heating at a temperature of 50° C. By filtering the reaction solution and evaporating the solvent under a reduced pressure, 359 mg (quantitative) of crude title compound was obtained as colorless crystals. This was used in the subsequent reaction without purification.

The same reaction was carried out regarding 3-(R)-[1-tert-butoxycarbonylamino-1-phenylmethyl]-1-[1-(R)-phenylethyl]pyrrolidine [F2] (quantitative).

INVENTIVE EXAMPLE 1

5-Amino-7-[3-(R)-(1-amino-1-phenylmethyl)-1-pyrrolidinyl]-6,8-difluoro-1-[2-(S)-fluoro-1-(R)-cyclopropyl]-1,4-dihydro-4-oxoquinoline-3-carboxylic acid [F1]

3-(R)-[1-Tert-butoxycarbonylamino-1-phenylmethyl]pyrrolidine [F1] (332 mg, 1.2 mmol) was added to an acetonitrile suspension (15 ml) of 5-amino-6,7,8-trifluoro-1-[2-(S)-fluoro-1-(S)-cyclopropyl]-1,4-dihydro-4-oxoquinoline-3-carboxylic acid (316 mg, 1.0 mmol), and the mixture was heated under reflux for 14 hours in the presence of triethylamine (2 ml). After spontaneous cooling, the solvent was evaporated under a reduced pressure and the resulting residue was dissolved in chloroform (50 ml). This was washed with 10% citric acid (30 ml×2) and saturated brine (20 ml) and dried over anhydrous sodium sulfate. The solvent was evaporated under a reduced pressure, and the resulting residue was mixed with concentrated hydrochloric acid (15 ml) and stirred at room temperature for 10 minutes. This hydrochloric acid solution was washed with chloroform (20 ml×3), adjusted to an alkaline liquid property by adding 30% sodium hydroxide aqueous solution under ice-cooling and then stirred at room temperature for 1 hour. This suspension was adjusted to a liquid property of pH 7.6 by adding concentrated hydrochloric acid and 1 mol/l hydrochloric acid and then extracted with chloroform (100 ml×3). The resulting organic layer was dried over anhydrous sodium sulfate and the solvent was evaporated under a reduced pressure. This was purified by recrystallizing from an ethanol-diethyl ether mixed solvent to obtain 241 mg (51%) of the title compound as light yellow crystals.

$^1$H-NMR (400 MHz, 0.1 mol/l NaOD) δ: 1.28–1.43 (2H, m), 1.53–1.66 (1H, m), 2.16–2.28 (1H, m), 2.31–2.42 (1H, m), 2.86–2.96 (1H, m), 3.09–3.20 (1H, m), 3.39–3.50 (2H, m), 3.58–3.70 (2H, m), 4.64–4.71 (0.5H, m), 4.78–4.96 (0.5H, m), 7.27–7.40 (5H, m), 8.10 (1H, s).

Melting point: 111.8–114.3° C. (decamp.)

Elemental analysis: for $C_{24}H_{23}F_3N_4O_3 \cdot 0.25H_2O$

Calcd.: C, 60.44; H, 4.97; N, 11.75. Found: C, 60.31; H, 4.92; N, 11.74.

INVENTIVE EXAMPLE 2

5-Amino-7-[3-(R)-(1-amino-1-phenylmethyl)-1-pyrrolidinyl]-6,8-difluoro-1-[2-(S)-fluoro-1-(R)-cyclopropyl]-1,4-dihydro-4-oxoquinoline-3-carboxylic acid [F2]

3-(R)-[1-Tert-butoxycarbonylamino-1-phenylmethyl] pyrrolidine [F2] (332 mg, 1.2 mmol) was added to an acetonitrile suspension (15 ml) of 5-amino-6,7,8-trifluoro-1-[2-(S)-fluoro-1-(S)-cyclopropyl]-1,4-dihydro-4-oxoquinoline-3-carboxylic acid (316 mg, 1.0 mmol), and the mixture was heated under reflux for 14 hours in the presence of triethylamine (2 ml). After spontaneous cooling, the solvent was evaporated under a reduced pressure and the resulting residue was dissolved in chloroform (50 ml). This was washed with 10% citric acid (30 ml×2) and saturated brine (20 ml) and dried over anhydrous sodium sulfate. The solvent was evaporated under a reduced pressure, and the resulting residue was mixed with concentrated hydrochloric acid (15 ml) and stirred at room temperature for 10 minutes. This hydrochloric acid solution was washed with chloroform (20 ml×3), adjusted to an alkaline liquid property by adding 30% sodium hydroxide aqueous solution under ice-cooling and then stirred at room temperature for 1 hour. This suspension was adjusted to a liquid property of pH 7.6 by adding concentrated hydrochloric acid and 1 mol/l hydrochloric acid and then extracted with chloroform (100 ml×3). The resulting organic layer was dried over anhydrous sodium sulfate and the solvent was evaporated under a reduced pressure. This was purified by recrystallizing from an ethanol-diethyl ether mixed solvent to obtain 388 mg (82%) of the title compound as light yellow crystals.

$^1$H-NMR (400 MHz, 0.1 mol/l NaOD) δ: 1.19–1.58 (5H, m), 2.27–2.43 (1H, m), 3.27–3.41 (1H, m), 3.46–3.74 (4H, m), 4.71–5.12 (1H, m), 7.21–7.41 (5H, m), 8.18 (1H, s).

Melting point: 202.3–205.1° C. (decomp.)

Elemental analysis: for $C_{24}H_{23}F_3N_4O_3 \cdot 0.25H_2O$

Calcd.: C, 60.44; H, 4.97; N, 11.75. Found: C, 60.31; H, 4.89; N, 11.84.

INVENTIVE EXAMPLE 3

7-[3-(R)-(1-Amino-1-phenylmethyl)-1-pyrrolidinyl]-6-fluoro-1-[2-(S)-fluoro-1-(R)-cyclopropyl]-1,4-dihydro-8-methoxy-4-oxoquinoline-3-carboxylic acid [F2]

3-(R)-[1-Tert-butoxycarbonylamino-1-phenylmethyl] pyrrolidine [F2] (304 mg, 1.1 mmol) and triethylamine (0.42 ml) were added to a dimethyl sulfoxide (3 ml) solution of 6,7-difluoro-1-[2-(S)-fluoro-1-(R)-cyclopropyl]-1,4 dihydro-8-methoxy-4-oxoquinoline-3-carboxylic acid $BF_2$ chelate (325 mg, 0.9 mmol), and the mixture was stirred at 30° C. for 19 hours. The solvent was evaporated under a reduced pressure, and the resulting residue was mixed with 80% hydrous ethanol (10 ml) and triethylamine (2 ml) and heated under reflux for 3 hours. After spontaneous cooling, the solvent was evaporated, the resulting residue was mixed with chloroform (50 ml), washed with 10% citric acid (40 ml×2) and water (50 ml) and dried over sodium sulfate, and then the solvent was evaporated. The resulting residue was mixed with concentrated hydrochloric acid (10 ml) and stirred at room temperature for 10 minutes, and then the resulting water layer was washed with chloroform (20 ml×3) and alkalified by adding 30% sodium hydroxide aqueous solution under ice-cooling. This was adjusted to a liquid property of pH 7.6 by adding concentrated hydrochloric acid and 1 mol/l hydrochloric acid and then extracted with chloroform (80 ml×3). The resulting organic layer was dried over anhydrous sodium sulfate and the solvent was evaporated under a reduced pressure. This was purified by recrystallizing from ethanol to obtain 294 mg (70%) of the title compound as light yellow crystals.

$^1$H-NMR (400 MHz, 0.1 mol/1 NaOD) δ: 1.23–1.61 (5H, m), 2.42–2.57 (1H, m), 3.32–3.44 (1H, m), 3.51 (3H, s), 3.54–3.64 (1H, m), 3.69–3.79 (2H, m), 3.93–4.03 (1H, m), 4.85–4.93 (0.5H, m), 4.99–5.09 (0.5H, m), 7.26–7.44 (5H, m), 7.65 (1H, d, J=14.16 Hz), 8.40 (1H, s).

Melting point: 141.8–144.2° C. (decomp.)

Elemental analysis: for $C_{25}H_{25}F_2N_3O_4 \cdot 0.5H_2O$

Calcd.: C, 62.75; H, 5.48; N, 8.78. Found: C, 63.00; H, 5.35; N, 8.78.

INVENTIVE EXAMPLE 4

10-[3-(R)-(1-Amino-1-phenylmethyl)-1-pyrrolidinyl]-9-fluoro-2,3-dihydro-3-(S)-methyl-7-oxo-7H-pyrido[1,2,3-de] [1,4]benzoxazine-6-carboxylic acid [F2]

3-(R)-[1-Tert-butoxycarbonylamino-1-phenylmethyl] pyrrolidine [F2] (304 mg, 1.1 mmol) and triethylamine (0.42 ml) were added to a dimethyl sulfoxide (3 ml) solution of 9,10-difluoro-2,3-difluoro-3-(S)-methyl-7-oxo-7H-pyrido [1,2,3-de] [1,4]benzoxazine-6-carboxylic acid $BF_2$ chelate (296 mg, 0.9 mmol), and the mixture was stirred at 30° C. for 19 hours. The solvent was evaporated under a reduced pressure, and the resulting residue was mixed with 80% hydrous ethanol (10 ml) and triethylamine (2 ml) and heated under reflux for 3 hours. After spontaneous cooling, the solvent was evaporated, the resulting residue was mixed with chloroform (50 ml), washed with 10% citric acid (40 ml×2) and water (50 ml) and dried over sodium sulfate, and then the solvent was evaporated. The resulting residue was mixed with concentrated hydrochloric acid (10 ml) and stirred at room temperature for 10 minutes, and then the resulting water layer was washed with chloroform (20 ml×3)

and alkalified by adding 30% sodium hydroxide aqueous solution under ice-cooling. This was adjusted to a liquid property of pH 7.6 by adding concentrated hydrochloric acid and 1 mol/l hydrochloric acid and then extracted with chloroform (80 ml×3). The resulting organic layer was dried over anhydrous sodium sulfate and the solvent was evaporated under a reduced pressure. This was purified by recrystallizing from ethanol to obtain 158 mg (40%) of the title compound as light yellow crystals.

$^1$H-NMR (400 MHz, 0.1 mol/l NaOD) δ: 1.35–1.61 (5H, m), 2.48–2.61 (1H, m), 3.29–3.38 (1H, m), 3.53–3.77 (4H, m), 4.21–4.29 (1H, m), 4.41–4.48 (1H, m), 4.52–4.61 (1H, m), 7.28–7.42 (5H, m), 7.51 (1H, d, J=13.18 Hz), 8.32 (1H, s).

Melting point: 169.3–171.0° C. (decomp.)

Elemental analysis: for $C_{24}H_{24}FN_3O_4 \cdot 0.25H_2O$

Calcd.: C, 65.22; H, 5.59; N, 9.51. Found: C, 65.50; H, 5.50; N, 9.52.

INVENTIVE EXAMPLE 5

5-Amino-7-[3-(R)-(1-amino-1-phenylmethyl)-1-pyrrolidinyl]-6-fluoro-1-[2-(S)-fluoro-1-(R)-cyclopropyl]-1,4-dihydro-8-methyl-4-oxoquinoline-3-carboxylic acid [F2]

3-(R)-[1-Tert-butoxycarbonylamino-1-phenylmethyl] pyrrolidine [F2] (414 mg, 1.5 mmol) and triethylamine (2 ml) were added to a dimethyl sulfoxide (3 ml) solution of 5-amino-6,7-difluoro-1-[2-(S)-fluoro-1-(R)-cyclopropyl]-1,4-dihydro-8-methyl-4-oxoquinoline-3-carboxylic acid (312 mg, 1.0 mmol), and the mixture was stirred at 130° C. for 5 days in an atmosphere of nitrogen. The solvent was evaporated and the resulting residue was mixed with chloroform (60 ml), this was washed with 10% citric acid (40 ml×2) and dried over sodium sulfate, and then the solvent was evaporated. The resulting residue was mixed with concentrated hydrochloric acid (10 ml) and stirred at room temperature for 10 minutes, and then the resulting water layer was washed with chloroform (30 ml×3) and alkalified by adding 30% sodium hydroxide aqueous solution under ice-cooling. This was adjusted to a liquid property of pH 7.6 by adding concentrated hydrochloric acid and 1 mol/l hydrochloric acid and then extracted with chloroform (80 ml×3). The resulting organic layer was dried over sodium sulfate, the solvent was evaporated, and then the resulting residue was applied to a preparative TlC. This was subjected to separation and purification by developing with the lower layer of chloroform:methanol: water=7:3:1, thereby obtaining 148 mg (32%) of crude title. This was purified by recrystallizing from an ethanol-hexane mixed solvent to obtain 79 mg (17%) of the title compound as light yellow crystals.

$^1$H-NMR (400 MHz, 0.1 mol/1 NaOD) δ: 0.90–1.09 (2H, m), 1.22–1.51 (3H, m), 2.16 (3H, s), 2.34–2.49 (1H, m), 2.99–3.09 (1H, m), 3.35–3.46 (1H, m), 3.46–3.62 (1H, m), 3.62–3.73 (1H, m), 3.78–3.89 (1H, m), 4.79–4.88 (0.5H, m), 4.94–5.04 (0.5H, m), 7.22–7.41 (5H, m), 8.26 (1H, s).

Melting point: 179.4–183.6° C. (decomp.)

Elemental analysis: for $C_{25}H_{26}F_2N_4O_3$

Calcd.: C, 64.09; H, 5.59; N, 11.96. Found: C, 63.91; H, 5.40; N, 11.96.

INVENTIVE EXAMPLE 6

7-[3-(R)-(1-Amino-1-phenylmethyl)-1-pyrrolidinyl]-1-[2-(S)-fluoro-1-(R)-cyclopropyl]-1,4-dihydro-8-methoxy-4-oxoquinoline-3-carboxylic acid [F2]

3-(R)-[1-Tert-butoxycarbonylamino-1-phenylmethyl] pyrrolidine [F2] (304 mg, 1.1 mmol) and triethylamine (1 ml) were added to a dimethyl sulfoxide (5 ml) solution of 7-fluoro-1-[2-(S)-fluoro-1-(R)-cyclopropyl]-1,4-dihydro-8-methoxy-4-oxoquinoline-3-carboxylic acid (266 mg, 0.9 mmol), and the mixture was stirred at 100° C. for 14 hours. The solvent was evaporated under a reduced pressure and the resulting residue was mixed with chloroform (50 ml), this was washed with 10% citric acid (40 ml×2) and water (50 ml) and dried over sodium sulfate, and then the solvent was evaporated. The resulting residue was mixed with concentrated hydrochloric acid (10 ml) and stirred at room temperature for 10 minutes, and then the resulting water layer was washed with chloroform (20 ml×3) and alkalified with 30% sodium hydroxide aqueous solution under ice-cooling. This was adjusted to a liquid property of pH 7.2 by adding concentrated hydrochloric acid and 1 mol/l hydrochloric acid and then extracted with chloroform (80 ml×3). The resulting organic layer was dried over anhydrous sodium sulfate and the solvent was evaporated under a reduced pressure. This was purified by recrystallizing from an ethanol-hexane mixed solvent to obtain 274 mg (67%) of the title compound as light yellow crystals.

$^1$H-NMR (400 MHz, 0.1 mol/1 NaOD) δ: 1.25–1.67 (4H, m), 2.48–2.61 (1H, m), 3.30–3.49 (3H, m), 3.49 (3H, s), 3.61–3.71 (1H, m), 3.71–3.79 (1H, m), 3.94–4.02 (1H, m), 4.88–4.94 (0.5H, m), 5.03–5.10 (0.5H, m), 7.00 (1H, d, J=9.28 Hz), 7.31–7.43 (5H, m), 7.92 (1H, d, J=9.28 Hz), 8.39 (1H, s).

Melting point: 116.8–120.4° C. (decomp.)

Elemental analysis: for $C_{25}H_{26}FN_3O_4 \cdot 0.25H_2O$

Calcd.: C, 65.85; H, 5.86; N, 9.21. Found: C, 66.14; H, 5.80; N, 9.18.

REFERENCE EXAMPLE 8

4-(R)-(2-Methoxy)phenylcarbonyl-1-[1-(R)-phenylethyl]-2-pyrrolidone

In an atmosphere of nitrogen, 1 mol/l 2-methoxyphenyl-magnesium bromide (38 ml) prepared from 2-bromoanisole was added dropwise to tetrahydrofuran solution (50 ml) of N-methyl-N-methoxy-[1-(R)-phenylethyl]-5-oxopyrrolidine-3-carboxamide (6.20 g, 22.4 mol), and the mixture was stirred at room temperature for 5 minutes. The reaction solution was fixed with 1 mol/l hydrochloric acid (40 ml) under ice-cooling and then extracted with ethyl acetate (80 ml×2). The organic layer was washed with saturated brine (100 ml) and dried over anhydrous sodium sulfate. The solvent was evaporated under a reduced pressure and the resulting residue was applied to a silica gel column chromatography. By eluting with a n-hexane:ethyl acetate system of from (1:2) to (1:3), 2.45 g (33%) of the title compound was obtained as a light yellow oil.

$^1$H-NMR (400 MHz, CDCl$_3$) δ: 1.54 (3H, d, J=6.84 Hz), 2.73 (2H, d, J=8.30 Hz), 3.18 (1H, dd, J=8.79, 9.77 Hz), 3.66 (1H, dd, J=9.77 Hz), 3.82 (3H, s), 4.04 (1H, dd, J=6.34, 8.79 Hz), 5.51 (1H, q, J=6.84 Hz), 6.94 (1H, d, J=8.30 Hz), 7.00–7.04 (1H, m), 7.27–7.38 (5H, m), 7.47–7.51 (1H, m), 7.68–7.70 (1H, m).

REFERENCE EXAMPLE 9

4-(R)-[1-Azido-1-(2-methoxy)phenylmethyl]-1-[1-(R)-phenylethyl]-2-pyrrolidone [F1], [F2]

Under ice-cooling, sodium borohydride (150 mg) was added to an ethanol (30 ml) solution of 4-(R)-(2-methoxy)phenylcarbonyl-1-[1-(R)-phenylethyl]-2-pyrrolidone (2.45 g, 7.57 mmol), and the mixture was stirred at the same temperature for 20 minutes. The reaction solution was mixed with water (30 ml), stirred at room temperature for 30 minutes and then extracted with chloroform (80 ml×3). The organic layer was washed with saturated brine (100 ml) and dried over anhydrous sodium sulfate. The solvent was evaporated under a reduced pressure and the resulting residue was applied to a silica gel column chromatography. By eluting with 2% methanol-chloroform, 1.97 g (6.05 mmol) of a synthesis intermediate 4-(R)-[1-(2-methoxy)phenyl-1-hydroxymethyl]-1-[1-(R)-phenylethyl]-2-pyrrolidone was obtained as a colorless oil (1:1 mixture of isomers). This was made into a dichloromethane (35 ml) solution, mixed with methanesulfonyl chloride (900 mg, 7.87 mmol) and triethylamine (1.8 ml) and then stirred at room temperature for 50 hours. The reaction solution was washed with water (30 ml) and saturated brine (50 ml), the organic layer was dried over anhydrous sodium sulfate, and then the solvent was evaporated under a reduced pressure. The resulting residue was dissolved in N,N dimethylformamide (40 ml), mixed with sodium azide (2.11 g) and then heated at 80° C. for 13 hours. After spontaneous cooling, the reaction solution was mixed with water (50 ml) and extracted with ethyl acetate (70 ml×3), and the resulting organic layer was washed with saturated brine (150 ml) and dried over anhydrous sodium sulfate. The solvent was evaporated under a reduced pressure and the resulting residue was applied to a silica gel column chromatography. By eluting with n-hexane:ethyl acetate (2:1), 621 mg (29%) of the low polarity title compound [F1] and 1.0 g (47%) of the high polarity title compound [F2] were obtained in succession each as a colorless oil.

[F1];

$^1$H-NMR (400 MHz, CDCl$_3$) δ: 1.47 (3H, d, J=6.83 Hz), 2.49–2.55 (2H, m), 2.66–2.73 (1H, m), 2.85–2.94 (1H, m), 2.97–3.05 (1H, m), 3.83 (3H, s), 4.95 (1H, d, J=7.81 Hz), 5.49 (1H, q, J=6.83 Hz), 6.92 (1H, d, J=8.30 Hz), 6.97–7.01 (1H, m), 7.23–7.34 (7 H, m). [F2];

$^1$H-NMR (400 MHz, CDCl$_3$) δ: 1.55 (3H, d, J=6.84 Hz), 2.18–2.34 (2H, m), 2.63–2.74 (1H, m), 3.10 (1H, dd, J=8.30, 10.25 Hz), 3.30 (1H, dd, J=6.84, 10.25 Hz), 3.84 (3H, s), 4.94 (1H, d, J=9.28 Hz), 5.49 (1H, q, J=6.84 Hz), 6.92 (1H, d, J=8.30 Hz), 6.98–7.01 (1H, m), 7.25–7.36 (7H, m).

REFERENCE EXAMPLE 10

4-(R)-[1-Tert-butoxycarbonylamino-1-(2-methoxy)phenylmethyl]-1-[1-(R)-phenylethyl]-2-pyrrolidone [F1], [F2]

An ethanol (40 ml) solution of 4-(R)-[1-azido-1-(2-methoxy)phenylmethyl]-1-[1-(R)-phenylethyl]-2-pyrrolidone [F1] (621 mg, 1.77 mmol) was mixed with 10% palladium-carbon catalyst (53.8% moisture, 700 mg) to carry out catalytic hydrogenation at room temperature for 1 hour under ordinary pressure. The reaction solution was filtered and the filtrate was evaporated under a reduced pressure. The resulting residue was dissolved in dichloromethane (40 ml), mixed with di-tert-butyl dicarbonate (600 mg) and triethylamine (1 ml) and then stirred at roan temperature for 15 hours. The reaction solution was evaporated under a reduced pressure, the resulting residue was mixed with chloroform (20 ml) and washed with water (10 ml), and then the organic layer was dried over anhydrous sodium sulfate. The solvent was evaporated under a reduced pressure and the resulting residue was applied to a silica gel column chromatography (silica gel, 20 g). By eluting with n-hexane:ethyl acetate (1:2), 589 mg (78%) of the title compound [F1] was obtained as colorless amorphous.

The same reaction was also carried out regarding 4-(R)-[1-azido-1-(2-methoxy)phenylmethyl]-1-[1-(R)-phenylethyl]-2-pyrrolidone [F2] (80%).

[F1];

$^1$H-NMR (400 MHz, CDCl$_3$) δ: 1.42 (9H, s), 1.47 (3H, d, J=6.84 Hz), 2.50–2.54 (2H, m), 2.70–2.86 (2H, m), 2.92–3.01 (1H, m), 3.82 (3H, s), 4.73–4.80 (1H, m), 5.45–5.56 (2H, m), 6.85–6.93 (2H, m), 7.12–7.30 (7H, m).

[F2];

$^3$H-NMR (400 MHz, CDCl$_3$) δ: 1.41 (9H, s), 1.54 (3H, d, J=7.33 Hz), 2.03–2.15 (2H, m), 2.68–2.81 (1H, m), 3.00–3.13 (1H, m), 3.22–3.35 (1H, m), 3.84 (3H, s), 4.60–4.72 (1H, m), 5.39–5.56 (2H, m), 6.79–6.96 (2H, m), 7.05–7.38 (7H, m).

REFERENCE EXAMPLE 11

3-(R)-[1-Tert-butoxycarbonylamino-1-(2-methoxy)phenylmethyl]-1-[1-(R)-phenylethyl]pyrrolidine [F1], [F2]

In an atmosphere of nitrogen, 1-Mborane-tetrahydrofuran complex (5.5 ml) was added dropwise to a tetrahydrofuran (20 ml) solution of 4-(R)-[1-tert-butoxycarbonylamino-1-(2-methoxy)phenylmethyl]-1-[1-(R)-phenylethyl]-2-pyrrolidone [F1] (589 mg, 1.39 mmol) under ice-cooling, and then the mixture was stirred at room temperature for 17 hours. After adding methanol (10 ml) under ice-cooling and subsequent stirring at room temperature for 20 minutes, the solvent was evaporated under a reduced pressure. The resulting residue was dissolved in 80% hydrous ethanol (40 ml) and heated under reflux for 30 minutes in the presence of triethylamine (3 ml). After spontaneous cooling of the reaction solution, the solvent was evaporated under a reduced pressure, chloroform (30 ml) was added to the resulting residue, and the resulting organic layer was washed with water (10 ml) and saturated brine (10 ml) and dried over anhydrous sodium sulfate. The solvent was evaporated under a reduced pressure and the resulting residue was applied to a silica gel column chromatography. By eluting with 3% methanol-chloroform, 488 mg (86%) of the title compound was obtained as a colorless oil.

The same reaction was also carried out regarding 4-(R)-[1-tert-butoxycarbonylamino-1-(2-methoxy)phenylmethyl]-1-[1-(R)-phenylethyl]-2-pyrrolidone [F2] (99%).

[F1];

$^1$H-NMR (400 MHz, CDCl$_3$) δ: 1.32 (3H, d, J=6.34 Hz), 1.45 (9H, s), 1.66–1.74 (1H, m), 2.18–2.31 (3H, m), 2.70–2.85 (2H, m), 3.11 (1H, q, J=6.34 Hz), 3.79 (3H, s), 4.70 (1H, t, J=7.32 Hz), 6.17 (1H, brd, J=6.35 Hz), 6.80–6.91 (2H, m), 7.17–7.33 (7H, m).

[F2];

¹H-NMR (400 MHz, CDCl₃) δ: 1.40 (3H, d, J=6.83 Hz), 1.45 (9H, s), 1.80–1.92 (1H, m), 2.17–2.30 (2H, m), 2.32–2.42 (1H, m), 2.53–2.61 (1H, m), 2.75–2.82 (1H, m), 2.89–2.98 (1H, m), 3.10–3.18 (1H, m), 3.79 (3H, s), 4.74 (1H, t, J=6.83 Hz), 6.78 (1H, d, J=7.81 Hz), 6.97–7.35 (8H, m).

REFERENCE EXAMPLE 12

3-(R)-[1-Tert-butoxycarbonylamino-1-(2-methoxy) phenylmethyl]pyrrolidine [F1], [F2]

An ethanol (30 ml) solution of 3-(R)-[1-tert-butoxycarbonylamino-1-(2-methoxy)phenylmethyl]-1-[1-(R)-phenylethyl]-2-pyrrolidone [F1] (488 mg, 1.19 mmol) was mixed with 10% palladium carbon catalyst (53.8% moisture, 500 mg) and subjected to 3 hours of catalytic hydrogenation under ordinary pressure while heating at 50° C. The reaction solution was filtered and the filtrate was evaporated under a reduced pressure to obtain 353 mg (97%) of crude title compound as colorless crystals. This was used in the subsequent reaction without purification.

The same reaction was also carried out regarding 3-(R)-[1-tert-butoxycarbonylamino-1-(2-methoxy)phenylmethyl]-1-[1-(R)-phenylethyl]-2-pyrrolidone [F2] (97%).

INVENTIVE EXAMPLE 7

5-Amino-7-[3-(R)-(1-amino-1-(2-methoxy)phenylmethyl)-1-pyrrolidinyl]-6,8-difluoro-1-[2-(S)-fluoro-1-(R)-cyclopropyl]-1,4-dihydro-4-oxoquinoline-3-carboxylic acid [F1]

3-(R)-[1-Tert-butoxycarbonylamino-1-(2-methoxy)phenylmethyl]pyrrolidine [F1] (353 mg, 1.15 mmol) was added to an acetonitrile suspension (15 ml) of 5-amino-6,7,8-trifluoro-1-[2-(S)-fluoro-1-(R)-cyclopropyl]-1,4-dihydro-4-oxoquinoline-3-carboxylic acid (316 mg, 1.0 mmol), and the mixture was heated under reflux for 11 hours in the presence of triethylamine (3 ml). After spontaneous cooling, the solvent of the reaction solution was evaporated under a reduced pressure and the resulting residue was dissolved in chloroform (50 ml). This was washed with 10% citric acid (30 ml×2) and saturated brine (20 ml) and dried over anhydrous sodium sulfate. The solvent was evaporated under a reduced pressure, and the resulting residue was mixed with concentrated hydrochloric acid (3 ml) and stirred at room temperature for 5 minutes. This hydrochloric acid solution was washed with chloroform (20 ml×3), adjusted to an alkaline liquid property by adding 30% sodium hydroxide aqueous solution under ice-cooling and then stirred at room temperature for 1 hour. This suspension was adjusted to a liquid property of pH 7.4 by adding concentrated hydrochloric acid and 1 mol/l hydrochloric acid and then extracted with chloroform (80 ml×3). The resulting organic layer was dried over anhydrous sodium sulfate and the solvent was evaporated under a reduced pressure to obtain 482 mg of crude title compound. This was purified by recrystallizing from a methanol-ethanol mixed solvent to obtain 213 mg of the title compound.

¹H-NMR (400 MHz, 0.1 mol/l NaOD) δ: 1.18–1.38 (2H, m), 1.41–1.55 (1H, m), 2.05–2.18 (1H, m), 2.28–2.40 (1H, m), 2.77–2.88 (1H, m), 3.02–3.16 (1H, m), 3.15–3.33 (2H, m), 3.43–3.52 (1H, m), 3.64 (3H, s), 3.78–3.85 (1H, m), 4.48–4.55 (0.5H, m), 4.65–4.73 (0.5H, m), 6.84–6.88 (2H, m), 7.12–7.20 (2H, m), 8.08 (1H, s).

Melting point: 114.8–126.6° C.

Elemental analysis: for $C_{25}H_{25}F_3N_4O_4 \cdot 1.25H_2O$

Calcd.: C, 57.19; H, 5.28; N, 10.67. Found: C, 57.18; H, 5.12; N, 10.61.

INVENTIVE EXAMPLE 8

5-Amino-7-[3-(R)-(1-amino-1-(2-methoxy)phenylmethyl)-1-pyrrolidinyl]-6,8-difluoro-1-[2-(S)-fluoro-1-(R)-cyclopropyl]-1,4-dihydro-4-oxoquinoline-3-carboxylic acid [F2]

3-(R)-[1-Tert-butoxycarbonylamino-1-(2-methoxy)phenylmethyl]pyrrolidine [F2] (353 mg, 1.15 mmol) was added to an acetonitrile suspension (15 ml) of 5-amino-6,7,8-trifluoro-1-[2-(S)-fluoro-1-(R)-cyclopropyl]-1,4-dihydro-4-oxoquinoline-3-carboxylic acid (316 mg, 1.0 mmol), and the mixture was heated under reflux for 11 hours in the presence of triethylamine (3 ml). After spontaneous cooling, the solvent of the reaction solution was evaporated under a reduced pressure and the resulting residue was dissolved in chloroform (50 ml). This was washed with 10% citric acid (30 ml×2) and saturated brine (20 ml) and dried over anhydrous sodium sulfate. The solvent was evaporated under a reduced pressure, and the resulting residue was mixed with concentrated hydrochloric acid (3 ml) and stirred at room temperature for 5 minutes. This hydrochloric acid solution was washed with chloroform (20 ml×3), adjusted to an alkaline liquid property by adding 30% sodium hydroxide aqueous solution under ice-cooling and then stirred at room temperature for 1 hour. This suspension was adjusted to a liquid property of pH 7.4 by adding concentrated hydrochloric acid and 1 mol/l hydrochloric acid and then extracted with chloroform (80 ml×3). The resulting organic layer was dried over anhydrous sodium sulfate and the solvent was evaporated under a reduced pressure to obtain 468 mg of crude title compound. This was purified by recrystallizing from a methanol-ethanol mixed solvent to obtain 226 mg of the title compound.

¹H-NMR (400 MHz, 0.1 mol/l NaOD) δ: 1.05–1.48 (4H, m), 2.19–2.38 (1H, m), 3.05–3.58 (5H, m), 3.52 (3H, s), 3.72–3.80 (1H, m), 4.52–4.60 (0.5H, m), 4.70–4.79 (0.5H, m), 6.65–6.80 (2H, m), 6.94–7.10 (2H, m), 8.12 (1H, s).

Melting point: 251.1–253.2° C.

Elemental analysis: for $C_{25}H_{25}F_3N_4O_4$

Calcd.: C, 59.76; H, 5.01; N, 11.15. Found: C, 59.89; H, 5.05; N, 11.12.

REFERENCE EXAMPLE 13

4-(R)-(2,4-Difluoro)phenylcarbonyl-1-[1-(R)-phenylethyl]-2-pyrrolidone

In an atmosphere of nitrogen, 1 mol/l of 2,4-difluorophenylmagnesium bromide (54.3 ml) prepared from 2,4-difluorobromobenzene was added dropwise to a tetrahydrofuran solution (110 ml) of N-methyl-N-methoxy-[1-(R)-phenylethyl]-5-oxopyrrolidine-3-carboxamide (5.50 g, 19.9 mmol), and the mixture was stirred at 50° C. for 4 hours. The reaction solution was mixed with 1 mol/l hydrochloric acid (150 ml) under ice-cooling and extracted with ethyl acetate (150 ml×2), and then the organic layer was washed with saturated brine (100 ml) and dried over anhydrous sodium sulfate. The solvent was evaporated under a reduced pressure and the resulting residue was applied to a silica gel column chromatography. By eluting with a n-hexane:ethyl acetate system of from (2:1) to (1:1), 2.00 g (29%) of the title compound was obtained as a light yellow oil.

$^1$H-NMR (400 MHz, CDCl$_3$) δ: 1.55 (3H, d, J=6.83 Hz), 2.70–2.85 (2H, m), 3.21 (1H, t, J=9.28 Hz), 3.71–3.75 (1H, m), 3.85–3.90 (1H, m), 5.52 (1H, q, J=6.83 Hz), 6.85–6.91 (1H, m), 6.98–7.03 (1H, m), 7.26–7.92 (5H, m), 7.94–7.97 (1H, m).

REFERENCE EXAMPLE 14

4-(R)-[1-Azido-1-(2,4-difluoro)phenylmethyl-1-[1-(R)-phenylethyl]-2-pyrrolidone [F1], [F2]

Under ice-cooling, sodium borohydride (332 mg, 8.77 mmol) was added to a methanol (60 ml) solution of 4-(R)-(2,4-difluoro)phenylcarbonyl-1-[1-(R)-phenylethyl]-2-pyrrolidone (2.89 g, 8.78 mmol), and the mixture was stirred at the same temperature for 30 minutes. The reaction solution was mixed with saturated ammonium chloride aqueous solution (3 ml) and stirred at room temperature for 30 minutes. The reaction mixture was extracted with ethyl acetate (80 ml×3), and the organic layer was washed with saturated brine (100 ml) and dried over anhydrous sodium sulfate. The solvent was evaporated under a reduced pressure and the resulting residue was applied to a silica gel column chromatography. By eluting with a n-hexane:ethyl acetate system of from (2:1) to (1:2), 2.09 g (72%) of a synthesis intermediate 4-(R)-[1-(2,4-difluoro)phenyl-1-hydroxymethyl]-1-[1-(R)-phenylethyl]-2-pyrrolidone was obtained as a colorless oil (1:1 mixture of isomers). A 1.76 g (5.30 mmol) portion of this was dissolved in dichloromethane (35 ml), and the solution was mixed with triethylamine (1.04 ml, 7.46 mmol) and methanesulfonyl chloride (492 µl, 6.36 mmol) under ice-cooling and then stirred at the same temperature for 30 minutes. The reaction solution was washed with saturated ammonium chloride aqueous solution (30 ml) and saturated brine (50 ml), the organic layer was dried over anhydrous sodium sulfate, and then the solvent was evaporated under a reduced pressure. The resulting residue was dissolved in N,N-dimethylformamide (17 ml), mixed with sodium azide (862 mg, 13.3 mmol) and then heated at 50° C. for 14 hours. After spontaneous cooling, the reaction solution was mixed with water (50 ml) and extracted with ethyl acetate (70 ml×2), and the resulting organic layer was washed with water (50 ml×3) and saturated brine (150 ml) and dried over anhydrous sodium sulfate. The solvent was evaporated under a reduced pressure and the resulting residue was applied to a silica gel column chromatography. By eluting with n-hexane:ethyl acetate (2:1), 913 mg (40%) of the low polarity title compound [F1] and 894 mg (39%) of the high polarity title compound [F2] were obtained in succession each as a colorless oil.

[F1]
$^1$H-NMR (400 MHz, CDCl$_3$) δ: 1.49 (3H, d, J=7.32 Hz), 2.53–2.65 (3H, m), 2.86–2.91 (1H, m), 2.96–2.99 (1H, m), 4.77 (1H, d, J=8.30 Hz), 5.49 (1H, q, J=7.32 Hz), 6.85–6.90 (1H, m), 6.93–6.97 (1H, m), 7.23–7.36 (6H, m).

[F2]
$^1$H-NMR (400 MHz, CDCl$_3$) δ: 1.55 (3H, d, J=7.32 Hz), 2.17 (1H, dd, J=8.06, 16.85 Hz), 2.31 (1H, dd, J=9.04, 16.85 Hz), 2.61–2.67 (1H, m), 3.13 (1H, dd, J=8.06, 10.25 Hz), 3.29 (1H, dd, J=6.35, 10.25 Hz), 4.75 (1H, d, J=9.28 Hz), 5.49 (1H, q, J=7.32 Hz), 6.65–6.91 (1H, m), 6.93–6.97 (1H, m), 7.26–7.36 (6H, m).

REFERENCE EXAMPLE 15

4-(R)-[1-Tert-butoxycarbonylamino-1-(2,4-difluoro)phenylmethyl]-1-[1-(R)-phenylethyl]-2-pyrrolidone [F1], [F2]

An ethanol (20 ml) solution of 4-(R)-[1-azido-1-(2,4-difluoro)phenylmethyl]-1-[1-(R)-phenylethyl]-2-pyrrolidone [F1] (913 mg, 2.56 mmol) was mixed with 10% palladium-carbon catalyst (53.8% moisture, 900 mg) to carry out catalytic hydrogenation at room temperature for 1 hour under ordinary pressure. The reaction solution was filtered and the solvent of the filtrate was evaporated under a reduced pressure. The resulting residue was dissolved in dichloroethane (20 ml), mixed with di-tert-butyl dicarbonate (647 µl, 2.82 mmol) and triethylamine (464 µl, 3.33 mmol) and then stirred at room temperature for 24 hours. The reaction solution was evaporated under a reduced pressure, and the resulting residue was applied to a silica gel column chromatography. By eluting with n-hexane:ethyl acetate (1:1), 567 mg (52%) of the title compound [F1] was obtained as colorless amorphous.

The same reaction was also carried out regarding 4-(R)-[1-azido-1-(2,4-difluoro)phenylmethyl]-1-[1-(R)-phenylethyl]-2-pyrrolidone [F2] (84%).

[F1];
$^1$H-NMR (400 MHz, CDCl$_3$) δ: 1.41 (9H, s), 1.48 (3H, d, J=6.84 Hz), 2.44–2.95 (5H, m), 4.78–4.80 (1H, m), 5.04–5.07 (1H, m), 5.49 (1H, q, J=6.84 Hz), 6.78–6.87 (2H, m), 7.18–7.32 (6H, m). [F2];
$^1$H-NMR (400 MHz, CDCl$_3$) δ: 1.40 (9H, s), 1.55 (3H, d, J=7.33 Hz), 2.08 (1H, dd, J=8.06, 17.09 Hz), 2.22 (1H, dd, J=8.79, 17.09 Hz), 2.65–2.67 (1H, m), 3.10–3.14 (1H, m), 3.25–3.29 (1H, m), 4.70–4.72 (1H, m), 4.99–5.01 (1H, m), 5.49 (1H, q, J=7.33 Hz), 6.79–6.89 (2H, m), 7.26–7.37 (6H, m).

REFERENCE EXAMPLE 16

3-(R)-[1-Tert-butoxycarbonylamino-1-(2,4-difluoro)phenylmethyl]-1-[1-(R)-phenylmethyl]pyrrolidine [F1], [F2]

In an atmosphere of nitrogen, 1Mborane-tetrahydrofuran complex (9.60 ml) was added dropwise to a tetrahydrofuran solution (12 ml) of 4-(R)-[1-tert-butoxycarbonylamino-1-(2,4-difluoro)phenylmethyl]-1-[1-(R)-phenylethyl]-2-pyrrolidone [F1] (560 mg, 1.30 mmol) under ice-cooling, and then the mixture was stirred at room temperature for 17 hours. After evaporation of the solvent under a reduced pressure, the resulting residue was dissolved in 80% hydrous ethanol (10 ml) and heated under reflux for 1 hour in the presence of triethylamine (1 ml). After spontaneous cooling of the reaction solution, the solvent was evaporated under a reduced pressure, chloroform (30 ml) was added to the resulting residue, and then the resulting organic layer was washed with saturated ammonium chloride aqueous solution (10 ml) and saturated brine (10 ml) and dried over anhydrous sodium sulfate. The solvent was evaporated under a reduced pressure and the resulting residue was applied to a silica gel column chromatography. By eluting with n-hexane:ethyl acetate (1:1), 485 mg (90%) of the title compound was obtained as a colorless oil.

The same reaction was also carried out regarding 4-(R)-[1-tert-butoxycarbonylamino-1-(2,4-difluoro)phenylmethyl]-1-[1-(R)-phenylethyl]-2-pyrrolidone [F2] (82%).

[F1];
¹H-NMR (400 MHz, CDCl₃) δ: 1.37 (3H, d, J=6.84 Hz), 1.48 (9H, s), 1.67–1.69 (1H, m), 2.20–2.24 (1H, m), 2.36–2.39 (1H, m), 2.57–2.59 (1H, m), 3.01–3.15 (2H, m), 4.67–4.72 (1H, m), 6.35–6.39 (1H, m), 6.71–6.83 (2H, m), 7.22–7.36 (6H, m).

[F2];
¹H-NMR (400 MHz, CDCl₃) δ: 1.41 (3H, d, J=6.84 Hz), 1.48 (9H, s), 1.74–1.76 (1H, m), 2.01–2.04 (2H, m), 2.19–2.23 (1H, m), 2.35–2.44 (1H, m), 3.14–3.17 (2H, m), 4.71–4.73 (1H, m), 6.68–6.70 (1H, m), 6.89–6.95 (2H m), 7.26–7.34 (6H, m).

REFERENCE EXAMPLE 17

3-(R)-[1-Tert-butoxycarbonylamino-1-(2,4-difluoro)phenylmethyl]pyrrolidine [F1], [F2]

An ethanol (10 ml) solution of 3-(R)-[1-tert-butoxycarbonylamino-1-(2,4-difluoro)phenylmethyl]-1-[1-(R)-phenylethyl]-2-pyrrolidone [F1] (243 mg, 0.58 mmol) was mixed with 10% palladium-carbon catalyst (53.8% moisture, 245 mg) and subjected to 2 hours of catalytic hydrogenation under ordinary pressure while heating at 50° C. The reaction solution was filtered and the solvent of the filtrate was evaporated under a reduced pressure to obtain 200 mg of the crude title sound as colorless crystals. This was used in the subsequent reaction without purification.

The same reaction was also carried out regarding 3-(R)-[1-tert-butoxycarbonylamino-1-(2,4-difluoro)phenylmethyl)-1-[1-(R)-phenylethyl]pyrrolidine [F2].

INVENTIVE EXAMPLE 9

5-Amino-7-[3-(R)-(1-amino-1-(2,4-difluoro)phenylmethyl)-1-pyrrolidinyl]-6,8-difluoro-1-[2-(S)-fluoro-1-(R)-cyclopropyl]-1,4-dihydro-4-oxoquinoline-3-carboxylic acid [F1]

3-(R)-[1-Tert-butoxycarbonylamino-1-(2,4-difluoro)phenylmethyl]pyrrolidine [F1] (0.58 mmol) was added to an acetonitrile suspension (10 ml) of 5-amino-6,7,8-trifluoro-1-[2-(S)-fluoro-1-(R)-cyclopropyl]-1,4-dihydro-4-oxoquinoline-3-carboxylic acid (183 mg, 0.58 mmol), and the mixture was heated under reflux for 15 hours in the presence of triethylamine (0.5 ml). After spontaneous cooling, the solvent of the reaction solution was evaporated under a reduced pressure. The resulting residue was dissolved in chloroform (50 ml), this was washed with 10% citric acid (30 ml) and saturated brine (20 ml) and dried over anhydrous sodium sulfate, and then the solvent was evaporated under a reduced pressure. The resulting residue was mixed with concentrated hydrochloric acid (5 ml) under ice-cooling, further mixed with 1 mol/l hydrochloric acid aqueous solution (5 ml) at room temperature and then washed with chloroform (50 ml×3), and the insoluble matter was removed by filtration. This hydrochloric acid solution was adjusted to an alkaline liquid property by adding 10 mol/l sodium hydroxide aqueous solution under ice-cooling and then stirred at room temperature for 1 hour. This suspension was adjusted to a liquid property of pH 7.4 by adding concentrated hydrochloric acid and 1 mol/l hydrochloric acid and then extracted with chloroform (80 ml×3). The resulting organic layer was dried over anhydrous sodium sulfate and the solvent was evaporated under a reduced pressure to obtain the crude title compound as light yellow crystals. This was purified by recrystallizing from ethanol to obtain 125 mg (42%) of the title compound.

¹H-NMR (400 MHz, CDCl₃) δ: 1.40–1.51 (2H, m), 1.84–1.89 (1H, m), 2.28–2.29 (1H, m), 2.57–2.59 (1H, m), 3.35–3.90 (5H, m), 4.13 (1H, d, J=9.28 Hz), 4.79 (1H, brd, J=62.50 Hz), 6.38 (1H, s), 6.79–6.91 (2H, m), 7.37–7.41 (1H, m), 8.51 (1H, s).

Melting point: 182–183° C.
Elemental analysis: for C₂₄H₂₁F₅N₄O₃·0.25H₂O
Calcd.: C, 56.20; H, 4.22; N, 10.92. Found: C, 56.30; H, 4.39; N, 10.77.

INVENTIVE EXAMPLE 10

5-Amino-7-[3-(R)-(1-amino-1-(2,4-difluoro)phenylmethyl)-1-pyrrolidinyl]-6,8-difluoro-1-[2-(S)-fluoro-1-(R)-cyclopropyl]-1,4dihydro-4-oxoquinoline-3-carboxylic acid [F2]

3-(R)-[1-Tert-butoxycarbonylamino-1-(2,4-difluoro)phenylmethyl]pyrrolidine [F2] (0.50 mmol) was added to an acetonitrile suspension (7 ml) of 5-amino-6,7,8-trifluoro-1-[2-(S)-fluoro-1-(R)-cyclopropyl]-1,4-dihydro-4-oxoquinoline-3-carboxylic acid (158 mg, 0.50 mmol), and the mixture was heated under reflux for 15 hours in the presence of triethylamine (0.5 ml). After spontaneous cooling, the solvent of the reaction solution was evaporated under a reduced pressure. The resulting residue was dissolved in chloroform (50 ml), this was washed with 10% citric acid (30 ml) and saturated brine (20 ml) and dried over anhydrous sodium sulfate, and then the solvent was evaporated under a reduced pressure. The resulting residue was mixed with concentrated hydrochloric acid (5 ml) under ice-cooling, further mixed with 1 mol/l hydrochloric acid aqueous solution (5 ml) at room temperature and then washed with chloroform (50 ml×3), and the insoluble matter was removed by filtration. This hydrochloric acid solution was adjusted to an alkaline liquid property by adding 10 mol/l sodium hydroxide aqueous solution under ice-cooling and then stirred at room temperature for 1 hour. This suspension was adjusted to a liquid property of pH 7.4 by adding concentrated hydrochloric acid and 1 mol/l hydrochloric acid and then extracted with chloroform (80 ml×3). The resulting organic layer was dried over anhydrous sodium sulfate and the solvent was evaporated under a reduced pressure to obtain the crude title compound as light yellow crystals. This was purified by recrystallizing from ethanol to obtain 165 mg (65%) of the title compound.

¹H-NMR (400 MHz, CDCl₃) δ: 1.53–1.60 (3H, m), 1.69–1.71 (1H, m), 2.52–2.58 (1H, m), 3.66–3.91 (5H, m), 4.08 (1H, d, J=9.76 Hz), 4.83 (1H, brd, J=62.75 Hz), 6.42 (1H, s), 6.80–6.93 (2H, m), 7.34–7.40 (1H, m), 8.54 (1H, s).

Melting point: 218–220° C. (decoup.)
Elemental analysis: for C₂₄H₂₁F₅N₄O₃
Calcd.: C, 56.69; H, 4.16; N, 11.02. Found: C, 56.20; H, 4.22; N, 10.92.

REFERENCE EXAMPLE 18

4-(R)-(2-Furyl)carbonyl-1-[1-(R)-phenylethyl]-2-pyrrolidone

In an atmosphere of nitrogen, 0.5 mol/l of 2-furylmagnesium bromide (180 ml) prepared from furan was added dropwise to a tetrahydrofuran solution (160 ml) of N-methyl-N-methoxy-1-[1-(R)-phenylethyl]-5-oxopyrrolidine-3-carboxamide (8.30 g, 30.0 mmol), and the mixture was stirred for 30 minutes. The reaction solution was mixed with 1 mol/l hydrochloric acid (200 ml) under ice-cooling and extracted with ethyl acetate (200 ml×2), and then the organic layer was washed with saturated brine (100 ml) and dried over anhydrous sodium sulfate. The solvent was evaporated under a reduced pressure and the resulting residue was applied to a silica gel column chromatography. By eluting with a n-hexane:ethyl acetate system of from (1:1) to (1:2), 3.94 g (46%) of the title compound was obtained as a light yellow oil.

$^1$H-NMR (400 MHz, CDCl$_3$) δ: 1.55 (3H, d, J=6.84 Hz), 2.72–2.87 (2H, m), 3.20–3.25 (1H, m), 3.67 (1H, dd, J=6.83, 9.77 Hz), 3.80–3.89 (1H, m), 5.53 (1H, q, J=6.84 Hz), 6.57 (1H, dd, J=1.46, 3.42 Hz), 7.18–7.38 (6H, m), 7.60 (1H, d, J=0.98 Hz).

REFERENCE EXAMPLE 19

4-(R)-[1-Amino-1-(2-furyl)methyl]-1-[1-(R)-phenylethyl]-2-pyrrolidone [F1], [F2]

Under ice-cooling, sodium borohydride (522 mg, 13.8 mmol) was added to a methanol (80 ml) solution of 4-(R)-(2-furyl)carbonyl-1-[1-(R)-phenylethyl]-2-pyrrolidone (3.90 g, 13.8 mmol), and the mixture was stirred at the same temperature for 30 minutes. The reaction solution was mixed with saturated ammonium chloride aqueous solution (50 ml), stirred at room temperature for 30 minutes and then extracted with chloroform (100 ml×3). The organic layer was washed with saturated brine (100 ml) and dried over anhydrous sodium sulfate. The solvent was evaporated under a reduced pressure and the resulting residue was applied to a silica gel column chromatography. By eluting with toluene:ethyl acetate (1:2), 3.64 g (12.7 mmol) of a synthesis intermediate 4-(R)-[1-(2-furyl)-1-hydroxymethyl]-1-[1-(R)-phenylethyl]-2-pyrrolidone was obtained as a colorless oil (1:1 mixture of isomers). This was made into a dichloromethane (90 ml) solution, mixed with triethylamine (5.97 ml, 42.8 mmol) and methanesulfonyl chloride (2.83 ml, 36.7 mol) under ice-cooling and then stirred at room temperature for 24 hours. The reaction solution was washed with saturated ammonium chloride aqueous solution (100 ml) and saturated brine (100 ml), the organic layer was dried over anhydrous sodium sulfate, and then the solvent was evaporated under a reduced pressure. The resulting residue was dissolved in N,N-dimethylformamide (45 ml), mixed with sodium azide (4.97 g, 76.45 mmol) and then heated at 50° C. for 3 hours. After ice-cooling, the reaction solution was mixed with water (100 ml) and extracted with ethyl acetate (100 ml×2), and the resulting organic layer was washed with water (80 ml×3) and saturated brine (100 ml) and dried over anhydrous sodium sulfate. The solvent was evaporated under a reduced pressure and the resulting residue was applied to a silica gel column chromatography. By eluting with n-hexane:ethyl acetate (2:1) to (1:1), 4.02 g (12.7 mmol) of a synthesis intermediate 4-(R)-[1-azido-1-(2-furyl)methyl]-1-[1-(R)-phenylethyl]-2-pyrrolidone was obtained as a colorless oil (1:1 mixture of isomers). This was made into an ethanol (100 ml) solution and mixed with 10% palladium-carbon catalyst (53.8% moisture, 4.80 mg), and then catalytic hydrogenation was carried out at roam temperature for 2 hours under ordinary pressure. The reaction solution was filtered and the solvent of the resulting filtrate was evaporated under a reduced pressure. The resulting residue was applied to a silica gel column chromatography. By eluting with a chloroform:methanol system of from (98:2) to (95:5), 1.42 g (39%) of the low polarity title compound [F2] and 1.75 g (49%) of the high polarity title compound [F1] were obtain in succession each as a colorless oil.

[F1];
$^1$H-NMR (400 MHz, CDCl$_3$)δ: 1.46 (3H, d, J=6.84 Hz), 2.47–2.65 (3H, m), 2.93–2.91 (1H, m), 3.13 (1H, dd, J=5.86, 9.76 Hz), 3.87 (1H, d, J=6.84 Hz), 5.46 (1H, q, J=6.84 Hz), 6.14 (1H, d, J=2.93 Hz), 6.29–6.31 (1H, m), 7.26–7.34 (6H, m).

[F2];
$^1$H-NMR (400 MHz, CDCl$_3$) δ: 1.50 (3H, d, J=7.32 Hz), 2.28 (1H, dd, J=7.81, 17.09 Hz), 2.41 (1H, dd, J=8.79, 17.09 Hz), 2.54–2.59 (1H, m), 3.17 (1H, dd, J=8.30, 10.01 Hz), 3.32 (1H, dd, J=6.35, 10.01 Hz), 3.79 (1H, d, J=8.30 Hz), 5.48 (1H, q, J=7.32 Hz), 6.13 (1H, d, J=2.93 Hz), 6.30 (1H, dd, J=1.96, 2.93 Hz), 7.26–7.36 (6H, m).

REFERENCE EXAMPLE 20

4-(R)-[1-Tert-butoxycarbonylamino-1-(2-furyl)methyl]-1-[1-(R)-phenylethyl]-2-pyrrolidone [F1], [F2]

A dichloromethane (40 ml) solution of 4-(R)-[1-amino-1-(2-furyl)methyl]-1-[1-(R)-phenylethyl]-2-pyrrolidone [F1] (2.00 g, 7.03 mmol) was mixed with di-tert-butyl dicarbonate (1.95 ml, 8.44 mmol) and triethylamine (1.38 ml, 9.84 mmol) and stirred at room temperature for 8 hours. The reaction solution was concentrated under a reduced pressure, and the resulting residue was applied to a silica gel column chromatography. By eluting with n-hexane:ethyl acetate (1:1), 2.32 g (86%) of the title compound [F1] was obtained as colorless amorphous.

The same reaction was also carried out regarding 4-(R)-[1-amino-1-(2-furyl)methyl]-1-(1-(R)-phenylethyl]-2-pyrrolidone [F2] (78%).

[F1];
$^1$H-NMR (400 MHz, CDCl$_3$) δ: 1.44 (9H, s), 1.47 (3H, d, J=7.32 Hz), 2.43 (1H, dd, J=7.08, 17.33 Hz), 2.56 (1H, dd, J=9.04, 17.33 Hz), 2.44–2.77 (1H, m), 2.97–2.99 (1H, m), 3.12–3.14 (1H, m), 4.82–4.92 (2H, m), 5.47 (1H, q, J=7.32 Hz), 6.18 (1H, d, J=3.41 Hz), 6.29–6.31 (1H, m), 7.26–7.33 (6H, m).

[F2];
$^1$H-NMR (400 MHz, CDCl$_3$) δ: 1.43 (9H, s), 1.49 (3H, d, J=6.84 Hz), 2.27 (1H, dd, J=7.32, 17.09 Hz), 2.41 (1H, dd, J=8.79, 17.09 Hz), 2.67–2.69 (1H, m), 3.05–3.06 (1H, m), 3.23 (1H, dd, J=5.86, 10.25 Hz), 4.75–4.84 (2H, m), 5.47 (1H, q, J=6.84 Hz), 6.21 (1H, s), 6.31 (1H, dd, J=1.95, 2.93 Hz), 7.26–7.36 (6H, m).

REFERENCE EXAMPLE 21

3-(R)-[1-Tert-butoxycarbonylamino-1-(2-furyl)methyl]-1-[1-(R)-phenylethyl]-2-pyrrolidone [F1], [F2]

In an atmosphere of nitrogen, 1Mborane-tetrahydrofuran complex (14.8 ml) was added dropwise to a tetrahydrofuran solution (40 ml) of 4-(R)-[1-tert-butoxycarbonylamino-1-(2-furyl)methyl]-1-[1-(R)-phenylethyl]-2-pyrrolidone [F1] (2.03 g, 5.28 mmol) under ice-cooling, and then the mixture was stirred at room temperature for 17 hours. After evaporation of the solvent under a reduced pressure, the resulting residue was dissolved in 80% hydrous ethanol (40 ml) and heated under reflux for 1 hour in the presence of triethylamine (1 ml). After spontaneous cooling of the reaction solution, the solvent was evaporated under a reduced pressure, chloroform (100 ml) was added to the resulting residue, and then the resulting organic layer was washed with saturated ammonium chloride aqueous solution (80 ml) and saturated brine (80 ml) and dried over anhydrous sodium sulfate. The solvent was evaporated under a reduced pressure and the resulting residue was applied to a silica gel column chromatography. By eluting with chloroform to chloroform:methanol (97:3), 1.54 g (79%) of the title compound was obtained as white crystals.

The same reaction was also carried out regarding 4-(R)-[1-tert-butoxycarbonylamino-1-(2-furyl)methyl]-1-[1-(R)-phenylethyl]-2-pyrrolidone [F2] (63%).

[F1];
$^1$H-NMR (400 MHz, CDCl$_3$) δ: 1.35 (3H, d, J=6.84 Hz), 1.47 (9H, s), 1.67–1.73 (1H, m), 1.83–1.85 (1H, m), 2.25–2.31 (3H, m), 2.45–2.47 (1H, m), 2.60–2.62 (1H, m), 2.76–2.78 (1H, m), 3.13–3.15 (1H, m), 4.60–4.62 (1H, m), 5.64–5.66 (1H, m), 6.13 (1H, s), 6.27 (1H, dd, J=1.965, 2.93 Hz), 7.22–7.31 (6H, m).
$^1$H-NMR (400 MHz, CDCl$_3$) δ: 1.38 (3H, d, J=6.34 Hz), 1.46 (9H, s), 1.63–1.65 (1H, m), 1.90–1.99 (1H, m), 2.30–2.59 (4H, m), 2.85–2.87 (1H, m), 3.16–3.18 (1H, m), 4.60–4.62 (1H, m), 6.01 (1H, s), 6.22 (1H, dd, J=1.95, 2.93 Hz), 7.23–7.32 (6H, m).

REFERENCE EXAMPLE 22

3-(R)-[1-Tert-butoxycarbonylamino-1-(2-furyl)methyl]-1-benzyloxycarbonylpyrrolidine [F1], [F2]

In an atmosphere of nitrogen, benzyl chloroformate (761 μl, 5.31 mmol) was added dropwise to a dichloroethane solution (15 ml) of 3-(R)-[1-tert-butoxycarbonylamino-1-(2-furyl)methyl]-1-[1-(R)-phenylethyl]-2-pyrrolidone [F1] (658 mg, 1.77 mmol) under ice-cooling and then the m was heated under refulx for 30 hours. After evaporation of the solvent under a reduced pressure, the residue was applied to a silica gel column chromatography. By eluting with chloroform to chloroform:methanol (97:3), 526 mg (74%) of the title compound was obtained as white crystals.

The same reaction was also carried out regarding 3-(R)-[1-tert-butoxycarbonylamino-1-(2-furyl)methyl]-1-[1-(R)-phenylethyl]pyrrolidine [F2] (quantitative).

[F1];
$^1$H-NMR (400 MHz, CDCl$_3$) δ: 1.43 (9H, s), 1.76–1.87 (1H, m), 2.03–2.05 (1H, m), 2.55–2.65 (1H, m), 3.05–3.13 (1H, m), 3.32–3.59 (2H, m), 4.70–4.72 (1H, m), 4.92–4.94 (1H, m), 5.11 (2H, s), 6.18 (1H, s), 6.31 (1H, s), 7.26–7.38 (6H, m).

[F2];
$^1$H-NMR (400 MHz, CDCl$_3$) δ: 1.43 (9H, s), 1.58–1.61 (1H, m), 1.84–1.86 (1H, m), 2.26–2.29 (1H, m), 3.24–3.34 (2H, m), 3.52–3.64 (2H, m), 4.76–4.78 (1H, m), 4.89–4.91 (1H, m), 5.13 (2H, s), 6.19 (1H, s), 6.30 (1H, s), 7.26–7.36 (6H, m).

REFERENCE EXAMPLE 23

3-(R)-[1-Tert-butoxycarbonylamino-1-(2-furyl)methyl]pyrrolidine [F1], [F2]

An ethanol (10 ml) solution of 3-(R)-[1-tert-butoxycarbonylamino-1-(2-furyl)methyl]-1-benzyloxycarbonylpyrrolidine [F1] (507 mg, 1.37 tool) was mixed with 10% palladium-carbon catalyst (53.8% moisture, 500 mg), and catalytic hydrogenation was carried out at room temperature for 4 hours under ordinary pressure. The reaction solution was filtered and the solvent of the filtrate was evaporated under a reduced pressure to obtain 358 mg of the crude title compound as colorless crystals. This was used in the subsequent reaction without purification.

The same reaction was also carried out regarding 3-(R)-[1-tert-butoxycarbonylamino-1-(2-furyl)methyl]-1-benzyloxycarbonylpyrrolidine [F2].

INVENTIVE EXAMPLE 11

5-Amino-7-{3-(R)-[1-amino-1-(2-furyl)methyl]-1-pyrrolidinyl}-6,8-difluoro-1-[2-(S)-fluoro-1-(R)-cyclopropyl]-1,4-dihydro-4-oxoquinoline-3-carboxylic acid [F1]

3-(R)-[1-Tert-butoxycarbonylamino-1-(2-furyl)methyl]pyrrolidine [F1] (1.30 mmol) was added to an acetonitrile suspension (10 ml) of 5-amino-6,7,8-trifluoro-1-[2-(S)-fluoro-1-(R)-cyclopropyl]-1,4-dihydro-4-oxoquinoline-3-carboxylic acid (316 mg, 1.00 mmol), and the mixture was heated under reflux for 19 hours in the presence of triethylamine (0.5 ml). After cooling, the solvent of the reaction solution was evaporated under a reduced pressure. The resulting residue was dissolved in chloroform (150 ml), this was washed with 10% citric acid (80 ml) and saturated brine (80 ml) and dried over anhydrous sodium sulfate, and then the solvent was evaporated under a reduced pressure. The resulting residue was mixed with concentrated hydrochloric acid (10 ml) under ice-cooling, further mixed with 1 mol/l hydrochloric acid aqueous solution (5 ml) at roam temperature and then washed with chloroform (50 ml×4), and the insoluble matter was read by filtration. This hydrochloric acid aqueous solution was adjusted to an alkaline liquid property by adding 10 mol/l sodium hydroxide aqueous solution under ice-cooling and then stirred at room temperature for 1 hour. This suspension was adjusted to a liquid property of pH 7.4 by adding concentrated hydrochloric acid and 1 mol/l hydrochloric acid and then extracted with chloroform (150 ml×3). The resulting organic layer was dried over anhydrous sodium sulfate and the solvent was evaporated under a reduced pressure to obtain the crude title compound as light yellow crystals. This was purified by recrystallizing from ethanol to obtain 294 mg (64%) of the title compound $^1$H-NMR (400 MHz, 0.1 mol/l NaOD) δ: 1.34–1.56 (3H, m), 2.35–2.39 (1H, m), 2.06–2.08 (1H, m), 3.18–3.20 (2H, m), 3.40–3.42 (1H, m), 3.48–3.50 (1H, m), 3.58–3.60 (1H, m), 3.69 (1H, d, J=9.28 Hz), 4.76 (1H, br. d, J=62.50 Hz), 6.18 (1H, d, J=3.42 Hz), 6.34 (1H, s), 7.37 (1H, s), 8.07 (1H, s).

Melting point: 188–189° C.
Elemental analysis: for $C_{22}H_{21}F_3N_4O_4$
Calcd.: C, 57.14; H, 4.58; N, 12.12. Found: C, 57.14; H, 4.78; N, 12.07.

INVENTIVE EXAMPLE 12

5-Amino-7-{3-(R)-[1-amino-1-(2-furyl)methyl]-1-pyrrolidinyl}-6,8-difluoro-1-[2-(S)-fluoro-1-(R)-cyclopropyl]-1,4-dihydro-4-oxoquinoline-3-carboxylic acid [F2]

3-(R)-[1-Tert-butoxycarbonylamino-1-(2-furyl)methyl]pyrrolidine [F2] (0.749 mmol) was added to an acetonitrile suspension (10 ml) of 5-amino-6,7,8-trifluoro-1-[2-(S)-fluoro-1-(R)-cyclopropyl]-1,4-dihydro-4-oxoquinoline-3-carbolic acid (215 mg, 0.681 mmol), and the mixture was heated under reflux for 19 hours in the presence of triethylamine (0.5 ml). After cooling, the solvent of the reaction solution was evaporated under a reduced pressure. The resulting residue was dissolved in chloroform (150 ml), this was washed with 10% citric acid (80 ml) and saturated brine (80 ml) and dried over anhydrous sodium sulfate, and then the solvent was evaporated under a reduced pressure. The resulting residue was mixed with concentrated hydrochloric acid (10 ml) under ice-cooling, further mixed with 1 mol/l hydrochloric acid aqueous solution (5 ml) at roam temperature and then washed with chloroform (50 ml×4), and the insoluble matter was removed by filtration. This hydrochloric acid aqueous solution was adjusted to an alkaline liquid property by adding 10 mol/l sodium hydroxide aqueous solution under ice-cooling and then stirred at room temperature for 1 hour. This suspension was adjusted to a liquid property of pH 7.4 by adding concentrated hydrochloric acid and 1 mol/l hydrochloric acid and then extracted with chloroform (150 ml×3). The resulting organic layer was dried over anhydrous sodium sulfate and the solvent was evaporated under a reduced pressure to obtain the crude title compound as light yellow crystals. This was purified by recrystallizing from ethanol to obtain 120 mg (38%) of the title $^1$H-NMR (400 MHz, 0.1 mol/l NaOD) δ: 1.24–1.43 (3H, m), 1.57–1.59 (1H, m), 2.27–2.29 (1H, m), 3.27–3.29 (1H, m), 3.35–3.37 (1H, m), 3.51–3.56 (3H, m), 3.63 (1H, d, J=8.79 Hz), 4.79 (1H, br. d, J=62.99 Hz), 6.13 (1H, d, J=2.93 Hz), 6.31 (1H, s), 7.34 (1H, s), 8.09 (1H, s).

Melting point: 187–188° C.

Elemental analysis: for $C_{22}H_{21}F_3N_4O_4 \cdot 0.5H_2O$

Calcd.: C, 56.05; H, 4.70; N, 11.88. Found: C, 56.06; H, 4.89; N, 11.62.

REFERENCE EXAMPLE 24

4-(R)-(Thiazol-2-yl)carbonyl-1-[1-(R)-phenylethyl]-2-pyrrolidone

In an atmosphere of nitrogen and at −78° C., n-butyl lithium (20.4 ml, 30.0=mol, 1.47 M hexane solution) was added dropwise to a tetrahydrofuran solution (200 ml) of 2-bromothiazole (4.92 g, 30.0 mmol) spending 10 minutes, and the mixture was stirred at the same temperature for 1 hour. To this was added dropwise a tetrahydrofuran solution (50 ml) of N-methyl-N-methoxy-1-[1-(R)-phenylethyl]-5-oxopyrrolidine-3-carboxamide (6.91 g, 25.0 mmol) spending 10 minutes, and the mixture was stirred at −78° C. for 30 minutes and then under ice-cooling for 1 hour. The reaction solution was mixed with 1 mol/l hydrochloric acid (150 ml) under ice-cooling and extracted with ethyl acetate (100 ml×2), and the resulting organic layer was washed with saturated brine (300 ml) and dried over anhydrous sodium sulfate. The solvent was evaporated under a reduced pressure and the residue was applied to a silica gel column chromatography. By eluting with n-hexane:ethyl acetate (1:1), 2.70 g (36%) of the title compound was obtained as a light yellow oil.

$^1$H-NMR (400 MHz, CDCl$_3$) δ: 1.55 (3H, d, J=7.32 Hz), 2.04–2.92 (2H, m), 3.33–3.38 (1H, m), 3.63–3.68 (1H, m), 4.26–4.35 (1H, m), 5.53 (1H, q, J=7.32 Hz), 7.27–7.38 (5H, m), 7.73 (1H, d, J=2.93 Hz), 8.00 (1H, d, J=2.93 Hz).

REFERENCE EXAMPLE 25

4-(R)-[1-Hydroxy-1-(thiazol-2-yl)methyl]-1-[1-(R)-phenylethyl]-2-pyrrolidone [F1], [F2]

Under ice-cooling, sodium borohydride (409 mg) was added to an ethanol (50 ml) solution of 4-(R)-(thiazol-2-yl)carbonyl-1-[1-(R)-phenylethyl]-2-pyrrolidone (3.24 g, 10.80 mmol), and the mixture was stirred at the same temperature for 30 minutes. The reaction solution was mixed with 10% citric acid (50 ml) under ice-cooling, ethanol was evaporated under a reduced pressure and then the resulting residue was extracted with chloroform (80 ml×2). The organic layer was washed with saturated brine (100 ml) and dried over anhydrous sodium sulfate. The solvent was evaporated under a reduced pressure and the resulting residue was applied to a silica gel column chromatography. By eluting with ethyl acetate, 1.28 g (39%) of the low polarity title compound [F1] and 1.38 g (42%) of the high polarity title compound [2] were obtained in succession, respectively as light yellow crystals and a light yellow oil.

[F1];
$^1$H-NMR (400 MHz, CDCl$_3$) δ: 1.47 (3H, d, J=7.32 Hz), 2.46 (1H, dd, J=9.77, 7.09 Hz), 2.61 (1H, dd, J=7.32, 7.09 Hz), 2.73–2.83 (1H, m), 3.06 (1H, dd, J=10.26, 8.30 Hz), 3.40 (1H, dd, J=10.26, 6.34 Hz), 3.55 (1H, d, J=5.37 Hz), 4.98 (1H, t, J=5.37 Hz), 5.46 (1H, q, J=7.32 Hz), 7.26–7.35 (6H, m), 7.73 (1H, d, J=2.93 Hz).

[F2];
$^1$H-NMR (400 MHz, CDCl$_3$) δ: 1.48 (3H, d, J=6.84 Hz), 2.49 (2H, d, J=8.30 Hz), 2.79–2.88 (1H, m), 2.96–3.01 (1H, m), 3.38 (1H, dd, J=9.77, 5.86 Hz), 4.97 (1H, dd, J=5.37, 4.96 Hz), 5.27 (1H, brs), 5.43 (1H, q, J=6.84 Hz), 7.23–7.32 (6H, m), 7.66 (1H, d, J=3.42 Hz).

REFERENCE EXAMPLE 26

4-(R)-[1-Azido-1-(thiazol-2-yl)methyl]-1-[1-(R)-phenylethyl]-2-pyrrolidone [R$^1$], [F2]

Under ice-cooling, triethylamine (725 μl) and methanesulfonyl chloride (341 μl, 4.40 mmol) were added to a dichloromethane (20 ml) solution of 4-(R)-[1-hydroxy-1-(thiazol-2-yl)methyl]-1-[1-(R)-phenylethyl]-2-pyrrolidone [F1] (1.21 g, 4.00 mmol), and the mixture was stirred at the same the temperature for 1 hour. The reaction solution was mixed with 10% citric acid (30 ml) under ice-cooling and extracted with chloroform (30 ml×2), and the organic layer was washed with saturated brine (100 ml) and then dried over anhydrous sodium sulfate. The solvent was evaporated under a reduced pressure, and the resulting residue was dissolved in N,N-dimethylformamide (30 ml), mixed with sodium azide (780 mg, 12.0 mmol) and then heated at 60° C. for 15 hours. After spontaneous cooling, the reaction solution was mixed with water (70 ml) and extracted with ethyl acetate (80 ml×3), and the organic layer was washed with saturated brine (200 ml) and then dried over anhydrous sodium sulfate. The solvent was evaporated under a reduced pressure, and the resulting residue was applied to a silica gel column chromatography. By eluting with a n-hexane:ethyl acetate system of from (1:2) to (1:3), 1.263 g (96%) of the title compound was obtained as a light yellow oil.

The same reaction was also carried out regarding 4-(R)-[1-hydroxy-1-(thiazol-2-yl)methyl]-1-[1-(R)-phenylethyl]-2-pyrrolidone [F2] (85%).

[F1];

¹H-NMR (400 MHz, CDCl₃) δ: 1.52 (3H, d, J=7.32 Hz), 2.37 (1H, dd, J=7.32, 7.09 Hz), 2.52 (1H, dd, J=8.79, 7.09 Hz), 2.84–2.96 (1H, m), 3.13 (1H, dd, J=10.25, 8.30 Hz), 3.36 (1H, dd, J=10.25, 6.35 Hz), 4.81 (1H, d, J=7.81 Hz), 5.48 (1H, q, J=7.32 Hz), 7.26–7.37 (5H, m), 7.39 (1H, d, J=3.42 Hz), 7.81 (1H, d, J=3.42 Hz).

[F2];

¹H-NMR (400 MHz, CDCl₃) δ: 1.48 (3H, d, J=7.32 Hz), 2.60 (2H, d, J=7.81 Hz), 2.82–2.91 (1H, m), 3.05 (1H, dd, J=10.25, 8.30 Hz), 3.22 (1H, dd, J=10.25, 5.86 Hz), 4.81 (1H, d, J=7.81 Hz), 5.48 (1H, q, J=7.32 Hz), 7.25–7.34 (5H, m), 7.38 (1H, d, J=3.41 Hz), 7.80 (1H, d, J=3.41 Hz).

REFERENCE EXAMPLE 27

4-(R)-[1-Tert-butoxycarbonylamino-1-(thiazol-2-yl)methyl]-1-[-1-(R)-phenylethyl]-2-pyrrolidone [F1], [F2]

An ethanol (50 ml) solution of 4-(R)-[1-azido-1-(thiazol-2-yl)methyl]-1-[1-(R)-phenylethyl]-2-pyrrolidone [F1] (1.18 g, 3.60 mmol) was mixed with 10% palladium-carbon catalyst (53.8% moisture, 1.20 g), and catalytic hydrogenation was carried out at room temperature for 3 hours under ordinary pressure. The reaction solution was filtered, and the solvent was evaporated under a reduced pressure. The residue was dissolved in dichloromethane (30 ml), mixed with di-tert-butyl dicarbonate (1.179 g) and triethylamine (1 ml) and then stirred at room temperature for 14 hours. Chloroform (50 ml) was added to the reaction solution, this was washed with 10% citric acid (80 ml) and water (80 ml), and the resulting organic layer was dried over anhydrous sodium sulfate. The solvent was evaporated under a reduced pressure and the resulting residue was applied to a silica gel column chromatography. By eluting with n-hexane:ethyl acetate (1:3), 1.205 g (83%) of the title A d was stained as colorless amorphous.

The same reaction was also carried out regarding 4-(R)-[1-azido-1-(thiazol-2-yl)methyl]-1-[1-(R)-phenylethyl]-2-pyrrolidone [F2] (75%).

[F1];

¹H-NMR (400 MHz, CDCl₃) δ: 1.44 (9H, s), 1.51 (3H, d, J=6.84 Hz), 2.38 (1H, dd, J=17.09, 7.82 Hz), 2.49 (1H, dd, J=17.09, 9.28 Hz), 2.83–2.95 (1H, m), 3.08 (1H, dd, J=9.77, 8.30 Hz), 3.28 (1H, dd, J=9.77, 6.84 Hz), 5.01–5.09 (1H, m), 5.19–5.26 (1H, m), 5.48 (1H, q, J=6.84 Hz), 7.26–7.35 (6H, m), 7.73 (1H, d, J=2.93 Hz).

[F2];

¹H-NMR (400 MHz, CDCl₃) δ: 1.44 (3H, d, J=7.33 Hz), 1.45 (9H, s), 2.42 (1H, dd, J=17.09, 6.84 Hz), 2.56 (1H, dd, J=17.09, 9.28 Hz), 2.90–3.00 (1H, m), 3.09 (1H, dd, J=9.76, 8.79 Hz), 3.28 (1H, dd, J=9.76, 5.85 Hz), 5.07–5.13 (1H, m), 5.38–5.46 (1H, m), 5.45 (1H, q, J=7.33 Hz), 7.25–7.34 (6H, m), 7.71 (1H, d, J=2.92 Hz).

REFERENCE EXAMPLE 28

3-(R)-[1-Tert-butoxycarbonylamino-1-(thiazol-2-yl)methyl]-1-[1-(R)-phenylethyl]pyrrolidine [F1], [F2]

In an atmosphere of nitrogen, 1Mborane-tetrahydrofuran complex (8.1 ml) was added dropwise to tetrahydrofuran solution (20 ml) of 4-(R)-[1-tert-butoxycarbonylamino-1-(thiazol-2-yl)phenylmethyl]-1-[1-(R)-phenylethyl]-2-pyrrolidone [F1] (1.084 g, 2.70 mmol) under ice-cooling, and then the mixture was stirred at roam temperature for 14 hours. After evaporation of the solvent under a reduced pressure, the resulting residue was mixed with 80% hydrous ethanol (20 ml) and triethylamine (4 ml) and heated under reflux for 4 hours. After spontaneous cooling, the solvent was evaporated under a reduced pressure, chloroform (30 ml) was added to the resulting residue, and then this was washed with water (10 ml) and saturated brine (10 ml) and dried over anhydrous sodium sulfate. The solvent was evaporated under a reduced pressure and the resulting residue was applied to a silica gel column chromatography. By eluting with chloroform:methanol (20:1), 984 mg (94%) of the title compound was obtained as a colorless oil.

The same reaction was also carried out regarding 4-(R)-[1-tert-butoxycarbonylamino-1-(thiazol-2-yl)phenylmethyl]-1-[1-(R)-phenylethyl]-2-pyrrolidone [F2] (85%).

[F1];

¹H-NMR (400 MHz, CDCl₃) δ: 1.40 (3H, d, J=6.35 Hz), 1.51 (9H, s), 1.58–1.71 (2H, m), 1.76–1.89 (1H, m), 2.02–2.30 (2H, m), 2.40–2.50 (1H, m), 2.74–2.85 (1H, m), 3.08–3.23 (2H, m), 4.82–4.90 (1H, m), 7.09 (1H, d, J=3.42 Hz), 7.20–7.32 (5H, m), 7.63 (1H, d, J=3.42 Hz).

[F2];

¹H-NMR (400 MHz, CDCl₃) δ: 1.38 (3H, d, J=6.35 Hz), 1.52 (9H, s), 1.68–1.82 (2H, m), 2.11–2.23 (1H, m), 2.23–2.34 (1H, m), 2.45–2.55 (1H, m), 2.79–2.92 (1H, m), 3.03–3.21 (2H, m), 4.83–4.91 (1H, m), 6.64–6.73 (1H, m), 7.20 (1H, d, J=3.41 Hz), 7.22–7.32 (5H, m), 7.70 (1H, d, J=3.41 Hz).

REFERENCE EXAMPLE 29

3-(R)-[1-Tert-butoxycarbonylamino-1-(thiazol-2-yl)methyl]-1-benzyloxycarbonylpyrrolidine [F1], [F2]

In an atmosphere of nitrogen, benzyl chloroformate (628 μl, 4.40 mmol) was added dropwise to a dichloroethane solution (15 ml) of 3-(R)-[1-tert-butoxycarbonylamino-1-(thiazol-2-yl)methyl]-1-[1-(R)-phenylethyl]-2-pyrrolidone [F1] (852 mg, 2.20 mmol) under ice-cooling and then the mixture was heated under reflux for 16 hours. After spontaneous cooling, the reaction solution was mixed with chloroform (50 ml) and washed with saturated sodium bicarbonate aqueous solution (5 ml), and then the organic layer was dried over anhydrous sodium sulfate. The solvent was evaporated under a reduced pressure, and the resulting residue was applied to a silica gel column chromatography. By eluting with n-hexane:ethyl acetate (1:1), 646 mg (70%) of the title compound was obtained as a colorless oil.

The same reaction was also carried out regarding 3-(R)-[1-tert-butoxycarbonylamino-1-(thiazol-2-yl)methyl]-1-[1-(R)-phenylethyl]pyrrolidine [F2] (83%).

[F1];

¹H-NMR (400 MHz, CDCl₃) δ: 1.43 (9H, s), 1.65–1.84 (1H, m), 1.84–2.00 (1H, m), 2.75–2.91 (1H, m), 3.22–3.39 (2H, m), 3.47–3.68 (2H, m), 4.98–5.12 (1H, m), 5.12 (2H, s), 5.53–5.62 (1H, m), 7.24–7.35 (6H, m), 7.71 (1H, d, J=3.42 Hz).

[F2];

¹H-NMR (400 MHz, CDCl₃) δ: 1.43 (9H, s), 1.74–1.91 (1H, m), 1.95–2.09 (1H, m), 2.76–2.89 (1H, m), 3.14–3.22 (1H, m), 3.29–3.39 (1H, m), 3.49–3.64 (2H, m), 4.97–5.09 (1H, m), 5.11 (2H, s), 5.38–5.47 (1H, m), 7.25–7.35 (6H, m), 7.71 (1H, d, J=3.42 Hz).

REFERENCE EXAMPLE 30

3-(R)-[1-Amino-1-(thiazol-2-yl)methyl]-1-pyrrolidine di-trifluoroacetate [F1], [F2]

3-(R)-[1-Tert-butoxycarbonylamino-1-(thiazol-2-yl)methyl]-1-benzyloxycarbonylpyrrolidine [F1] (480 mg, 1.15 mmol) was mixed with trifluoroacetic acid (10 ml), and the mixture was stirred at room temperature for 1 hour and then heated under reflux for 17 hours. After spontaneous cooling, the solvent was evaporated under a reduced pressure and the resulting residue was mixed with toluene (10 ml). By again evaporating the solvent under a reduced pressure, 473 mg (quantitative) of the crude title compound was obtained as a colorless oil. This was used in the subsequent reaction without purification.

The same reaction was also carried out regarding 3-(R)-[1-tert-butoxycarbonylamino-1-(thiazol-2-yl)methyl]-1-benzyloxycarbonylpyrrolidine [F2].

INVENTIVE EXAMPLE 13

5-Amino-7-[3-(R)-(1-amino-1-(thiazol-2-yl)methyl)-1-pyrrolidinyl]-6,8-difluoro-1-[2-(S)-fluoro-1-(R)-cyclopropyl]-1,4-dihydro-4-oxoquinoline-3-carboxylic acid [F1]

3-(R)-[1-Amino-1-(thiazol-2-yl)methyl]pyrrolidine di-trifluoroacetate [F1] (473 mg, 1.15 mmol) was added to an acetonitrile suspension (10 ml) of 5-amino-6,7,8-trifluoro-1-[2-(S)-fluoro-1-(R)-cyclopropyl]-1,4-dihydro-4-oxoquinoline-3-carboxylic acid (253 mg, 0.8 mmol), and the mixture was heated under reflux for 18 hours in the presence of triethylamine (3 ml). After spontaneous cooling, the solvent of the reaction solution was evaporated under a reduced pressure, and the resulting residue was mixed with concentrated hydrochloric acid (15 ml) and stirred at room temperature for 5 minutes. This hydrochloric acid solution was washed with chloroform (20 ml×3) and then adjusted to an alkaline liquid p by adding 30% sodium hydroxide aqueous solution under ice-cooling. This suspension was adjusted to a liquid property of pH 7.6 by adding concentrated hydrochloric acid and 1 mol/l hydrochloric acid and then extracted with chloroform (100 ml×3). The organic layer was dried over anhydrous sodium sulfate and the solvent was evaporated under a reduced pressure. This was purified by recrystallizing twice from ethanol to obtain 73 mg (19%) of the title Bound as light yellow crystals.

$^1$H-NMR (400 MHz, 0.1 mol/l NaOD) δ: 1.46–1.62 (2H, m), 1.74–1.86 (1H, m), 1.89–2.00 (1H, m), 2.71–2.84 (1H, m), 3.51–3.88 (5H, m), 4.85–4.92 (0.5H, m), 5.01–5.08 (0.5H, m), 5.15 (1H, d, J=9.27 Hz), 7.50 (1H, d, J=3.42 Hz), 7.72 (1H, d, J=3.42 Hz), 8.19 (1H, s).

Melting point: 237.2–241.6° C. (decomp.)

Elemental analysis: for $C_{21}H_{20}F_3N_5O_3S \cdot 1.25H_2O$

Calcd.: C, 50.25; H, 4.52; N, 13.95. Found: C, 50.10; H, 4.52; N, 14.09.

INVENTIVE EXAMPLE 14

5-Amino-7-[3-(R)-(1-amino-1-(thiazol-2-yl)methyl)-1-pyrrolidinyl]-6,8-difluoro-1-[2-(S)-fluoro-1-(R)-cyclopropyl]-1,4-dihydro-4-oxoquinoline-3-carboxylic acid [F2]

3-(R)-[1-Amino-1-(thiazol-2-yl)methyl]pyrrolidine di-trifluoroacetate [F2] (473 mg, 1.15 mmol) was added to an acetonitrile suspension (10 ml) of 5-amino-6,7,8-trifluoro-1-[2-(S)-fluoro-1-(R)-cyclopropyl]-1,4-oxoquinoline-3-carboxylic acid (253 mg, 0.8 mmol), and the mixture was heated under reflux for 18 hours in the presence of triethylamine (3 ml). After spontaneous cooling, the solvent of the reaction solution was evaporated under a reduced pressure, and the resulting residue was mixed with concentrated hydrochloric acid (15 ml) and stirred at room temperature for 5 minutes. This hydrochloric acid solution was washed with chloroform (20 ml×3) and then adjusted to an alkaline liquid property by adding 30% sodium hydroxide aqueous solution under ice-cooling. This suspension was adjusted to a liquid property of pH 7.6 by adding concentrated hydrochloric acid and 1 mol/l hydrochloric acid and then extracted with chloroform (100 ml×3). The organic layer was dried over anhydrous sodium sulfate and the solvent was evaporated under a reduced pressure. This was purified b recrystallizing twice from ethanol to obtain 113 mg (29%) of the title compound as light yellow crystals.

$^1$H-NMR (400 MHz, 0.1 mol/1 NaOD) δ: 1.46–1.62 (2H, m), 1.74–1.86 (1H, m), 1.90–2.00 (1H, m), 2.73–2.85 (1H, m), 3.58–3.88 (5H, m), 4.84–4.92 (0.5H, m), 5.01–5.08 (0.5H, m), 5.15 (1H, d, J=9.27 Hz), 7.50 (1H, d, J=3.42 Hz), 7.72 (1H, d, J=3.42 Hz), 8.19 (1H, s).

Melting point: 236.4–239.8° C. (decomp.)

Elemental analysis: for $C_{21}H_{20}F_3N_5O_3S \cdot 1.0H_2O$

Calcd.: C, 50.70; H, 4.46; N, 14.08. Found: C, 50.90; H, 4.42; N, 14.16.

REFERENCE EXAMPLE 31

1-[1-(R)-Phenylethyl]-4-(R)-[(2-pyridyl)carbonyl]-2-pyrrolidone

In an atmosphere of nitrogen and at −78° C., n-butyl lithium (1.5 mol/l tetrahydrofuran solution; 13.2 ml, 19.9 mol) was added dropwise to a tetrahydrofuran solution (40 ml) of 2-bromopyridine (1.94 ml, 19.9 mmol), and then the mixture was stirred for 10 minutes. At −78° C., to this was further added dropwise a tetrahydrofuran solution (20 ml) of N-methyl-N-methoxy-[1-(R)-phenylethyl]-5-oxopyrrolidine-3-(R)-carboxamide (3.66 g, 13.2 mmol), and the mixture was stirred for 30 minutes. The reaction solution was mixed with 1 mol/l hydrochloric acid (200 ml), warmed up to room temperature and then extracted with diethyl ether (200 ml×2). The resulting organic layer was washed with saturated brine (100 ml) and dried over anhydrous magnesium sulfate. The solvent was evaporated under a reduced pressure and the residue was applied to a silica gel column chromatography (silica gel 100 g). By eluting with a n-hexane:ethyl acetate system of from (3:1) to (1:1), 1.97 g (52%) of the title Sound was obtained as a light yellow oil.

$^1$H-NMR (400 MHz, CDCl$_3$) δ: 1.54 (3H, d, J=7.08 Hz), 2.80–2.83 (2H, m), 3.35 (1H, t, J=9.37 Hz), 3.61 (1H, dd, J=6.35, 9.37 Hz), 4.49–4.54 (1H, m), 5.54 (1H, q, J=7.08 Hz), 7.25–7.38 (5H, m), 7.47–7.50 (1H, m), 7.86 (1H, dt, J=1.71, 7.81 Hz), 8.08 (1H, d, J=7.81 Hz), 8.64–8.65 (1H, m).

REFERENCE EXAMPLE 32

4-(R)-[1-Azido-1-(2-pyridyl)methyl]-1-[1-(R)-phenylethyl]-2-pyrrolidone [F1], [F2]

Under ice-cooling, sodium borohydride (233 mg, 6.15 mmol) was added to a methanol (40 ml) solution of 1-[1-(R)-phenylethyl]-4-(R)-[(2-pyridyl)carbonyl]-2-pyrrolidone (1.81 g, 6.15 mmol), and the mixture was stirred at the same temperature for 30 minutes. The reaction solution was mixed with saturated ammonium chloride aqueous solution (50 ml), stirred at room temperature for 30 minutes and then extracted with chloroform (100 ml×3). The organic layer was washed with saturated brine (50 ml) and dried over anhydrous sodium sulfate. The solvent was evaporated under a reduced pressure to obtain 2.23 g (quantitative) of 4-(R)-[1-hydroxy-1-(2-pyridyl)methyl]-1-[1-(R)-phenylethyl]-2-pyrrolidone as a colorless oil (1:1 mixture of isomers). This was made into a dichloromethane (40 ml) solution, mixed with triethylamine (1.20 ml, 8.61 mmol) and methanesulfonyl chloride (0.571 ml, 7.38 mol) under ice-cooling and then stirred at room temperature for 30 minutes. The reaction solution was washed with saturated ammonium chloride aqueous solution (50 ml) and saturated brine (50 ml), the organic layer was dried over anhydrous sodium sulfate, and then the solvent was evaporated under a reduced pressure. The resulting residue was dissolved in N,N-dimethylformamide (15 ml), mixed with sodium azide (1.00 g, 15.4 mmol) and then heated at 50° C. for 15 hours. After ice-cooling, the reaction solution was mixed with water (50 ml) and extracted with ethyl acetate (50 ml×2), and the resulting organic layer was washed with water (40 ml×3) and saturated brine (40 ml) and dried over anhydrous sodium sulfate. The solvent was evaporated under a reduced pressure and the resulting residue was applied to a silica gel column chromatography (silica gel: 100 g). By eluting with a n-hexane:ethyl acetate system of from (1:1) to (1:3), 754 mg (38%) of the low polarity title compound [F1] and 651 mg (33%) of the high polarity title compound [F2] were obtained in succession each as a colorless oil.

[F1];
$^1$H-NMR (400 MHz, CDCl$_3$) δ: 1.48 (3H, d, J=7.20 Hz), 2.52–2.55 (2H, m), 2.86–2.95 (2H, m), 3.13 (1H, dd, J=5.62, 9.28 Hz), 4.50 (1H, d, J=7.32 Hz), 5.47 (1H, q, J=7.20 Hz), 7.23–7.34 (7H, m), 7.75 (1H, dt, J=1.71, 7.69 Hz), 8.58–8.60 (1H, m).

[F2];
$^1$H-NMR (400 MHz, CDCl$_3$) δ: 1.53 (3H, d, J=7.21 Hz), 2.23 (1H, dd, J=7.81, 17.09 Hz), 2.34 (1H, dd, J=9.03, 17.09 Hz), 2.86–2.96 (1H, m), 3.13 (1H, dd, J=8.06, 10.13 Hz), 3.36 (1H, dd, J=6.35, 10.13 Hz), 4.45 (1H, d, J=8.55 Hz), 5.48 (1H, q, J=7.21 Hz), 7.26–7.36 (7H, m), 7.75 (1H, dt, J=1.71, 7.69 Hz), 8.62 (1H, d, J=3.91 Hz).

REFERENCE EXAMPLE 33

4-(R)-[1-Tert-butoxycarbonylamino-1-(2-pyridyl)methyl]-1-[1-(R)-phenylethyl]-2-pyrrolidone [F1], [F2]

An ethanol (30 ml) solution of 4-(R)-[1-azido-1-(2-pyridyl)methyl]-1-[1-(R)-phenylethyl]-2-pyrrolidone [F1] (619 mg, 1.93 mmol) was mixed with 10% palladium-carbon catalyst (53.8% moisture, 620 mg), and catalytic hydrogenation was carried out at room temperature for 20 minutes under ordinary pressure. The reaction solution was filtered, and the solvent of the filtrate was evaporated under a reduced pressure. A dichloromethane (20 ml) solution of the resulting residue was mixed with di-tert-butyl dicarbonate (463 mg, 2.12 mmol) and triethylamine (350 μl, 2.51 mmol) and stirred at room temperature for 17 hours. The solvent was evaporated under a reduced pressure and the resulting residue was applied to a silica gel column chromatography (silica gel, 40 g). By eluting with a n-hexane: ethyl acetate system of from (1:1) to (1:3), 750 mg (87%) of the title compound [F1] was obtained as colorless amorphous.

The same reaction was also carried out regarding 4-(R)-[1-azido-1-(2-pyridyl)methyl]-1-[1-(R)-phenylethyl]-2-pyrrolidone [F2] (50%).

[F1];
$^1$H-NMR (400 MHz, CDCl$_3$) δ: 1.39 (3H, d, J=7.20 Hz), 1.44 (9H, s), 2.37–2.42 (1H, m), 2.48–2.54 (1H, m), 2.77–2.79 (1H, m), 2.89–2.94 (1H, m), 3.25–3.27 (1H, m), 4.82–4.84 (1H, m), 5.40 (1H, q, J=7.20 Hz), 5.89 (1H, d, J=7.32 Hz), 7.19–7.32 (7H, m), 7.65 (1H, dt, J=1.79, 7.69 Hz), 8.53 (1H, d, J=4.39 Hz).

[F2];
$^1$H-NMR (400 MHz, CDCl$_3$) δ: 1.42 (9H, s), 1.52 (3H, d, J=7.10 Hz), 2.24–2.26 (1H, m), 2.66–2.72 (1H, m), 3.01 (1H, dd, J=8.33, 10.04 Hz), 3.35 (1H, dd, J=6.61, 10.04 Hz), 4.72 (1H, t, J=8.33 Hz), 5.46 (1H, q, J=7.10 Hz), 5.61 (1H, d, J=8.33 Hz), 7.19–7.34 (7H, m), 7.64 (1H, dt, J=1.72, 7.72 Hz), 8.52–8.54 (1H, m).

REFERENCE EXAMPLE 34

3-(R)-[1-Tert-butoxycarbonylamino-1-(2-pyridyl)methyl]-1-[1-(R)-phenylethyl]pyrrolidine [F1], [F2]

In an atmosphere of nitrogen, 1Mborane-tetrahydrofuran complex (6.76 ml, 6.76 mmol) was added dropwise to a tetrahydrofuran solution (15 ml) of 4-(R)-[1-tert-butoxycarbonylamino-1-(2-pyridyl)methyl]-1-[1-(R)-phenylethyl]-2-pyrrolidone [F1] (668 mg, 1.69 mmol) under ice-cooling, and then the mixture was stirred at room temperature for 16 hours. After evaporation of the solvent under a reduced pressure, the resulting residue was mixed with 80% hydrous ethanol (15 ml) and heated under reflux for 4 hours in the presence of triethylamine (1 ml). After spontaneous cooling of the reaction solution, the solvent was evaporated under a reduced pressure, chloroform (50 ml) was added to the resulting residue and then the organic layer was washed with water (40 ml) and saturated brine (40 ml) and dried over anhydrous sodium sulfate. The solvent was evaporated under a reduced pressure and the resulting residue was applied to a silica gel column chromatography (silica gel, 20 g). By eluting with a chloroform:methanol system of from (100:0) to (95:5), 600 mg (93%) of the title compound was obtained as white crystals.

The same reaction was also carried out regarding 4-(R)-[1-tert-butoxycarbonylamino-1-(2-pyridyl)methyl]-1-[1-(R)-phenylethyl]-2-pyrrolidone [F2] (87%).

[F1];
$^1$H-NMR (400 MHz, CDCl$_3$) δ: 1.34 (3H, d, J=6.43 Hz), 1.47 (9H, s), 1.67–1.70 (1H, m), 2.23–2.35 (4H, m), 2.67–2.69 (1H, m), 2.86–2.91 (1H, m), 3.13 (1H, q, J=6.43 Hz), 4.62 (1H, t, J=6.00 Hz), 6.35 (1H, s), 7.10–7.13 (1H, m), 7.13–7.33 (6H, m), 7.57–7.62 (1H, m), 8.50 (1H, d, J=4.16 Hz).

[F2];
$^1$H-NMR (400 MHz, CDCl$_3$) δ: 1.39 (3H, d, J=6.61 Hz), 1.46 (9H, s), 1.71–1.74 (1H, m), 1.91–1.94 (1H, m), 2.22–2.36 (3H, m), 2.66 (1H, s), 2.94–2.95 (1H, m), 3.15–3.17 (1H, m), 4.60–4.63 (1H, m), 6.60–6.69 (1H, m), 7.04–7.08 (1H, m), 7.21–7.32 (6H, m), 7.51 (1H, dt, J=1.71, 7.72 Hz), 8.47 (1H, d, J=4.16 Hz).

REFERENCE EXAMPLE 35

3-(R)-[1-Tert-butoxycarbonylamino-1-(2-pyridyl)methyl]-1-benzyloxycarbonylpyrrolidine [F1], [F2]

In an atmosphere of nitrogen, benzyl chloroformate (728 μl, 5.09 mmol) was added dropwise to a dichloroethane solution (20 ml) of 3-(R)-[1-tert-butoxycarbonylamino-1-(2-pyridyl)methyl]1-[1-(R)phenylethyl]-2-pyrrolidone [F1] (648 mg, 1.70 mmol) under ice-cooling and then the mixture was heated under refulx for 30 hours. After evaporation of the solvent under a reduced pressure, the residue was applied to a silica gel column chromatography (silica gel, 40 g). By eluting with a chloroform:methanol system of from (100:0) to (97:3), 500 mg (72%) of the title compound was obtained as white crystals.

The same reaction was also carried out regarding 3-(R)-[1-tert-butoxycarbonylamino-1-(2-pyridyl)methyl]-1-[1-(R)-phenylethyl]pyrrolidine [F2] (61%).

[F1];
H-NMR (400 MHz, CDCl$_3$) δ: 1.40–1.45 (1H, m), 1.42 (9H, s), 1.86–1.94 (1H, m), 2.59–2.62 (1H, m), 3.04–3.11 (1H, m), 3.22–3.33 (2H, m), 3.54–3.58 (1H, m), 4.66–4.72 (1H, m), 5.09 (2H, s), 5.71–5.73 (1H, m), 7.16–7.34 (7H, m), 7.63 (1H, dt, J=1.71, 7.59 Hz), 8.53 (1H, d, J=3.92 Hz).

[F2];
$^1$H-NMR (400 MHz, CDCl$_3$) δ: 1.42 (9H, s), 1.58–1.67 (2H, m), 2.61–2.67 (1H, m), 3.27–3.55 (4H, m), 4.70–4.80 (1H, m), 5.10 (1H, s), 5.12 (1H, s), 5.71–5.78 (1H, m), 7.17–7.36 (7H, m), 7.60–7.63 (1H, m), 8.55 (1H, s).

REFERENCE EXAMPLE 36

3-(R)-[1-Tert-butoxycarbonylamino-1-(2-pyridyl)methyl]pyrrolidine [F1], [F2]

An ethanol (20 ml) solution of 3-(R)-[1-tert-butoxycarbonylamino-1-(2-pyridyl)methyl]-1-benzyloxycarbonylpyrrolidine [F1] (500 mg, 1.22 mmol) was mixed with 10% palladium-carbon catalyst (53.8% moisture, 500 mg), and catalytic hydrogenation was carried out at room temperature for 18 hours under ordinary pressure. The reaction solution was filtered and the solvent of the filtrate was evaporated under a reduced pressure to obtain the crude title compound as colorless crystals. This was used in the subsequent reaction without purification.

The same reaction was also carried out regarding 3-(R)-[1-tert-butoxycarbonylamino-1-(2-pyridyl)methyl]-1-benzyloxycarbonylpyrrolidine [F2].

INVENTIVE EXAMPLE 15

5-Amino-7-{3-(R)-[1-amino-1-(2-pyridyl)methyl]-pyrrolidinyl}-6,8-difluoro-1-[(1R,2S)-2-fluorocyclopropyl]-1,4-dihydro-4-oxoquinoline-3-carboxylic acid 3-(R)-[1-Tert-butoxycarbonylamino-1-(2-pyridyl)methyl]pyrrolidine [F1] (339 mg, 1.22 mmol) was added to an acetonitrile suspension (10 ml) of 5-amino-6,7,8-trifluoro-1-[2-(S)-fluoro-1-(R)-cyclopropyl]-1,4-dihydro-4-oxo-quinoline-3-carboxylic acid (316 mg, 1.00 mmol), and the mixture was heated under reflux for 14 hours in the presence of triethylmine (0.5 ml). After cooling, the solvent of the reaction solution was evaporated under a reduced pressure. The resulting residue was dissolved in chloroform (150 ml), this was washed with 10% citric acid (80 ml) and saturated brine (80 ml) and dried over anhydrous sodium sulfate, and then the solvent was evaporated under a reduced pressure. The resulting residue was mixed with concentrated hydrochloric acid (10 ml) under ice-cooling, further mixed with 1 mol/l hydrochloric acid aqueous solution (5 ml) at roan temperature and then washed with chloroform (50 ml×4), and the insoluble matter was removed by filtration. This hydrochloric acid aqueous solution was adjusted to an alkaline liquid property adding 10 mol/l sodium hydroxide aqueous solution. This suspension was adjusted to a liquid property of pH 7.4 by adding concentrated hydrochloric acid and 1 mol/l hydrochloric acid and then extracted with chloroform (150 ml×4). The resulting organic layer was dried over anhydrous sodium sulfate and the solvent was evaporated under a reduced pressure to obtain the crude title compound as light yellow crystals. This was purified by recrystallizing from ethanol to obtain 316 mg (67%) of the title compound.

$^1$H-NMR (400 MHz, 0.1 mol/l NaOD) δ: 1.45–1.47 (2H, m), 1.75–1.77 (1H, m), 2.25–2.27 (1H, m), 2.48–2.50 (1H, m), 2.97–3.00 (1H, m), 3.30–3.83 (5H, m), 4.76 (1H, br. d, J=62.50 Hz), 7.35–7.44 (2H, m), 8.52 (1H, t, J=7.81 Hz), 8.12 (1H, s), 8.46 (1H, d, J=4.39 Hz).

Melting point: 194–196° C.

Elemental analysis: for 0.5H$_2$O.0.5EtOH.C$_{23}$H$_{22}$F$_3$N$_5$O$_3$
Calcd.: C, 57.03; H, 5.18; N, 13.85. Found: C, 57.03; H, 5.11; N, 13.85.

INVENTIVE EXAMPLE 16

5-Amino-7-{3-(R)-[1-amino-1-(2-pyridyl)methyl]-1-pyrrolidinyl}-6,8-difluoro-1-[(1R,2S)-2-fluorocyclopropyl]-1,4-dihydro-4-oxoquinoline-3-carboxylic acid 3-(R)-[1-Tert-butoxycarbonylamino-1-(2-pyridyl)methyl]pyrrolidine [F2] (0.535 mmol) was added to an acetonitrile suspension (5 ml) of 5-amino-6,7,8-trifluoro-1-[2-(S)-fluoro-1-(R)-cyclopropyl]-1,4-dihydro-4-oxoquinoline-3-carboxylic acid (169 mg, 0.534 mmol), and the mixture was heated under reflux for 19 hours in the presence of triethylamine (0.5 ml). After cooling, the solvent of the reaction solution was evaporated under a reduced pressure. The resulting residue was dissolved in chloroform (50 ml), this was washed with 10% citric acid (40 ml) and saturated brine (40 ml) and dried over anhydrous sodium sulfate, and then the solvent was evaporated under a reduced pressure. The resulting residue was mixed with concentrated hydrochloric acid (5 ml) under ice-cooling, further mixed with 1 mol/l hydrochloric acid aqueous solution (5 ml) at roam temperature and then washed with chloroform (50 ml×5). This hydrochloric acid aqueous solution was adjusted to an alkaline liquid property by adding 10 mol/l sodium hydroxide aqueous solution and then stirred at room temperature for 1 hour. This suspension was adjusted to a liquid property of pH 7.4 by adding concentrated hydrochloric acid and 1 mol/l hydrochloric acid and then extracted with chloroform (150 ml×3). The resulting organic layer was dried over anhydrous sodium sulfate and the solvent was evaporated under a reduced pressure to obtain the crude title compound as light yellow crystals. This was purified by recrystallizing from ethanol to obtain 136 mg (54%) of the title compound.

$^1$H-NMR (400 MHz, 0.1 mol/l NaOD) δ: 1.52–1.54 (3H, m), 2.49–2.51 (2H, m), 3.41–3.86 (6H, m), 4.69–4.77 (1H, m), 7.35–7.42 (2H, m), 7.82–7.86 (1H, m), 8.17 (1H, s), 8.46 (1H, s).
Melting point: 178–180° C.
Elemental analysis: for $0.75H_2O.C_{23}H_{22}F_3N_5O_3$
Calcd.: C, 56.73; H, 4.86; N, 14.38. Found: C, 56.50; H, 4.81; N, 14.29.

INVENTIVE EXAMPLE 17

5-Amino-7-{3-(R)-[1-amino-1-(2-pyridyl)methyl]-1-pyrrolidinyl}-6-fluoro-1-[(1R,2S)-2-fluorocyclopropyl]-1,4-dihydro-8-methyl-4-oxoquinoline-3-carboxylic acid (F2: D91-5400)

3-(R)-[1-Tert-butoxycarbonylamino-1-(2-pyridyl)methyl]pyrrolidine [F2] (1.00 mmol) was added to a dimethyl sulfoxide suspension (3 ml) of 5-amino-6,7-trifluoro-1-[2-(S)-fluoro-1-(R)-cyclopropyl]-1,4-dihydro-8-methyl-4-oxoquinoline-3-carboxylic acid (284 mg, 0.910 mmol), and the mixture was stirred at 80° C. for 93 hours in the presence of N-methylpiperidine (0.146 ml, 1.09 mmol). After cooling, the solvent of the reaction solution was evaporated under a reduced pressure. The resulting residue was dissolved in chloroform (50 ml), this was washed with 10% citric acid (50 ml) and saturated brine (40 ml) and dried over anhydrous sodium sulfate, and then the solvent was evaporated under a reduced pressure. The resulting residue was applied to a silica gel column chromatography (silica gel, 40 g) and eluted with a chloroform:methanol system of from (100:0) to (98:2) and then the solvent in the eluate was evaporated under a reduced pressure. The resulting residue was mixed with concentrated hydrochloric acid (5 ml) under ice-cooling, further mixed with 1 mol/l hydrochloric acid aqueous solution (5 ml) at room temperature and then washed with chloroform (50 ml×4). This hydrochloric acid aqueous solution was adjusted to an alkaline liquid property by adding 10 mol/l sodium hydroxide aqueous solution. This suspension was adjusted to a liquid property of pH 7.4 by adding concentrated hydrochloric acid and 1 mol/l hydrochloric acid and then extracted with chloroform (150 ml×3). The resulting organic layer was dried over anhydrous sodium sulfate, the solvent was evaporated under a reduced pressure and then the resulting residue was partially purified by PTC (Whatman, PLK5F, 150 Å) to Obtain the crude title compound as light yellow crystals. This was purified by recrystallizing from isopropyl alcohol to obtain 70.0 mg (16%) of the title compound.
$^1$H-NMR (400 MHz, 0.1 mol/l NaOD) δ: 1.02–1.11 (1H, m), 1.46–1.59 (2H, m), 2.20–2.26 (1H, m), 2.23 (3H, s), 2.58–2.61 (1H, m), 3.13–3.17 (1H, m), 3.45–3.64 (3H, m), 3.87–3.92 (2H, m), 4.78–4.83 (1H, m), 7.34–7.45 (2H, m), 7.85–7.87 (1H, m), 8.27 (1H, s), 8.45 (1H, s).
Melting point: 127–129° C.
Elemental analysis: for $1.25H_2O.C_{24}H_{25}F_2N_5O_3$
Calcd.: C, 58.59; H, 5.63; N, 14 Found: C, 58.69; H, 5.52; N, 14.25.

REFERENCE EXAMPLE 37

1-[1-(R)-Phenylethyl]-4-(R)-[(3-pyridyl)carbonyl]-2-pyrrolidone

In an atmosphere of nitrogen and at −78° C., n-butyl lithium (1.5 mol/l tetrahydrofuran solution; 18.1 ml, 27.2 mmol) was added dropwise to a tetrahydrofuran solution (200 ml) of 3-bromopyridine (2.61 ml, 27.2 mmol), and then the mixture was stirred for 10 minutes. At −78° C., to this was further added dropwise a tetrahydrofuran solution (15 ml) of N-methyl-N-methoxyl-[1-(R)-phenylethyl]-5-oxopyrrolidine-3-R)-carboxamide (5.00 g, 18.1 mmol), and the mixture was stirred for 30 minutes. The reaction solution was mixed with 1 mol/l hydrochloric acid (100 ml), warmed up to room temperature and extracted with chloroform (200 ml×2), and then the resulting organic layer was washed with saturated brine (100 ml) and dried over anhydrous sodium sulfate. The solvent was evaporated under a reduced pressure and the resulting residue was applied to a silica gel column chromatography (silica gel 100 g). By eluting with a n-hexane:ethyl acetate system of from (1:4) to (0:100), 2.16 g (41%) of the title compound was obtained as a light yellow oil.
$^1$H-NMR (400 MHz, CDCl$_3$) δ: 1.56 (3H, d, J=7.32 Hz), 2.82 (2H, d, J=7.32 Hz), 3.20–3.27 (1H, m), 3.70–3.74 (1H, m), 3.97–4.01 (1H, m), 5.51–5.55 (1H, m), 7.26–7.47 (6H, m), 8.21 (1H, d, J=8.06 Hz), 8.81 (1H, d, J=4.39 Hz), 9.09 (1H, s).

REFERENCE EXAMPLE 38

4-(R)-[1-Azido-1-(3-pyridyl)methyl]-1-[1-(R)-phenylethyl]-2-pyrrolidone [F1], [F2]

Under ice-cooling, sodium borohydride (580 mg, 15.3 mmol) was added to a methanol (90 ml) solution of 1-[1-(R)-phenylethyl]-4-(R)-[(3-pyridyl)carbonyl]-2-pyrrolidone (4.51 g, 15.3 mmol), and the mixture was stirred at the same temperature for 30 minutes. The reaction solution was mixed with saturated ammonium chloride aqueous solution (50 ml), stirred for 30 minutes and then extracted with ethylacetate (100 ml×3). The organic layer was washed with saturated brine (50 ml) and then dried over anhydrous sodium sulfate The solvent was evaporated under a reduced pressure to obtain 3.88 g (86%) of a synthesis intermediate 4-(R)-[1-hydroxy-1-(3-pyridyl)methyl]-1-[1-(R)-phenylethyl]-2-pyrrolidone as a colorless oil. This was made into a dichloromethane (100 ml) solution, mixed with triethylamine (3.10 ml, 22.3 mmol) and methanesulfonyl chloride (1.52 ml, 19.7 mmol) under ice-cooling and then stirred at room temperature for 30 minutes. The reaction solution was washed with saturated ammonium chloride aqueous solution (100 ml) and saturated brine (100 ml), the organic layer was dried over anhydrous sodium sulfate, and then the solvent was evaporated under a reduced pressure. The resulting residue was dissolved in N,N-dimethylformamide (30 ml), mixed with sodium azide (2.49 g, 32.8 mmol) and then heated at 40° C. for 14 hours. After ice-cooling, the reaction solution was mixed with water (100 ml) and extracted with ethylacetate (100 ml×2), and the resulting organic layer was washed with water (80 ml×3) and saturated brine (80 ml) and dried over anhydrous sodium sulfate. The solvent was evaporated under a reduced pressure and the resulting residue was applied to a silica gel column chromatography (silica gel: 100 g). By eluting with n-hexane:ethyl acetate (3:5), ethyl acetate and chloroform:methanol (90:10), 976 mg (23%) of the low polarity title compound [F1] and 1.73 g (41%) of the high polarity title compound [F2] were obtained in succession each as a colorless oil.

[F1];
$^1$H-NMR (400 MHz, CDCl$_3$) δ: 1.48 (3H, d, J=7.08 Hz), 2.54–2.64 (3H, m), 2.82–2.86 (1H, m), 2.96 (1H, dd, J=5.86, 10.01 Hz), 4.44 (1H, d, J=7.33 Hz), 5.48 (1H, q, J=7.08 Hz), 7.21–7.62 (6H, m), 7.64 (1H, d, J=6.10 Hz), 8.54 (1H, d, J=1.95 Hz), 8.63 (1H, dd, J=1.47, 4.86 Hz).

[F2];
¹H-NMR (400 MHz, CDCl₃) δ: 1.54 (3H, d, J=7.08 Hz), 2.11–2.18 (1H, m), 2.26–2.33 (1H, m), 2.56–2.68 (1H, m), 3.13–3.20 (2H, m), 4.43 (1H, d, J=9.28 Hz), 5.46–5.53 (1H, m), 7.24–7.38 (6H, m), 7.63 (1H, dt, J=1.95, 7.81 Hz), 8.57 (1H, d, J=2.20 Hz), 8.64 (1H, dd, J=1.71, 4.88 Hz).

REFERENCE EXAMPLE 39

4-(R)-[1-Tert-butoxycarbonylamino-1-(3-pyridyl) methyl]-1-[1-(R)-phenylethyl]-2-pyrrolidone [F1], [F2]

An ethanol (30 ml) solution of 4-(R)-[1-azido-1-(3-pyridyl)methyl]-1-[1-(R)-phenylethyl]-2-pyrrolidone [F1] (976 mg, 3.04 mmol) was mixed with 10% palladium-carbon catalyst (53.8% moisture, 1.00 g), and catalytic hydrogenation was carried out at room temperature for 1 hour under ordinary pressure. The reaction solution was filtered, and the solvent of the filtrate was evaporated under a reduced pressure. A dichloromethane (20 ml) solution of the resulting residue was mixed with tert-butyl dicarbonate (729 mg, 3.34 mmol) and triethylamine (551 μl, 3.95 mmol) and stirred at room temperature for 16 hours. The solvent was evaporated under a reduced pressure and the resulting residue was plied to a silica gel column chromatography (silica gel, 20 g). By eluting with a chloroform:methanol system of from (100:0) to (95:5), 654 mg (54%) of the title compound [F1] was obtained as colorless amorphous.

The same reaction was also carried out regarding 4-(R)-[1-azido-1-(3-pyridyl)methyl]-1-[1-(R)-phenylethyl]-2-pyrrolidone [F2] (36%).

[F1]
¹H-NMR (400 MHz, CDCl₃) δ: 1.41 (9H, s), 1.47 (3H, d, J=7.32 Hz), 2.44–2.50 (1H, m), 2.57–2.64 (1H, m), 2.63–2.67 (1H, m), 2.83–2.87 (1H, m), 2.97–3.01 (1H, m), 4.68–4.72 (1H, m), 4.91–4.95 (1H, m), 5.48 (1H, q, J=7.32 Hz), 7.21–7.32 (6H, m), 7.55 (1H, d, J=7.81 Hz), 8.52–8.55 (2H, m).

[F2];
¹H-NMR (400 MHz, CDCl₃) δ: 1.39 (9H, s), 1.53 (3H, d, J=7.17 Hz), 2.13 (1H, dd, J=8.08, 16.9 Hz), 2.27 (1H, dd, J=8.57, 16.4 Hz), 2.61–2.65 (1H, m), 3.11–3.16 (1H, m), 3.25–3.30 (1H, m), 4.62–4.66 (1H, m), 4.77–4.81 (1H, m), 5.48 (1H, q, J=7.17 Hz), 7.26–7.36 (6H, m), 7.54 (1H, d, J=7.35 Hz), 8.54 (2H, dd, J=1.71, 4.90 Hz).

REFERENCE EXAMPLE 40

3-(R)-[1-Tert-butoxycarbonylamino-1-(3-pyridyl) methyl]-1-[1-(R)-phenylethyl]pyrrolidine [F1], [F2]

In an atmosphere of nitrogen, 1Mborane-tetrahydrofuran complex (7.74 ml, 7.74 mmol) was added dropwise to a tetrahydrofuran solution (12 ml) of 4-(R)-[1-tert-butoxycarbonylamino-1-(3-pyridyl)methyl]-1-[1-(R)-phenylethyl]-2-pyrrolidone [F1] (612 mg, 1.55 mmol) under ice-cooling, and then the mixture was stirred at room temperature for 18 hours. After evaporation of the solvent under a reduced pressure, the resulting residue was dissolved in 80% hydrous ethanol (20 ml) and heated under reflux for 4 hours in the presence of triethylamine (1 ml). After spontaneous cooling of the reaction solution, the solvent was evaporated under a reduced pressure, chloroform (40 ml) was added to the resulting residue and then the organic layer was washed with water (30 ml) and saturated brine (30 ml) and dried over anhydrous sodium sulfate. The solvent was evaporated under a reduced pressure and the resulting residue was applied to a silica gel column chromatography (silica gel, 10 g). By eluting with a chloroform:methanol system of from (100:0) to (97:3), 461 mg (78%) of the title compound was obtained as white crystals.

The same reaction was also carried out regarding 4-(R)-[1-tert-butoxycarbonylamino-1-(3-pyridyl)methyl]-1-[1-(R)-phenylethyl]-2-pyrrolidone [F2] (71%).

[F1];
¹H-NMR (400 MHz, CDCl₃) δ: 1.37 (3H, d, J=6.59 Hz), 1.49 (9H, s), 2.17–2.25 (2H, m), 2.42–2.45 (2H, m), 2.95–3.16 (2H, m), 4.53–4.57 (1H, m), 6.44–6.48 (1H, m), 7.21–7.35 (6H, m), 7.52–7.54 (1H, m), 8.46 (1H, dd, J=1.47, 4.88 Hz), 8.50 (1H, s).

[F2];
¹H-NMR (400 MHz, CDCl₃) δ: 1.41 (3H, d, J=6.59 Hz), 1.47 (9H, s), 2.00–2.04 (2H, m), 2.20–2.26 (1H, m), 2.36–2.41 (2H, m), 3.14–3.21 (2H, m), 4.53–4.56 (1H, m), 6.99–7.01 (1H, m), 7.10–7.13 (1H, m), 7.26–7.35 (6H, m), 8.35–8.39 (2H, m).

REFERENCE EXAMPLE 41

3-(R)-[1-Tert-butoxycarbonylamino-1-(3-pyridyl) methyl]pyrrolidine [F1], [F2]

An ethanol (10 ml) solution of 3-(R)-[1-tert-butoxycarbonylamino-1-(3-pyridyl)methyl]-1-[1-(R)-phenylethyl] pyrrolidine [F1] (105 mg, 0.275 mmol) was mixed with 10% palladium-carbon catalyst (53.8% moisture, 105 mg), and catalytic hydrogenation was carried out at 40° C. for 23 hours under ordinary pressure. The reaction solution was filtered and the solvent of the filtrate was evaporated under a reduced pressure to obtain the crude title compound as colorless crystals. This was directly used in the subsequent reaction.

The same reaction was also carried out regarding 3-(R)-[1-tert-butoxycarbonylamino-1-(3-pyridyl)methyl]-1-[1-(R)-phenylethyl]pyrrolidine [F2].

INVENTIVE EXAMPLE 18

5-Amino-7-{3-(R)-[1-amino-1-(3-pyridyl)methyl]-1-pyrrolidinyl}-6,8-difluoro-1-[1R,2S)-2-fluorocyclopropyl]-1,4-dihydro-4-oxoquinoline-3-carboxylic acid 3-(R)-[1-Tert-butoxycarbonylamino-1-(3-pyridyl)methyl]pyrrolidine [F1] (70 mg, 0.252 mmol) was added to an acetonitrile suspension (3 ml) of 5-amino-6,7,8-trifluoro-1-[2-(S)-fluoro-1-(R)-cyclopropyl]-1,4-dihydro-4-oxoquinoline-3-carboxylic acid (87.0 mg, 0.275 mmol), and the mixture was heated under reflux for 19 hours in the presence of triethylamine (0.3 ml). After cooling, the solvent of the reaction solution was evaporated under a reduced pressure.

The resulting residue was dissolved in chloroform (50 ml), this was washed with 10% citric acid (40 ml) and saturated brine (40 ml) and dried over anhydrous sodium sulfate, and then the solvent was evaporated under a reduced pressure. The resulting residue was mixed with concentrated hydrochloric acid (2 ml) under ice-cooling, further mixed with 1 mol/l hydrochloric acid aqueous solution (2 ml) at room temperature and then washed with chloroform (30 ml×4), and the insoluble matter was removed by filtration. This hydrochloric acid solution was adjusted to an alkaline liquid property by adding 10 mol/l sodium hydroxide aqueous solution. This suspension was adjusted to a liquid property of pH 7.4 by adding concentrated hydrochloric acid and 1 mol/l hydrochloric acid and then extracted with chloroform (150 ml×3). The resulting organic layer was dried over anhydrous sodium sulfate and the solvent was evaporated under a reduced pressure to obtain the crude title compound as light yellow crystals. This was purified by recrystallizing from ethanol-aqueous ammonia to obtain 65.1 mg (54%) of the title compound $^1$H-NMR (400 MHz, 0.1 mol/l NaOD) δ: 1.32–1.38 (2H, m), 1.54–1.58 (1H, m), 2.19–2.21 (1H, m), 2.30–2.35 (1H, m), 2.79–2.81 (1H, m), 3.08–3.10 (1H, m), 3.34–3.69 (41H, m), 4.77–4.81 (1H, dn), 7.43 (1H, d, J=7.57 Hz), 7.79 (1H, d, J=7.57 Hz), 8.12 (1H, s), 8.43–8.45 (2H, m).

Melting point: 263–265° C. (decomp.)

Elemental analysis: for $0.25H_2O \cdot C_{23}H_{22}F_3N_5O_3$

Calcd.: C, 57.80; H, 4.74; N, 14.65. Found: C, 57.62; H, 4.81; N, 14.30.

INVENTIVE EXAMPLE 19

5-Amino-7-{3-(R)-[1-amino-1-(3-pyridyl)methyl]-1-pyrrolidinyl}-6,8-difluoro-1-[(1R,2S)-2-fluorocyclopropyl]-1,4-dihydro-4-oxoquinoline-3-carboxylic acid 3-(R)-[1-Tert-butoxycarbonylamino-1-(3-pyridyl)methyl]pyrrolidine [F2] (0.461 mmol) was added to an acetonitrile suspension (5 ml) of 5-amino-6,7,8-trifluoro-1-[2-(S)-fluoro-1-(R)-cyclopropyl]-1,4-dihydro-4-oxoquinoline-3-carboxylic acid (156 mg, 0.493 mmol), and the mixture was heated under reflux for 19 hours in the presence of triethylamine (0.5 ml). After cooling, the solvent of the reaction solution was evaporated under a reduced pressure. The resulting residue was dissolved in chloroform (50 ml), this was washed with 10% citric acid (40 ml) and saturated brine (40 ml) and dried over anhydrous sodium sulfate, and then the solvent was evaporated under a reduced pressure. The resulting residue was mixed with concentrated hydrochloric acid (5 ml) under ice-cooling, further mixed with 1 mol/l hydrochloric acid aqueous solution (5 ml) at room temperature and then washed with chloroform (50 ml×5). This hydrochloric acid aqueous solution was adjusted to an alkaline liquid property by adding 10 mol/l sodium hydroxide aqueous solution, further adjusted to a liquid property of pH 7.4 by adding concentrated hydrochloric acid and 1 mol/l hydrochloric acid and then extracted with chloroform (150 ml×3). The resulting organic layer was dried over anhydrous sodium sulfate and the solvent was evaporated under a reduced pressure to obtain the crude title compound as light yellow crystals. This was purified by recrystallizing from ethanol to obtain 71.5 mg (32%) of the title compound.

$^1$H-NMR (400 MHz, 0.1 mol/l NaOD) δ: 1.36–1.45 (2H, m), 1.53–1.59 (2H, m), 2.42–2.47 (1H, m), 3.40–3.81 (6H, m), 4.95–5.01 (1H, dm), 7.46 (1H, d, J=6.35 Hz), 7.83 (1H, d, J=7.57 Hz), 8.18 (1H, s), 8.44–8.48 (2H, m).

Melting point: 123–126° C.

Elemental analysis: for $1H_2O \cdot C_{23}H_{22}F_3N_5O_3$

Calcd.: C, 56.21; H, 4.92; N, 14.25. Found: C, 56.43; H, 4.87; N, 14.05.

INVENTIVE EXAMPLE 20

5-Amino-7-{3-(R)-[1-amino-1-(3-pyridyl)methyl]-1-pyrrolidinyl}-6-fluoro-1-[(1R,2S)-2-fluorocyclopropyl]-1,4-dihydro-8-methyl-4-oxoquinoline-3-carboxylic acid 3-(R)-[1-Tert-butoxycarbonylamino-1-(3-pyridyl)methyl]pyrrolidine [F2] (1.60 mmol) was added to a dimethyl sulfoxide suspension (3 ml) of 5-amino-6,7-trifluoro-1-[2-(S)-fluoro-1-(R)-cyclopropyl]-1,4-dihydro-8-methyl-4-oxoquinoline-3-carboxylic acid (427 mg, 1.33 mmol), and the mixture was stirred at 80° C. for 161 hours in the presence of N-methylpiperidine (0.356 ml, 2.93 mmol). After cooling, the solvent of the reaction solution was evaporated under a reduced pressure. The resulting residue was dissolved in chloroform (100 ml), this was washed with 10% citric acid (50 ml) and saturated brine (40 ml) and dried over anhydrous sodium sulfate, and then the solvent was evaporated under a reduced pressure. The resulting residue was mixed with concentrated hydrochloric acid (5 ml) under ice-cooling, further mixed with 1 mol/l hydrochloric acid aqueous solution (5 ml) at room temperature and then washed with chloroform (30 ml×4). This hydrochloric acid aqueous solution was adjusted to an alkaline liquid property by adding 10 mol/l sodium hydroxide aqueous solution. This suspension was adjusted to a liquid property of pH 7.4 by adding concentrated hydrochloric acid and 1 mol/l hydrochloric acid and then extracted with chloroform (150 ml×3). The resulting organic layer was dried over anhydrous sodium sulfate, the solvent was evaporated under a reduced pressure and then the resulting residue was partially purified by PTLC (Whatman, PLK5F, 150 Å) to obtain 100 mg of the crude title compound as light yellow crystals. This was purified by recrystallizing from isopropyl alcohol to obtain 62.2 mg (10%) of the title compound.

$^1$H-NMR (400 MHz, 0.1 mol/l NaOD) δ: 1.04–1.06 (1H, m), 1.11–1.13 (1H, m), 1.45–1.49 (2H, m), 1.58–1.60 (1H, m), 2.23 (3H, s), 2.56–2.59 (1H, m), 3.14–3.16 (1H, m), 3.49–3.51 (1H, m), 3.59–3.62 (2H, m), 3.85–3.89 (2H, m), 4.88–5.04 (1H, dm), 7.46 (1H, s), 7.86 (1H, d, J=7.34 Hz), 8.27 (1H, s), 8.45 (1H, d, J=4.89 Hz), 8.51 (1H, s).

Melting point: 213–215° C.

Elemental analysis: for $0.5H_2O \cdot C_{24}H_{25}F_2N_5O_3$

Calcd.: C, 60.24; H, 5.48; N, 14.64. Found: C, 60.46; H, 5.46; N, 14.55.

Antibacterial activities of the compounds of the invention were measured in accordance with the standard method specified by the Japan Society of Chemotherapy, with the results shown in the following table as MIC values (μg/ml). In this connection, MIC values of levofloxacin (LVFX), ciprofloxacin (CPEX) and 5-amino-7-[3-(R)-[1-(S)-aminoethyl]pyrrolidin-1-yl]-6-fluoro-1-[2-(S)-fluoro-1-(R)-cyclopropyl]-8-methyl-1,4-dihydro-4-oxoquinoline-3-carboxylic acid (control drug 1) described in WO 9623782 are also shown for the sake of comparison with the MIC values of the compounds of the invention.

| Table Antibacterial activity | | | | | | | | | |
|---|---|---|---|---|---|---|---|---|---|
| | (Example No.) | | | | | | | | |
| Bacterium/compound | 1 | 2 | 3 | 4 | 5 | 6 | 8 | 10 | 11 |
| E. coli NIHJ | ≦0.003 | ≦0.003 | ≦0.003 | ≦0.003 | ≦0.003 | 0.006 | ≦0.003 | ≦0.003 | ≦0.003 |
| S. flexneri 2A 5503 | 0.006 | ≦0.003 | ≦0.003 | ≦0.003 | ≦0.003 | 0.013 | 0.006 | ≦0.003 | ≦0.003 |
| Pr. Vulgaris O8601 | 0.1 | 0.025 | 0.025 | 0.013 | 0.013 | 0.1 | 0.2 | 0.1 | 0.05 |
| K. pneumoniae TYPE 1 | 0.05 | 0.013 | 0.025 | 0.025 | 0.013 | 0.05 | 0.05 | 0.013 | 0.025 |
| Ser. marcescens 10100 | 0.1 | 0.05 | 0.05 | 0.025 | 0.025 | 0.1 | 0.2 | 0.1 | 0.05 |
| Ps. aeruginosa 32104 | 0.2 | 0.1 | 0.1 | 0.1 | 0.1 | 0.2 | 0.2 | 0.2 | 0.2 |
| Ps. aeruginosa 32121 | 0.1 | 0.025 | 0.05 | 0.05 | 0.025 | 0.1 | 0.1 | 0.1 | 0.05 |
| X. maltophilia IID 1275 | 0.1 | 0.025 | 0.025 | 0.05 | 0.025 | 0.1 | 0.2 | 0.05 | 0.05 |
| S. aureus FDA 209P | ≦0.003 | ≦0.003 | ≦0.003 | ≦0.003 | ≦0.003 | ≦0.003 | ≦0.003 | ≦0.003 | ≦0.003 |
| S. epidermidis 56500 | ≦0.003 | ≦0.003 | ≦0.003 | ≦0.003 | ≦0.003 | 0.006 | ≦0.003 | ≦0.003 | ≦0.003 |
| Str. pyrogenes G-36 | 0.013 | ≦0.003 | ≦0.003 | ≦0.003 | ≦0.003 | ≦0.003 | ≦0.003 | ≦0.003 | 0.013 |
| E. faecalis ATCC 19433 | 0.05 | 0.006 | 0.013 | 0.006 | 0.006 | 0.025 | 0.025 | 0.025 | 0.025 |
| S. aureus 870307 | 0.025 | ≦0.003 | ≦0.003 | ≦0.003 | ≦0.003 | 0.013 | 0.013 | 0.006 | 0.025 |
| Str. pneumoniae J24 | 0.006 | ≦0.003 | ≦0.003 | ≦0.003 | ≦0.003 | ≦0.003 | ≦0.003 | ≦0.003 | 0.006 |

| | (Example No.) | | | | | | | |
|---|---|---|---|---|---|---|---|---|
| Bacterium/compound | 12 | 16 | 17 | 19 | 20 | LVFX | CPFX | Control drug 1 |
| E. coli NIHJ | ≦0.003 | ≦0.003 | ≦0.003 | ≦0.003 | 0.006 | 0.013 | ≦0.003 | 0.006 |
| S. flexneri 2A 5503 | ≦0.003 | ≦0.003 | 0.006 | ≦0.003 | 0.006 | 0.025 | 0.006 | 0.006 |
| Pr. Vulgaris O8601 | 0.013 | 0.025 | 0.05 | 0.025 | 0.025 | 0.13 | ≦0.003 | 0.013 |
| K. pneumoniae TYPE 1 | 0.025 | 0.025 | 0.05 | 0.025 | 0.05 | 0.1 | 0.025 | 0.05 |
| Ser. marcescens 10100 | 0.025 | 0.1 | 0.1 | 0.1 | 0.1 | 0.1 | 0.025 | 0.1 |
| Ps. aeruginosa 32104 | 0.1 | 0.2 | 0.2 | 0.2 | 0.2 | 0.2 | 0.05 | 0.1 |
| Ps. aeruginosa 32121 | 0.05 | 0.05 | 0.1 | 0.05 | 0.05 | 0.1 | 0.025 | 0.05 |
| X. maltophilia IID 1275 | 0.05 | 0.1 | 0.05 | 0.1 | 0.2 | 0.39 | 0.78 | 0.2 |
| S. aureus FDA 209P | ≦0.003 | ≦0.003 | ≦0.003 | ≦0.003 | ≦0.003 | 0.2 | 0.1 | ≦0.003 |
| S. epidermidis 56500 | ≦0.003 | ≦0.003 | ≦0.003 | ≦0.003 | ≦0.003 | 0.39 | 0.2 | ≦0.003 |
| Str. pyrogenes G-36 | ≦0.003 | ≦0.003 | ≦0.003 | ≦0.003 | ≦0.003 | 0.2 | 1.56 | ≦0.003 |
| E. faecalis ATCC 19433 | 0.006 | 0.013 | 0.025 | 0.025 | 0.025 | 0.78 | 0.78 | 0.025 |
| S. aureus 870307 | ≦0.003 | 0.006 | 0.013 | 0.025 | 0.05 | >6.25 | 3.13 | 0.025 |
| Str. pneumoniae J24 | ≦0.003 | ≦0.003 | ≦0.003 | ≦0.003 | ≦0.003 | 0.78 | 0.1 | ≦0.003 |

INDUSTRIAL APPLICABILITY

The compounds of the invention are a quinolone pond represented by the following formula

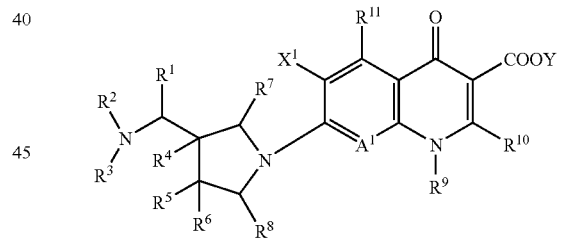

or the following formula

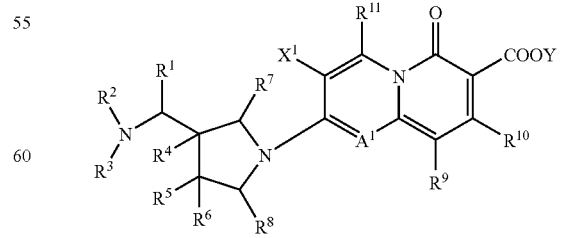

and a quinolone compound represented by the following formula wherein the substituent $R^1$ is an aromatic substituent, which are useful as antibacterial compounds because of their excellent antibacterial activity against Gram-negative bacteria and Gram-positive bacteria and also against various drug-resistant strains.

What is claimed is:

1. A compound represented by the following formula, or a salt or hydrate thereof

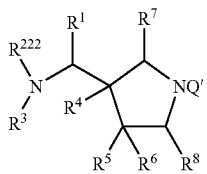

wherein $R^1$ represents an aryl group having from 6 to 10 carbon atoms or a heteroaryl group, wherein the heteroaryl group is a five-membered ring or a six-membered ring and contains from 1 to 4 hetero atoms selected from the group consisting of a nitrogen atom, an oxygen atom and a sulfur atom, wherein said aryl group and heteroaryl group may have one or more substituents selected from the group consisting of a halogen atom, a hydroxy group, a thiol group, an amino group, a nitro group, a cyano group, a carboxy group, a carbamoyl group, a phenyl group, an alkyl group having from 1 to 6 carbon atoms, an alkoxy group having from 1 to 6 carbon atoms, an alkylthio group having from 1 to 6 carbon atoms, an alkoxycarbonyl group having from 2 to 6 carbon atoms, an acyl group having from 2 to 5 carbon atoms and a heteroaryl group which is a five-membered ring or a six-membered ring and contains from 1 to 4 hetero atoms selected from the group consisting of a nitrogen atom, an oxygen atom and a sulfur atom, wherein the alkyl group, alkoxy group, alkylthio group, alkoxycarbonyl group, acyl group, phenyl group and heteroaryl group may have one or more substituents selected from the group consisting of a halogen atom, a hydroxy group, an alkoxy group having from 1 to 6 carbon atoms and an alkylthio group having from 1 to 6 carbon atoms, and the amino group may have one or two substituents selected from the group consisting of a formyl group, an alkyl group having from 1 to 6 carbon atoms, an acyl group having from 2 to 5 carbon atoms and an alkoxycarbonyl group having from 2 to 5 carbon atoms;

$R^{222}$ represents a hydrogen atom, an alkyl group having from 1 to 6 carbon atoms or a protective group of an amino group;

$R^3$ represents a hydrogen atom or an alkyl group having from 1 to 6 carbon atoms;

wherein the alkyl group represented by $R^{222}$ and $R^3$ may have one or more substituents selected from the group consisting of a hydroxy group, a halogen atom, an alkylthio group having from 1 to 6 carbon atoms and an alkoxy group having from 1 to 6 carbon atoms;

$R^4$, $R^5$ and $R^6$ each independently represents a hydrogen atom, a hydroxy group, a halogen atom, a carbamoyl group, an alkyl group having from 1 to 6 carbon atoms, an alkoxy group having from 1 to 6 carbon atoms or an alkylthio group having from 1 to 6 carbon atoms, wherein the alkyl group may have one or more substituents selected from the group consisting of a hydroxy group, a halogen atom and an alkoxy group having from 1 to 6 carbon atoms;

$R^7$ and $R^8$ each independently represents a hydrogen atom or an alkyl group having from 1 to 6 carbon atoms; and $Q'$ represents a protective group of an amino group;

wherein the protective group of an amino group is a protective group selected from the group consisting of a tert-butoxycarbonyl group, 2,2,2-trichloroethoxycarbonyl group, benzyloxycarbonyl group, para-methoxybenzyloxycarbonyl group, para-nitrobenzyloxycarbonyl group, acetyl group, methoxyacetyl group, trifluoroacetyl group, chloroacetyl group, pivaloyl group, formyl group, benzoyl group, tert-butyl group, benzyl group, para-nitrobenzyl group, para-methoxybenzyl group, triphenylmethyl group, methoxymethyl group, tert-butoxymethyl group, tetrahydropyranyl group, 2,2,2-trichloroethoxymethyl group, trimethylsilyl group, isopropyldimethylsilyl group, tert-butyldimethylsilyl group, tribenzylsilyl group, and tert-butyldiphenylsilyl group.

2. The compound of claim 1, or a salt or hydrate thereof, wherein $R^{222}$ and $Q'$ are not the same.

3. The compound of claim 1, or a salt or hydrate thereof, wherein $R^1$ is said aryl group having from 6 to 10 carbon atoms which may have a substituent.

4. The compound of claim 3, wherein said aryl group is a phenyl group or naphthyl group.

5. The compound of claim 1, or a salt or hydrate thereof, wherein $R^1$ is said heteroaryl group which may have a substituent.

6. The compound of claim 1, or a salt or hydrate thereof, wherein $R^1$ is said heteroaryl group which may have a substituent, and the heteroaryl group moiety is a furyl group, a thienyl group, a pyrrolyl group, an oxazolyl group, an isoxazolyl group, a thiazolyl group, an isothiazolyl group, an imidazolyl group, a pyrazolyl group, a furazanyl group, a pyridyl group, a pyrazinyl group, a pyrimidyl group, a pyridazinyl group, a triazinyl group or a tetrazinyl group.

7. The compound of claim 1, or a salt or hydrate thereof, wherein the each of $R^4$, $R^5$, $R^6$, $R^7$ and $R^8$ is a hydrogen atom.

8. A compound represented by the following formula, or a salt or hydrate thereof

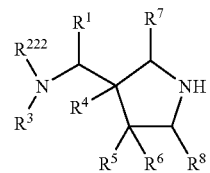

wherein $R^1$ represents an aryl group having from 6 to 10 carbon atoms or a heteroaryl group;

wherein the heteroaryl group is a five-membered ring or a six-membered ring and contains from 1 to 4 hetero atoms selected from the group consisting of a nitrogen atom, an oxygen atom and a sulfur atom;

wherein said aryl group and heteroaryl group may have one or more substituents selected from the group consisting of a halogen atom, a hydroxy group, a thiol group, an amino group, a nitro group, a cyano group, a carboxy group, a carbamoyl group, a phenyl group, an alkyl group having from 1 to 6 carbon atoms, an alkoxy group having from 1 to 6 carbon atoms, an alkylthio group having from 1 to 6 carbon atoms, an alkoxycarbonyl group having from 2 to 6 carbon atoms, an acyl group having from 2 to 5 carbon atoms and a heteroaryl group which is a five-membered ring or a six-membered ring and contains from 1 to 4 hetero atoms selected from the group consisting of a nitrogen atom, an oxygen atom and a sulfur atom;

wherein the alkyl group, alkoxy group, alkylthio group, alkoxycarbonyl group, acyl group, phenyl group and heteroaryl group may have one or more substituents selected from the group consisting of a halogen atom, a hydroxy group, an alkoxy group having from 1 to 6 carbon atoms and an alkylthio group having from 1 to 6 carbon atoms;

the amino group may have one or two substituents selected from the group consisting of a formyl group, an alkyl group having from 1 to 6 carbon atoms, an acyl group having from 2 to 5 carbon atoms and an alkoxycarbonyl group having from 2 to 5 carbon atoms;

$R^{222}$ represents a hydrogen atom, an alkyl group having from 1 to 6 carbon atoms or a protective group of an amino group;

$R^3$ represents a hydrogen atom or an alkyl group having from 1 to 6 carbon atoms;

wherein the alkyl group represented by $R^{222}$ and $R^3$ may have one or more substituents selected from the group consisting of a hydroxy group, a halogen atom, an alkylthio group having from 1 to 6 carbon atoms and an alkoxy group having from 1 to 6 carbon atoms;

$R^4$, $R^5$ and $R^6$ each independently represents a hydrogen atom, a hydroxy group, a halogen atom, a carbamoyl group, an alkyl group having from 1 to 6 carbon atoms, an alkoxy group having from 1 to 6 carbon atoms or an alkylthio group having from 1 to 6 carbon atoms;

wherein the alkyl group may have one or more substituents selected from the group consisting of a hydroxy group, a halogen atom and an alkoxy group having from 1 to 6 carbon atoms; and $R^7$ and $R^8$ each independently represents a hydrogen atom or an alkyl group having from 1 to 6 carbon atoms;

wherein the protective group of an amino group is a protective group selected from the group consisting of a tert-butoxycarbonyl group, 2,2,2-trichloroethoxycarbonyl group, benzyloxycarbonyl group, para-methoxybenzyloxycarbonyl group, para-nitrobenzyloxycarbonyl group, acetyl group, methoxyacetyl group, trifluoroacetyl group, chloroacetyl group, pivaloyl group, formyl group, benzoyl group, tert-butyl group, benzyl group, para-nitrobenzyl group, para-methoxybenzyl group, triphenylmethyl group, methoxymethyl group, tert-butoxymethyl group, tetrahydropyranyl group, 2,2,2-trichloroethoxymethyl group, trimethylsilyl group, isopropyldimethylsilyl group, tert-butyldimethylsilyl group, tribenzylsilyl group, and tert-butyldiphenylsilyl group.

9. The compound of claim 8, or a salt or hydrate thereof, wherein $R^1$ is an aryl group having from 6 to 10 carbon atoms which may have a substituent.

10. The compound of claim 9, wherein the aryl group is a phenyl group or a naphthyl group.

11. The compound of claim 8, or a salt or hydrate thereof, wherein $R^1$ is a heteroaryl group which may have a substituent.

12. The compound of claim 8, or a salt or hydrate thereof, wherein $R^1$ is a heteroaryl group which may have a substituent, and the heteroaryl group moiety is a furyl group, a thienyl group, a pyrrolyl group, an oxazolyl group, an isoxazolyl group, a thiazolyl group, an isothiazolyl group, an imidazolyl group, a pyrazolyl group, a furazanyl group, a pyridyl group, a pyrazinyl group, a pyrimidyl group, a pyridazinyl group, a triazinyl group or a tetrazinyl group.

13. The compound of claim 8, or a salt or hydrate thereof, wherein each of $R^4$, $R^5$, $R^6$, $R^7$ and $R^8$ is a hydrogen atom.

* * * * *